United States Patent
Bullock

(10) Patent No.: US 12,410,252 B2
(45) Date of Patent: Sep. 9, 2025

(54) ANTI-PD-1 IMMUNOGLOBULIN POLYPEPTIDES AND USES THEREOF

(71) Applicant: Trustees of Tufts College, Medford, MA (US)

(72) Inventor: Peter A. Bullock, Medford, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 18/690,247

(22) PCT Filed: Sep. 12, 2022

(86) PCT No.: PCT/US2022/076309
§ 371 (c)(1),
(2) Date: Mar. 7, 2024

(87) PCT Pub. No.: WO2023/039583
PCT Pub. Date: Mar. 16, 2023

(65) Prior Publication Data
US 2024/0376203 A1    Nov. 14, 2024

Related U.S. Application Data

(60) Provisional application No. 63/261,090, filed on Sep. 10, 2021.

(51) Int. Cl.
| | | |
|---|---|---|
| C07K 16/28 | (2006.01) | |
| A61K 39/395 | (2006.01) | |
| G01N 33/53 | (2006.01) | |
| G01N 33/68 | (2006.01) | |

(52) U.S. Cl.
CPC ......... *C07K 16/2818* (2013.01); *G01N 33/53* (2013.01); *G01N 33/68* (2013.01); *C07K 2317/565* (2013.01); *C07K 2317/622* (2013.01); *G01N 2333/70521* (2013.01)

(58) Field of Classification Search
None
See application file for complete search history.

(56) References Cited

U.S. PATENT DOCUMENTS

| | | | |
|---|---|---|---|
| 7,771,955 B2 | 8/2010 | Barbari et al. | |
| 8,008,449 B2 * | 8/2011 | Korman | A61K 39/00 530/388.15 |
| 8,779,105 B2 | 7/2014 | Korman et al. | |
| 9,492,539 B2 | 11/2016 | Korman et al. | |
| 10,441,655 B2 | 10/2019 | Korman et al. | |
| 2009/0111745 A1 | 4/2009 | Tomlinson | |
| 2014/0341902 A1 | 11/2014 | Maecker et al. | |
| 2014/0348743 A1 | 11/2014 | Korman et al. | |
| 2020/0138945 A1 | 5/2020 | Korman et al. | |
| 2021/0230243 A1 | 7/2021 | Desjarlais et al. | |

OTHER PUBLICATIONS

Topalian et al. N Engl J Med 2012; 366: 2443-2454.*
Arlauckas, Sean P., et al. "In vivo imaging reveals a tumor-associated macrophage-mediated resistance pathway in anti-PD-1 therapy." Science translational medicine 9.389 (2017): eaal3604.
Baek, Minkyung, et al. "Accurate prediction of protein structures and interactions using a three-track neural network." Science 373. 6557 (2021): 871-876.
Braunlein, Eva, and Angela M. Krackhardt. "Identification and characterization of neoantigens as well as respective immune responses in cancer patients." Frontiers in immunology 8 (2017): 309756.
Celis-Gutierrez, Javier, et al. "Quantitative interactomics in primary T cells provides a rationale for concomitant PD-1 and BTLA coinhibitor blockade in cancer immunotherapy." Cell reports 27.11 (2019): 3315-3330.
Chothia, Cyrus, and Arthur M. Lesk. "Canonical structures for the hypervariable regions of immunoglobulins." Journal of molecular biology 196.4 (1987): 901-917.
Ebo, Jessica S., et al. "An in vivo platform to select and evolve aggregation-resistant proteins." Nature communications 11.1 (2020): 1816.
Edelman, Gerald M., et al. "The covalent structure of an entire yG immunoglobulin molecule." Proceedings of the National Academy of Sciences 63.1 (1969): 78-85.
Gil-Garcia, Marcos, et al. "Combining structural aggregation propensity and stability predictions to redesign protein solubility." Molecular pharmaceutics 15.9 (2018): 3846-3859.
Gong, Haibiao, et al. "Near-infrared fluorescence imaging of mammalian cells and xenograft tumors with SNAP-tag." PloS one 7.3 (2012): e34003.
Gribskov, Michael, and Richard R. Burgess. "Sigma factors from *E. coli*, B. subtilis, phage SP01, and phage T4 are homologous proteins." Nucleic Acids Research 14.16 (1986): 6745-6763.

(Continued)

*Primary Examiner* — Ilia I Ouspenski
(74) *Attorney, Agent, or Firm* — Quarles & Brady LLP

(57) ABSTRACT

Aspects of the disclosure relate to PD-1 binding proteins comprising immunoglobulin domains which bind specifically to PD-1 and comprise at least three or six specific complementarity determining regions (CDRs) and which comprise a specific feature in a variable domain framework region(s), e.g., heavy variable domain framework 1, heavy domain framework 4, and/or light chain variable domain framework 3 region(s). In some embodiments, the PD-1 protein comprises the substitution(s) L 108G and/or THOR of the heavy chain reference sequence and/or 158R relative to the light chain reference sequence(s). The PD-1 binding proteins are useful, e.g., as immunologic adjuvants, for detecting and quantifying PD-1, monitoring patient responses to therapies, diagnosing PD-1 related conditions, and treating or preventing disorders involving PD-1 expressing cells, such as, e.g., cancers and autoimmune diseases. Also provided herein are antigen binding proteins comprising amino acid substitutions in the heavy chain framework 4 region for improved stability and solubility.

14 Claims, 18 Drawing Sheets
Specification includes a Sequence Listing.

(56) References Cited

OTHER PUBLICATIONS

Haeryfar, SM Mansour, and Todd D. Schell. "PD-1/PD-L1 co-inhibition shapes anticancer T cell immunodominance: facing the consequences of an immunological menage a trois." Cancer Immunology, Immunotherapy 67.11 (2018): 1669-1672.

Kang, Tae Hyun, and Baik Lin Seong. "Solubility, stability, and avidity of recombinant antibody fragments expressed in microorganisms." Frontiers in microbiology 11 (2020): 552011.

Kilgour, Elaine, et al. "Liquid biopsy-based biomarkers of treatment response and resistance." Cancer cell 37.4 (2020): 485-495.

Kohl, Johannes, et al. "Ultrafast tissue staining with chemical tags." Proceedings of the National Academy of Sciences 111.36 (2014): E3805-E3814.

Kuriata, Aleksander, et al. "Aggrescan3D (A3D) 2.0: prediction and engineering of protein solubility." Nucleic acids research 47.W1 (2019): W300-W307.

Lee, Ju Yeon, et al. "Structural basis of checkpoint blockade by monoclonal antibodies in cancer immunotherapy." Nature communications 7.1 (2016): 13354.

Meinke, Gretchen, Peter A. Bullock, and Andrew Bohm. "Crystal structure of the simian virus 40 large T-antigen origin-binding domain." Journal of virology 80.9 (2006): 4304-4312.

Meinke, Gretchen, and Peter A. Bullock. "Structural "snap-shots" of the initiation of SV40 replication." Small DNA Tumor Viruses. Horizon Scientific Press, Norwich (2012): 195-215.

Meinke, Gretchen, et al. "Structural based analyses of the JC virus T-antigen F258L mutant provides evidence for DNA dependent conformational changes in the C-termini of polyomavirus origin binding domains." PLoS Pathogens 12.1 (2016): e1005362.

Memarnejadian, Arash, et al. "PD-1 blockade promotes epitope spreading in anticancer CD8+ T cell responses by preventing fratricidal death of subdominant clones to relieve immunodomination." The Journal of Immunology 199.9 (2017): 3348-3359.

Mirdita, Milot, et al. "ColabFold: making protein folding accessible to all." Nature methods 19.6 (2022): 679-682.

Niemeijer, A. N., et al. "Whole body PD-1 and PD-L1 positron emission tomography in patients with non-small-cell lung cancer." Nature communications 9.1 (2018): 4664.

Patra, Ashok K., et al. "Optimization of inclusion body solubilization and renaturation of recombinant human growth hormone from *Escherichia coli*." Protein expression and purification 18.2 (2000): 182-192.

Peterson, Jesse N., et al. "Replication of JC virus DNA in the G144 oligodendrocyte cell line is dependent upon Akt." Journal of virology 91.20 (2017): 10-1128.

Poc, Pascal, et al. "Interrogating surface versus intracellular transmembrane receptor populations using cell-impermeable SNAP-tag substrates." Chemical Science 11.30 (2020): 7871-7883.

Retter, Ida, et al. "VBASE2, an integrative V gene database." Nucleic acids research 33.suppl_1 (2005): D671-D674.

Shin, Jong, et al. "Characterization of a single chain variable fragment of nivolumab that targets PD-1 and blocks PD-L1 binding." Protein Expression and Purification 177 (2021): 105766.

Shin, Jong, et al. "Analysis of JC virus DNA replication using a quantitative and high-throughput assay." Virology 468 (2014): 113-125.

Shin, Jong, et al. "Rational design of a Nivolumab-based ANTI-PD-1 single chain variable fragment that blocks the interaction between PD-1 expressed on T-CELLS and PD-L1 on CHO cells." Protein Expression and Purification 202 (2023): 106196.

Sormanni, Pietro, Francesco A. Aprile, and Michele Vendruscolo. "The CamSol method of rational design of protein mutants with enhanced solubility." Journal of molecular biology 427.2 (2015): 478-490.

Sun, Xiaoli, et al. "Development of SNAP-tag fluorogenic probes for wash-free fluorescence imaging." ChemBioChem 12.14 (2011): 2217-2226.

Waterhouse, Andrew, et al. "Swiss-Model: homology modelling of protein structures and complexes." Nucleic acids research 46.W1 (2018): W296-W303.

Worn, Arne, and Andreas Pluckthun. "Different equilibrium stability behavior of ScFv fragments: identification, classification, and improvement by protein engineering." Biochemistry 38.27 (1999): 8739-8750.

Wu, Thomas D., et al. "Peripheral T cell expansion predicts tumour infiltration and clinical response." Nature 579.7798 (2020): 274-278.

Zambrano, Rafael, et al. "AGGRESCAN3D (A3D): server for prediction of aggregation properties of protein structures." Nucleic acids research 43.W1 (2015): W306-W313.

International Search Report in PCT/US2022/076309; received on Feb. 1, 2023.

\* cited by examiner

```
  1  H H H H H H E N L Y F Q G   A A S   Q V Q L
  1  CACCATCACCATCACCATGAAAACCTGTATTTCCAGGGAGCAGCCTCGcaggtgcagctg
     GTGGTAGTGGTAGTGGTACTTTTGGACATAAAGGTCCCTCGTCGGAGCgtccacgtcgac 21  V E S G G G V V Q P G R S L R L D C K A
 61  gtggaaagcggcggcggcgtggtgcagccgggccgcagcctgcgcctggattgcaaagcg
     caccttccgccgccgccgcaccacgtcggccgggcgtcggacgcggacctaacgtttcgc 41  S G I T F S N S G M H W V R Q A P G K G
121  agcggcattacctttagcaacagcggcatgcattgggtgcgccaggcgccgggcaaaggc
     tcgccgtaatggaaatcgttgtcgccgtacgtaacccacgcggtccgcggcccgtttccg 61  L E W V A V I W Y D G S K R Y Y A D S V
181  ctggaatgggtggcggtgatttggtatgatggcagcaaacgctattatgcggatagcgtg
     gaccttacccaccgccactaaaccatactaccgtcgtttgcgataatacgcctatcgcac 81  K G R F T I S R D N S K N T L F L Q M N
241  aaaggccgctttaccattagccgcgataacagcaaaaacaccctgtttctgcagatgaac
     tttccggcgaaatggtaatcggcgctattgtcgttttgtgggacaaagacgtctactttg 101  S L R A E D T A V Y Y C A T N D D Y W G
301  agcctgcgcgcggaagataccgcggtgtattattgcgcgaccaacgatgattattggggc
     tcggacgcgcgccttctatggcgccacataataacgcgctggttgctactaataaccccg 121  Q G T L V T V S S G G G G S G G G G S G
361  caggcaccCTGgtgACCgtgagcagcggcggcggcggcagcggcggcggcggcagcggc
     gtccgtggGACcacTGGcactcgtcgccgccgccgtcgccgccgccgtcgccg 141  G G G S                       SEQ ID NO: 49
421  ggcggcggcagc                  SEQ ID NO: 50
     ccgccgccgtcg                  SEQ ID NO: 51
```

ANTI-PD-1 IMMUNOGLOBULIN POLYPEPTIDES AND USES THEREOF

CROSS-REFERENCE TO RELATED APPLICATIONS

This application is the national stage entry of Appln. No. PCT/US2022/076309. filed Sep. 12, 2022, claims priority to, and the benefit of, U.S. Appl. No. 63/261,090 filed Sep. 10, 2021. The contents of both of which are incorporated herein by reference in their entireties.

REFERENCE TO AN ELECTRONIC SEQUENCE LISTING

The contents of the electronic sequence listing (166118.01231.xml; Size: 75,541 bytes; and Date of Creation: Sep. 12, 2022) is herein incorporated by reference in its entirety.

BACKGROUND

The PD-1 pathway plays a vital role in inhibiting both adaptive and innate immune responses, promoting self-tolerance, and immune escape by cancers. PD-1 is expressed on immune cells, and the inhibition of PD-1 signaling can be beneficial for cancer patients. PD-1 binding proteins, e.g. nivolumab, pembrolizumab, and cemiplimab, have been approved for use in immunotherapy for cancer patients, e.g., for melanoma, breast cancer, cervical cancer, liver cancer, lung cancer, lymphoma, and stomach cancer. Accordingly, it would be beneficial to have additional PD-1 binding proteins, compositions thereof, therapeutic methods, and diagnostic methods that complement and/or expand existing therapies and diagnostics for cancer and/or autoimmune disease.

Currently, all FDA-approved therapeutic PD-1 binding proteins are antibodies. Single-chain antibody fragments (scFv's) have many advantages over antibodies, including, for example, smaller size and greater tissue penetration, decreased immunogenicity, and more cost-effective manufacturing. However, high-yield production of scFv's is generally limited by folding and stability properties (see e.g. Worn A, Pluckthun A, Biochemistry 38: 8739-50 (1999); Worn A, Pluckthun A, J Mol Biol 305: 989-1010 (2001)). One reason is the presence of multiple disulfide bonds in a protein can affect the order of folding and increase the number of thermodynamically favored conformations (see e.g. Chang J, Biochemistry 48: 9340-6 (2009)). Furthermore, misfolded scFv's are prone to self-aggregation and insolubility (Kang T, Seong B, Front Microbiol 11: 1927 (2020)). Consistent with these reports, the initial scFv generated from a PD-1 antibody was not soluble in tissue culture media and failed to block PD-1 signaling via PD-L1 in a cell-based assay. Thus, there exists a need in the art for antigen binding proteins generated from a PD-1 antibody that is soluble, stable and capable of binding PD-1 for use in cell-based assays, diagnostics and clinical therapeutics.

SUMMARY

Provided herein are PD-1 binding proteins comprising immunoglobulin domains having framework regions which reduce misfolding, increase stability, increase solubility, and/or reduce self-aggregation; and methods of using the aforementioned. These PD-1 binding proteins will have increased utility in cell-based, diagnostic and therapeutic applications due to the increased solubility and stability. In particular, the Examples provide an scFv comprising at least two mutations as compared to the reference PD-1 antibody that results in a PD-1 binding agent capable of blocking PD-1. The scFv's provided herein have greater stability and solubility as compared to the antibody. For example, certain amino acid modifications in framework regions are shown to improve stability and/or solubility of PD-1 binding proteins. In particular, certain amino acid residue substitutions are shown to improve stability and/or solubility, such as, e.g., L108G and/or T110R in an immunoglobulin heavy chain variable domain relative to nivolumab, wherein the heavy chain variable domain framework 1 region (VH-FR1) comprises a lysine residue positioned four amino acid residues carboxyl-terminal from the first amino acid of VH-FR1, and/or wherein the heavy chain variable domain framework 4 region (VH-FR4) comprises a glycine residue positioned six amino acid residues carboxy-terminal to the last amino acid residue of a heavy chain CDR-3 and/or an arginine residue positioned eight amino acid residues carboxy-terminal to the last amino acid residue of a heavy chain CDR-3 (V21K, L124G and T126R in the full length scFv of SEQ ID NO: 21). In particular, certain amino acid residue substitutions are shown to improve stability and/or solubility, such as, e.g., I58R in an immunoglobulin light chain variable domain relative to nivolumab, and/or wherein the light chain variable domain framework 3 region (VL-FR3) comprises an arginine residue positioned one amino acid residue carboxy-terminal to the last amino acid residue of a light chain CDR-2 (I202R in the full length scFV of SEQ ID NO: 21). The data of the disclosure demonstrate several examples of immunoglobulin-derived polypeptides that are stable and soluble in typical laboratory conditions, for example, in an aqueous buffered solution of pH 5 to 9 at 4 to 37° C., or more specifically in a commonly used mammalian cell culture media. These examples of immunoglobulin-derived proteins each bound human PD-1 with high affinity and specificity.

In a first aspect, provided herein is a PD-1 binding protein comprising (a) an immunoglobulin heavy chain variable region (VH) comprising: (1) a HCDR1 comprising the sequence of SEQ ID NO: 2; (2) a HCDR2 comprising the sequence of SEQ ID NO: 3; and (3) a HCDR3 comprising the sequence of SEQ ID NO: 4; and (b) an immunoglobulin light chain variable region (VL) comprising: (1) a LCDR1 comprising the sequence of SEQ ID NO: 5; (2) a LCDR2 comprising the sequence of SEQ ID NO: 6; and (3) a LCDR3 comprising the sequence of SEQ ID NO: 7; wherein the VH comprises a glycine at position 108 and an arginine at position 110 relative to SEQ ID NO: 23 or SEQ ID NO: 24; and/or wherein the VH comprises a heavy chain variable domain framework 4 region (VH-FR4) comprising a glycine residue positioned six amino acid residues carboxy-terminal to the last amino acid residue of HCDR3 and an arginine residue positioned eight amino acid residues carboxy-terminal to the last amino acid residue of HCDR3. In some embodiments, the VH of the PD-1 binding protein comprises a lysine at position 5 relative to SEQ ID NO: 23 or SEQ ID NO: 24, and/or wherein the heavy chain variable domain framework 1 region (VH-FR1) comprises a lysine residue positioned 26 amino acid residues amino-terminal from the first amino acid of HCDR1 or positioned one amino acid residue carboxyl-terminal from the first amino acid of VH-FR1. In some embodiments, the VL of the PD-1 binding protein comprises an arginine at position 58 relative to SEQ ID NO: 29 or SEQ ID NO: 30 and/or wherein the light chain variable domain framework 3 region (VL-FR3) comprises an arginine residue positioned one amino acid residue carboxy-terminal to the last amino acid residue of a LCDR2. In some further embodiments, the PD-1 binding protein comprises a polypeptide comprising the polypeptide sequence having at least 90%, at least 95%, at least 96%, at least 97%, at least 98%, or at least 99% sequence identity to any one of SEQ ID NOs: 8-21.

In some embodiments, the PD-1 binding protein binds to a human PD-1 protein with high affinity, such as, e.g., with a binding characterized by a dissociation constant (Kd) of at least about $10^{-7}$ M, at least about $10^{-8}$ M, and/or at least about $10^{-9}$ M.

In some embodiments, the PD-1 binding protein comprises the heavy chain variable domain comprising SEQ ID NO: 8 or 16.

In some embodiments, the PD-1 binding protein comprises the light chain variable domain comprising SEQ ID NO: 9 or 17.

In some embodiments, the PD-1 binding protein comprises a polypeptide linker between the heavy chain variable domain and the light chain variable domain. In some further embodiments, the PD-1 binding protein comprises a polypeptide comprising, from amino- to carboxy-terminus, the heavy chain variable domain, the polypeptide linker, and the light chain variable domain. In some further embodiments, the polypeptide linker comprises SEQ ID NO: 38.

In some aspects, provided herein is a PD-1 binding protein comprising the polypeptide sequence of any one of SEQ ID NOs: 10-11, 14-15, 18-19, and 21.

In some embodiments, the PD-1 binding protein comprises a polypeptide having a carboxy-terminal cysteine residue.

In some embodiments, the PD-1 binding protein comprises a detection-promoting agent, such as, e.g., a fluorescent agent or radioisotope.

In some embodiments, the PD-1 binding protein is immobilized on a solid substrate.

In some embodiments, the PD-1 binding protein is capable of inhibiting a human PD-1 protein function, such as, e.g., inhibiting PD-1 signaling, inhibiting PD-1 binding to a cognate ligand, inhibiting PD-L1 binding to human PD-1, and/or inhibiting PD-L2 binding to human PD-1.

In further aspects, provided herein is a nucleic acid or polynucleotide encoding a PD-1 binding protein described herein, as well as an expression vector comprising the aforementioned polynucleotide, and a host cell comprising the aforementioned polynucleotide and/or expression vector.

In another aspect, provided herein is a composition comprising a PD-1 binding protein described herein and a pharmaceutically acceptable carrier or excipient.

In another aspect, provided herein is a kit comprising (a) a PD-1 binding protein described herein and (b) a device or at least one additional reagent.

In another aspect, provided herein are methods of using the PD-1 binding proteins described herein and/or a composition thereof. In some aspects, provided herein is a method of treatment comprising administering to a subject in need thereof a therapeutically effective amount of a PD-1 binding protein described herein and/or a composition thereof. In some aspects, provided herein is a method of detecting PD-1, the method comprising (i) contacting a sample with a PD-1 binding protein described herein, and (ii) detecting the PD-1 binding protein. In some aspects, provided herein is a method of detecting PD-1, the method comprising (i) administering to a subject a PD-1 binding protein described herein or a composition thereof, and (ii) detecting the PD-1 binding protein.

Also provided herein are antigen binding proteins having heavy chain framework 4 regions (VH-FR4) which reduce misfolding, increase stability, increase solubility, and/or reduce self-aggregation. In a first aspect, provided herein is an antigen binding protein comprising a heavy chain framework 4 region (VH-FR4) comprising at least one of: a glycine residue positioned six amino acid residues carboxyl-terminal from the last amino acid residue of a heavy chain CDR-3, and an arginine residue positioned eight amino acid residues carboxy-terminal to the last amino acid residue of a heavy chain CDR-3.

In some embodiments, the VH-FR4 comprises a sequence selected from: WGQGTGVRVSS (SEQ ID NO: 28), WGQGTGVTVSS (SEQ ID NO: 43), and WGQGTLVRVSS (SEQ ID NO: 44).

In some embodiments, the antigen-binding protein is selected from a single-chain variable fragment (scFv), a diabody, a framework region 4 polypeptide (FR3-CDR3-FR4), a Fab fragment, and an antibody. In some embodiments, the antigen-binding protein is a scFv.

In some embodiments, the antigen-binding protein comprises a polypeptide wherein the final carboxy-terminal amino acid residue is a cysteine residue. In some embodiments, the antigen-binding protein comprises a detection-promoting agent. In some embodiments, the detection-promoting agent is selected from a fluorescent agent and a radioisotope.

In an aspect, provided herein is a composition comprising a) an antigen binding protein described herein; and b) a pharmaceutically acceptable carrier or excipient.

In an aspect, provided herein is a nucleic acid or a polynucleotide encoding an antigen binding protein described herein, as well as an expression vector comprising the aforementioned polynucleotide, and a host cell comprising the aforementioned polynucleotide and/or expression vector.

In an aspect, provided herein is a kit comprising a) an antigen binding protein described herein, and a device or at least one additional reagent.

BRIEF DESCRIPTION OF THE DRAWINGS

FIG. 3A (left model) shows the results for the original scFv ("wildtype"). FIG. 3A (right model) shows the results for anti-PD-1(dm) ("double mutant"), which comprises two point mutations relative to the original anti-PD-1 scFv:

L124G and T126R. As shown in FIG. 3A (left model), the Aggescan3D algorithm labeled L124 and T126 as two of the most insoluble/aggregation promoting residues on the surface of the scFv. As shown in FIG. 3A (right model), the anti-PD-1dm variant was predicted to have greatly improved solubility (note the absence of a cluster of red colored residues present in FIG. 3 (left model)). FIG. 3B compares the Aggrescan 3D based depictions of the surface of the anti PD-1 scFv single and double mutants. FIG. 3B (left model) shows a surface representation of the T126R anti-PD-1 "single mutant". The location of mutant residue R126 is indicated by the box outlined in purple. Nearby residues of interest, including V27 and L124, are also indicated. FIG. 3B (right model) shows a surface representation of the anti PD-1 "double mutant". The locations of mutant residues G124 and R126 are indicated by the boxes outlined in purple. Importantly, the L124G and T126R substitutions have eliminated a hydrophobic patch (the cluster of "red residues" presented in FIG. 3A (left model). For reference, V27 is also indicated.

FIGS. 15A-15B show the conservation of anti-PD-1 scFv residues L124 and T126 in other scFv's and diabodies. Following a protein BLAST search, the scFv molecules and diabodies identified on the left side of the tables were aligned with the wt anti-PD-1 scFv using clustal-omega. The scFv's presented in FIG. 15A have known structures, their PDB identification codes are in parentheses, while those presented in FIG. 15B have unknown structures. In both tables, the top line presents the sequence of the wt anti-PD-1 in the vicinity of residues L124 and T126 (labeled with a dot). Residues homologous to Leu 124 and Thr 126 in the identified scFv's are also colored. For reference, those sequences comprising heavy (H) CDR3 and the scFv specific Gly/Ser linkers are also indicated.

DETAILED DESCRIPTION

Figure 1:
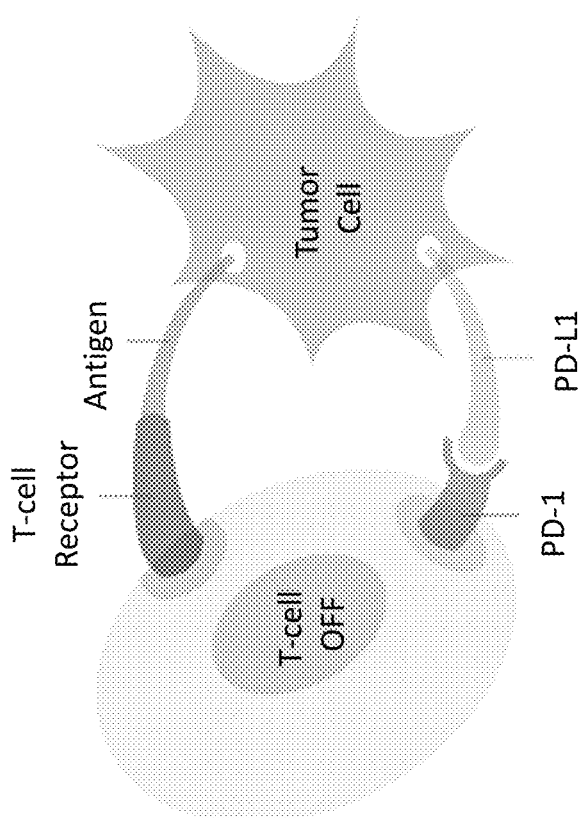
FIG. 1 is an overview of PD-1 targeted immunotherapy. T-cells are turned off when tumor cell derived PD-L1 interacts with PD-1 present on T-cells (left drawing). However, antibodies that can disrupt the interaction between PD-1 and PD-L1 and can reactivate exhausted T-cells to continue their anti-tumor activity (right drawing).
Figure 1:
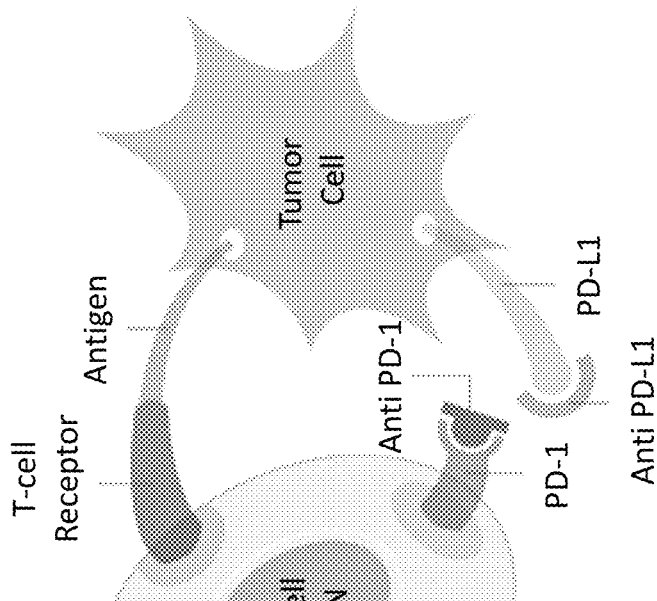

Provided herein are PD-1 binding proteins comprising one or more immunoglobulin regions and methods of using the aforementioned. The compositions and methods provided herein are based at least in part on the inventor's development of single chain variable fragments (scFv's) from nivolumab which retain nivolumab's ability to specifically bind PD-1 with high affinity and selectivity. These scFv's are engineered to increase stability and/or solubility by altering amino acid residues, such as, e.g., in the heavy chain variable fragment framework 1 or 4 regions (VH-FR1 or VH-FR4) and/or in the light chain variable fragment framework 3 region (VL-FR3). Uses of these anti-PD-1 scFv's for detecting PD-1, blocking PD-1 signaling/function, and targeted delivery to PD-1 expressing cells are explored. Advantages of nivolumab-derived scFv molecules compared to nivolumab include relatively smaller sizes, increased tissue and tumor penetration, and reduced manufacturing costs. An overview of PD-1 targeted immunotherapy is provided in FIG. 1. Approaches to cancer therapy have been revolutionized by monoclonal antibodies that disrupt the interaction between T-cell derived PD-1 and immunosuppressive ligands, such as PD-L1 (FIG. 1). For example, the full-length monoclonal antibodies bind to PD-1 on the surface of T-cells and block interactions with PD-L1 situated on tumor cells. As a result of blocking the PD-1/PD-L1 interaction, the T-cells are re-activated, and their proliferation is further promoted. To date all PD-1 binding proteins have been full monoclonal antibodies. Provided herein are scFv's capable of binding PD-1 and blocking its interaction with PD-L1 to restore T cell activity.

Also provided herein are antigen binding proteins having amino acid substitutions in the heavy chain framework 4 regions (VH-FR4) which reduce misfolding, increase stability, increase solubility, and/or reduce self-aggregation. The heavy chain framework 4 region (VH-FR4) comprises a glycine residue positioned six amino acid residues carboxyl-terminal from the last amino acid residue of a heavy chain CDR-3, an arginine residue positioned eight amino acid residues carboxy-terminal to the last amino acid residue of a heavy chain CDR-3, or both. Similarly to the PD-1 binding proteins, the antigen binding proteins are modified to improve their stability and solubility, and reduce their misfolding and self-aggregation.

Definitions

As used herein, the term PD-1 refers to a biomolecule found in mammals and is also referred to as CD279, programmed cell death protein 1, PDCD1, PD1, SLEB2, hSLE1, and programmed cell death 1. PD-1 typically occurs as a type I membrane protein of about 55 kDa (e.g. a 288 amino acid residue polypeptide in humans) having an extracellular domain, a transmembrane domain, and an intracellular tail. PD-1 can be found expressed on the surface of T and/or B cells, and PD-1 may play a key role in reducing ineffective, harmful, or persistent immune responses and in regulating immune tolerance (e.g. maintaining self-tolerance). In addition, PD-1 may act by inhibiting immune responses as part of an immune checkpoint mechanism involving programmed cell death and including signaling by a PD-1 ligand(s) expressed by malignant cells, such as, e.g., a cancer cell or infected cell trying to evade immunosurveillance.

Immunoglobulin (Ig) proteins (members of the Ig family) have a structural domain known as an Ig domain. Ig domains range in length from about 70-110 amino acid residues and possess a characteristic Ig-fold, in which typically seven to nine antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a hypervariable region or complementarity determining region (CDR), which is important for the specificity of antibodies binding to their epitopes.

As used herein, the term "antibody" refers to various immunoglobulin proteins having a structural domain known as an Ig domain which is involved in antigen binding, and thus, the term antibody encompasses the broadest of antibody formats having antigen binding capability. For example, native IgG antibodies are heterotetrameric glycoproteins of about 150,000 daltons, composed of two identical light chains and two identical heavy chains that each comprise at least one Ig domain involved in antigen binding. Thus, the typical IgG contains at least four Ig domains involved in antigen binding. From amino- to carboxy-terminus, each heavy chain has a variable region (VH), also called a variable heavy domain or a heavy chain variable domain, followed by three constant domains (CH1, CH2, and CH3). Similarly, from amino- to carboxy-terminus, each light chain has a variable region (VL), also called a variable light domain or a light chain variable domain, followed by a constant light (CL) domain. The light chain of an antibody may be assigned to certain types, e.g. kappa (κ) and lambda (λ), based on the amino acid sequence of its constant domain. Unless dictated otherwise by contextual constraints, the term "antibody" further comprises all classes of antibodies (e.g. IgA, IgD, IgE, IgG, and IgM) and all subclasses (e.g. IgG1, IgG2, IgG3, IgG4, IgA1, and IgA2). If desired, the class of an antibody may be "switched" using methods known to the skilled worker. For example, an antibody that was originally produced as an IgM molecule may be class switched to an IgG antibody. Class switching techniques also may be used to convert one IgG subclass to another, for example, from IgG1 to IgG2 or IgG4; from IgG2 to IgG1 or IgG4; or from IgG4 to IgG1 or IgG2. Engineering of antibodies to generate constant region chimeric molecules, such as by combining regions from different IgG subclasses, can also be performed by the skilled worker using known methods.

As used herein, the term "variable region" or "variable domain" refers to the polypeptide domain of an antibody heavy or light chain that is involved in binding the antibody to an antigen. The variable domains of the heavy chain and light chain (VH or VH and VL or VL, respectively) of a native antibody generally have similar structures (see e.g. Kindt T et al, Kuby Immunology, at pg. 91 (W.H. Freeman and Co., 6th ed., (2007)).

As used herein, the term "heavy chain variable (VH) domain" or "light chain variable (VL) domain" respectively refer to any antibody VH or VL domain (e.g. a human VH or VL domain), as well as any derivative thereof that retains, at least qualitatively, an antigen binding ability of the corresponding antibody from which it was derived (e.g. a humanized VH or VL domain derived from a native murine VH or VL domain). A VH or VL domain comprises both "hypervariable" regions and "framework" regions.

As used herein, the term "framework" or "FR" refers to antibody variable domain residues other than hypervariable region (HVR) residues. The FR of a variable domain generally consists of four FR domains: FR1, FR2, FR3, and FR4.

As used herein, the term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the VH (H1, H2, and H3), and three in the VL (L1, L2, and L3). HVRs generally comprise amino acid residues from the hypervariable loops and/or from the "complementarity determining region" (CDR) (also called a "complementary determining region"), the latter being of highest sequence variability and/or involved in antigen recognition. Accordingly, the FR and HVR sequences generally appear in the following sequence, from amino-terminus to carboxy-terminus, in a VH (or VL): FR1-H1(L1)-FR2-H2(L2)-FR3-H3(L3)-FR4. Thus, a typical 4-chain antibody comprises (1) a VH comprising (VH)FR1-VHCDR1-(VH)FR2-VHCDR2-(VH)FR3-VHCDR3-(VH)FR4 and (2) a VL comprising (VL)FR1-VLCDR1-(VL)FR2-VLCDR2-(VL)FR3-VLCDR3-(VL)FR4. However, a single VH or VL domain in isolation may be sufficient to confer antigen-binding specificity.

Variable regions and CDRs in an antibody sequence can be identified according to general rules that have been developed in the art, such as, as set out above, for example using the Kabat nomenclature system, or by aligning the sequences against a database of known variable regions (see e.g. Kabat et al, *Sequences of Proteins of Immunological Interest*, 5th Ed. Public Health Service, National Institutes of Health, Bethesda, Md. (1991)). Methods for identifying these regions are described in *Antibody Engineering* (Rontermann R, Dübel S, eds., Springer, New York, NY (2001)) and *Current Protocols in Immunology* (Coligan J et al. (eds), John Wiley and Sons Inc., Hoboken, NJ, (2000)). Exemplary databases of antibody sequences are described in, and can be accessed through, the "Abysis" website and/or the VBASE2 website (see Retter et al., Nucl Acids Res 33(Database issue): D671-4 (2005)).

As will be appreciated by those in the art, the exact numbering and placement of the CDRs can be different among different numbering systems. Illustrative hypervariable loops generally occur at about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region (Kabat E (1991), supra), and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia, Lesk, J Mol Biol 196: 901-17 (1987). With the exception of CDR1 in VH, CDRs generally comprise the amino acid residues that form the hypervariable loops.

Unless otherwise indicated, HVR and CDR residues and other residues in the variable domain (e.g. FR residues) are numbered herein according to Kabat et al, *Sequences of Proteins of Immunological Interest*, 5th Ed. Public Health Service, National Institutes of Health, Bethesda, Md. (1991), referred to herein as "Kabat." Certain sequence identifiers are herein followed by a parenthetical indicating an alternative numbering scheme used instead of Kabat, such as, e.g., Chothia, Kabat/Chothia, McCallum/Contact, IMGT, Gelfand, Honneger, Martin, North, or AbM.

As used herein, the terms "HCDR1," "HCDR2," or "HCDR3" are used to refer to CDRs 1, 2, or 3, respectively, in a VH domain, and the terms "LCDR1," "LCDR2," and "LCDR3" are used to refer to CDRs 1, 2, or 3, respectively, in a VL domain. As used herein, the terms "HABR1," "HABR2," or "HABR3" are used to refer to ABRs 1, 2, or 3, respectively, in a VH domain, and the terms "LABR1," "LABR2," or "LABR3" are used to refer to CDRs 1, 2, or 3, respectively, in a VL domain. For camelid VHH fragments, IgNARs of cartilaginous fish, VNAR fragments, some single domain antibodies, and derivatives thereof, there is a single, heavy chain variable domain comprising the same basic arrangement: FR1, CDR1, FR2, CDR2, FR3, CDR3, and FR4. As used herein, the terms "HCDR1," "HCDR2," or "HCDR3" may be used to refer to CDRs 1, 2, or 3, respectively, in a single heavy chain variable domain. A single VH domain may be sufficient to confer antigen-binding specificity.

For heavy chain constant region amino acid positions, numbering is according to the Eu index described in Edelman G et al., Proc Natl Acad Sci U.S.A. 63: 78-85 (1969), describing the amino acid sequence of the myeloma protein Eu, which reportedly was the first human IgG1 sequenced. The Eu index of Edelman is also set forth in Kabat E (1991), supra. Thus, the terms "Eu index as set forth in Kabat" or "Eu index of Kabat" or "Eu index" or "Eu numbering" in the context of the heavy chain refers to the residue numbering system based on the human IgG1 Eu antibody of Edelman et al, supra, as set forth in Kabat E (1991), supra. The numbering system used for the light chain constant region amino acid sequence is similarly set forth in Kabat E (1991), supra.

As used herein, an "antigen binding protein" refers to protein having at least one complementarity determining region (CDR) supported by a framework region (FR). Non-limiting examples of antigen binding proteins include but are not limited to antibodies, scFv, Fv, Fab, Fab', Fab'-SH, F(ab')2), linear antibodies, and numerous additional antigen-binding antibody derivatives described below and/or known to the skilled person.

As used herein, an "antibody fragment" refers to a molecule other than an intact antibody that comprises a polypeptide equivalent to a portion of an intact antibody wherein the antibody fragment binds an antigen, such as, e.g., the antigen bound by an intact antibody comprising the antibody fragment. Non-limiting examples of antibody fragments include but are not limited to scFv, Fv, Fab, Fab', Fab'-SH, F(ab')2), linear antibodies, and numerous additional antigen-binding antibody derivatives described below and/or known to the skilled person. Antibody fragments can be made by various techniques, including but not limited to proteolytic digestion of an intact antibody (e.g. a full-length antibody) as well as production by recombinant host cells (e.g. using E. coli and/or phage). Antibody fragments can be made by various techniques, including but not limited to recombinant engineering of immunoglobulin heavy and/or light variable regions into a single-chain polypeptide, e.g., to form a scFv.

The terms "Fab" or "Fab region" as used herein refers to a polypeptide that comprises the VH, CH1, VL, and CL immunoglobulin domains of an antibody. Fab may refer to this region in isolation, or this region in the context of a full-length antibody or antibody fragment.

The terms "Fv" or "Fv fragment" or "Fv region" as used herein refers to a polypeptide that comprises the VL and VH domains of a single antibody. As will be appreciated by those in the art, these are made up of two domains, a variable heavy domain and a variable light domain.

The terms "single chain Fv" or "scFv" as used herein refers to a polypeptide comprising a variable heavy domain covalently attached to a variable light domain, generally using a linker. An scFv domain can be in either orientation from amino- to carboxy-terminus (VH-linker-VL or VL-linker-VH). In general, the linker is a scFv linker generally known in the art and/or described herein.

As used herein, the term "affinity" refers to the strength of the sum total of noncovalent interactions between a single binding site of a molecule (e.g. an antibody or its paratope) and its binding partner (e.g. an antigen or epitope). Unless indicated otherwise, as used herein, "binding affinity" refers to intrinsic binding affinity which reflects a 1:1 interaction between members of a binding pair (e.g. an antibody and its antigen). Affinity can be measured by methods known to the skilled worker, including those described herein. The affinity of a molecule X for its partner Y can generally be represented by the dissociation constant (KD). Specific illustrative embodiments of methods of measuring binding affinity are described herein.

As used herein, "specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target (e.g. nivolumab).

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of $K_D$ to Ka (i.e., $K_D$/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ is measured using flow cytometry with antigen-expressing cells. In some embodiments, the $K_D$ value is measured with the antigen immobilized. In other embodiments, the $K_D$ value is measured with the antibody (e.g., parent mouse antibody, chimeric antibody, or humanized antibody variants) immobilized. In some embodiments, the $K_D$ value is measured in a bivalent binding mode. In other embodiments, the $K_D$ value is measured in a monovalent binding mode. Specific binding for a particular antigen or an epitope can be exhibited, for example, by an antibody having a $K_D$ for an antigen or epitope of at least about $10^{-7}$ M, at least about $10^{-8}$ M, at least about $10^{-9}$ M, at least about $10^{-10}$ M, at least about $10^{-11}$ M, at least about $10^{-12}$ M, at least about $10^{-13}$ M, at least about $10^{-14}$ M. Typically, an antibody that specifically binds an antigen will have a $K_D$ that is 20-, 50-, 100-, 500-, 1000-, 5,000-, 10,000- or more times greater for a control molecule relative to the antigen or epitope.

The terms "PD-1 binding protein", "anti-PD-1 binding protein", or "anti-PD-1 protein" refers to a protein that is capable of binding PD-1 with sufficient affinity such that the protein is useful as for detecting PD-1 or as a PD-1 diagnostic and/or PD-1 targeting therapeutic agent due to its specific binding and sufficient affinity to PD-1. The term PD-1 binding protein may be used to refer to an antibody or an antibody fragment capable of binding PD-1. In some embodiments, the extent of binding of an PD-1 binding protein to an unrelated, non-PD-1 protein is less than about 10% of the binding of the PD-1 binding protein to PD-1 as measured, e.g., by a radioimmunoassay. In some embodiments, the PD-1 binding protein has a dissociation constant (KD) of <100 nM, 10 nM, <1 nM, <0.1 nM, <0.01 nM, or <0.001 nM (e.g. $10^8$ moles/liter (M) or less, e.g. from $10^8$ M to $10^{13}$ M, e.g., from $10^9$ M to $10^{13}$ M).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

As used herein, the phrase "antibody effector function" refer to those biological activities attributable to an Fc region of an antibody or derivative thereof, which vary with the antibody isotype. Examples of antibody effector functions include: Clq binding and complement-dependent cytotoxicity (CDC); Fc receptor binding (including the neonatal Fc receptor (FcRn) or Brambell receptor), antibody-dependent cellular cytotoxicity (ADCC); phagocytosis; down-regulation of cell surface receptors (e.g. PD-1, PD-L1, PD-L2, B7-1/2, B7-H4, or B7-H3); T cell activation, and B cell activation.

The term "heavy constant region" refers to the CH1-hinge-CH2-CH3 portion of a human IgG antibody.

The term "light constant region" refers to the CL domain from a kappa or lambda light chain of an antibody.

As used herein, the terms "Fc" or "Fc region" or "Fc domain" refers to part of the fragment crystallizable region, a carboxy-terminal proximal region of certain heavy chains of native immunoglobulins that contains at least a portion of the constant region, such as, e.g., at least the second and third constant (CH) domains and a glycosylation site. The terms "Fc" or "Fc region" or "Fc domain" includes native sequence Fc regions and variant or mutated Fc regions or fragments thereof. Unless otherwise specified herein, numbering of amino acid residues in the Fc region or constant region is according to the EU numbering system, also called the EU index, as described in Kabat E (1991), supra.

As used herein, the term "Fc region having ADCC activity" refers to an Fc region capable of antibody-dependent cell-mediated cytotoxicity (ADCC) through binding of a cytolytic Fc receptor (e.g. FcγRIIIa) on a cytolytic immune effector cell expressing the Fc receptor (e.g. an NK cell or CD8+ T cell).

As used herein, the term "Fc region having CDC activity" refers to an Fc region capable of mediating complement-dependent cytotoxicity (CDC) through binding of C1q complement protein and activation of the classical complement system.

As used herein, the term "complement" refers collectively to those components in normal serum that, together with antigen-bound antibodies, exhibit the ability to lyse cells. Complement consists of a group of serum proteins that act in concert and in an orderly sequence to exert their effect. The phrase "classical complement system", as used herein, refers to a specific pathway for the activation of complement requiring the ordered function of nine major protein components designated C1 through C9 and providing amplification of large amounts of complement from a relatively small initial signal. For several steps in the activation process, the product is an enzyme that catalyzes the subsequent step.

As used herein, the term "immunoconjugate" or "conjugate" is used broadly and includes the covalent or non-covalent association of any material with a protein comprising an immunoglobulin domain, regardless of the method of association. For example, an "immunoconjugate" may be an immunoglobulin protein conjugated to one or more heterologous molecule(s), including but not limited to a cytotoxic agent or detection-promoting agent (e.g. a label or tag).

Throughout this specification, the term "bispecific" will be understood to include immunoglobulin domain containing molecules which bind two or more target biomolecules or which bind the same target biomolecule at two or more different epitopes, whether non-overlapping or overlapping epitopes (e.g. a bivalent biparatopic molecule).

For purposes of the present invention, the phrase "derived from" when referring to a polypeptide or polypeptide region means that the polypeptide or polypeptide region comprises highly similar amino acid sequences originally found in a "parental" protein or molecule and which may now comprise certain amino acid residue additions, deletions, truncations, rearrangements, or other alterations relative to the original polypeptide or polypeptide region as long as a certain function(s) (e.g. antigen binding affinity) and a structure(s) of the "parental" molecule are substantially conserved. The skilled worker will be able to identify a parental molecule (e.g. an antibody sequence) from which a polypeptide or polypeptide region (e.g. a CDR, HVR, VH, and/or VL) was derived using techniques known in the art, e.g., protein sequence alignment software.

The terms "associated", "associating", "linked", or "linking" with regard to the claimed invention refers to the state of two or more components of a molecule being joined, attached, connected, or otherwise coupled to form a single molecule or the act of making two molecules associated with each other to form a single molecule by creating an association, linkage, attachment, and/or any other connection between the two molecules. For example, the term "linked" may refer to two or more components associated by one or more atomic interactions such that a single molecule is formed and wherein the atomic interactions may be covalent and/or non-covalent. Non-limiting examples of covalent associations between two components include peptide bonds and cysteine-cysteine disulfide bonds. Non-limiting examples of non-covalent associations between two molecular components include ionic bonds.

For purposes of the present invention, the term "linked" refer to two or more molecular components associated by one or more atomic interactions such that a single molecule is formed and wherein the atomic interactions includes at least one covalent bond.

For purposes of the present invention, the term "linking" refers to the act of creating a linked molecule as described herein.

For purposes of the present invention, the term "fused" refers to two or more proteinaceous components associated by at least one covalent bond which is a peptide bond, regardless of whether the peptide bond involves the participation of a carbon atom of a carboxyl acid group or involves another carbon atom, such as, e.g., the alpha-carbon, beta-carbon, gamma-carbon, delta-carbon, etc. Non-limiting examples of two proteinaceous components fused together include, e.g., an amino acid, peptide, or polypeptide fused to a polypeptide via a peptide bond such that the resulting molecule is a single, continuous polypeptide.

For purposes of the present invention, the term "fusing" refers to the act of creating a fused molecule as described herein, such as, e.g., a fusion protein generated from the recombinant fusion of genetic regions which when translated produces a single proteinaceous molecule.

The symbol "::" means the polypeptide regions before and after it are physically linked together by at least one peptide bond (fused) to form a continuous polypeptide.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. The degree of identity between an amino acid sequence of the present invention ("invention sequence") and the parental amino acid sequence may be calculated as the number of exact matches in an alignment of the two sequences, divided by the length of the "invention sequence," or the length of the parental sequence, whichever is the shortest. The result is expressed in percent identity. Alignment for purposes of determining percent amino acid sequence identity can be achieved in various ways that are within the skill in the art, for instance, using publicly available computer software such as BLAST, BLAST-2, ALIGN, ALIGN-2, or Megalign (DNASTAR) software. Those skilled in the art can determine appropriate parameters for measuring alignment, including any algorithms needed to achieve maximal alignment over the full-length of the sequences being compared. One particular program is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An example of an implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters.

I. Compositions

Provided herein are various PD-1 binding proteins, polynucleotides encoding such proteins, and compositions comprising such proteins. Each PD-1 binding protein comprises one or more immunoglobulin regions for binding to PD-1. The data of the disclosure demonstrate several examples of immunoglobulin-derived polypeptides that bind human PD-1 with high affinity and/or inhibit PD-1 interactions with PD-L1. The data demonstrate several examples of immunoglobulin-derived polypeptides that are stable and soluble under typical protein conditions, for example, in an aqueous buffer solution of pH 5 to 9 at 4 to 37° C. (e.g., a commonly used mammalian cell culture medium) or, for example, in mammalian plasma, sera, or blood. In particular, certain amino acid residue substitutions are shown to improve stability and/or solubility, such as, e.g., wherein an immunoglobulin heavy chain variable domain comprises a glycine at position 108 and/or an arginine at position 110 relative to SEQ ID NO: 23 or 24; and/or wherein an immunoglobulin heavy chain variable domain framework 4 region (VH-FR4) comprises a glycine residue positioned six amino acid residues carboxy-terminal to the last amino acid residue of a heavy chain variable domain CDR-3 (vHCDR-3) (e.g. G108) and/or an arginine residue positioned eight amino acid residues carboxy-terminal to the last amino acid residue of a heavy chain variable domain CDR-3 (vHCDR-3) (e.g. R110); and/or wherein an immunoglobulin heavy chain variable domain comprises a lysine at position 5 relative to SEQ ID NO: 23 or 24; and/or wherein the heavy chain variable domain framework 1 region (VH-FR1) comprises a lysine residue positioned 26 amino acid residues amino-terminal from the first amino acid of a heavy chain variable domain CDR1 (vHCDR-1) (e.g. K5) and/or positioned four amino acid residues carboxyl-terminal from the first amino acid of an immunoglobulin heavy chain variable domain framework 1 region (VH-FR1) (e.g. K5); and/or wherein an immunoglobulin light chain variable domain comprises an arginine at position 58 relative to SEQ ID NO: 29 or 30; and/or wherein an immunoglobulin light chain variable domain framework 3 region (VL-FR3) comprises an arginine residue positioned one amino acid residue carboxy-terminal to the last amino acid residue of a light chain CDR-2 (vLCDR-2) (e.g. R58).

Immunoglobulin Regions

The PD-1 binding proteins of the disclosure each comprise at least one immunoglobulin binding region such that the PD-1 binding protein binds PD-1. In some embodiments, the PD-1 binding protein comprises at least one heavy chain variable domain and/or at least one light chain variable domain. In some embodiments, the PD-1 binding protein comprises at least three CDRs or at least six CDRs. In some embodiments, the PD-1 binding protein comprises a heavy chain variable domain comprising three CDRs and a light chain variable domain comprising three CDRs. In some embodiments, the PD-1 binding protein comprises a VH-FR4 or a modified VH-FR4; a VH-FR1 or a modified VH-FR1; and/or a VL-FR3 or modified VL-FR3. In addition, as more fully outlined herein, the variable heavy and variable light domains of the PD-1 binding protein can be on the same or separate polypeptide chains.

There are numerous immunoglobulin binding regions contemplated as components of the PD-1 binding proteins provided herein. In some embodiments, the immunoglobulin binding region is derived from an immunoglobulin binding region, such as, e.g., an antibody paratope capable of binding an extracellular part of PD-1. In some embodiments, the immunoglobulin binding region is an intact antibody and/or comprises an Fc region. In some embodiments, the PD-1 binding protein does not comprise an Fc region or any constant domain of an antibody. In some embodiments, the PD-1 binding protein is a recombinantly produced antibody, monoclonal antibody, multiclonal antibody, chimeric antibody, humanized antibody, primatized antibody, CDR-grafted antibody, human antibody (including recombinantly produced human antibodies), multispecific antibody (e.g. bispecific antibody), monovalent antibody, multivalent antibody, synthetic antibody, and antigen binding fragment or derivative of an antibody, such as, e.g., an antibody variable fragment (Fv), single-chain variable fragment (scFv), scFv-Fc fusion, single chain Fv-CFB minibody, bispecific tandem scFv fragment, multimerizing scFv fragment (diabody, triabody, tetrabody), Fd fragment, Fab fragment, F(ab') fragment, bivalent F(ab')2 fragment, single-domain antibody fragment (sdAb) or Nanobody®, bivalent Nanobody®, bispecific Nanobody®, bivalent minibody, bispecific minibody, autonomous VH domain, VHH, bispecific tandem VHH fragment, VNAR fragment, Fc antigen binding fragment (Fcab), isolated complementary determining region 3 (CDR3) fragment, constrained framework region 3, framework region 4 (FR3-CDR3-FR4) polypeptide, dimeric CH2 domain fragment (CH2D), heavy-chain antibody domain derived from a camelid VHH fragment or VH domain fragment, a heavy-chain antibody domain derived from a cartilaginous fish; or any other immunoreactive molecule or genetically manipulated counterparts of any of the foregoing which retain binding functionality.

In some embodiments, the immunoglobulin binding region of the PD-1 binding protein is selected from the group which includes single-chain variable (scFv) fragments, nanobodies, antibody variable (Fv) fragments, antigen-binding fragments (Fabs), single chain Fv-CH3 minibodies, scFv-Fc fusions, multimerizing scFv fragments (diabodies, triabodies, tetrabodies), disulfide stabilized antibody variable (Fv) fragments, disulfide stabilized antigen-binding (Fab) fragments consisting of the VL, VH, CL and CH1 domains, intact antibodies, bivalent nanobodies, bivalent minibodies, bivalent F(ab')2 fragments (Fab dimers), bispecific tandem scFv fragments, bispecific nanobodies, bispecific minibodies, and any genetically manipulated counterparts of the foregoing that retain its paratope and binding function, such as, e.g., wherein the relative orientation or order of the heavy and light chains is reversed or flipped.

Conventional antibodies consist of four polypeptide chains, two identical heavy chains and two identical light chains connected by disulfide bonds. The variable regions or variable domains of an antibody are the regions of the heavy and/or light chain that are involved in binding the antibody to antigen. The amino-terminal portion of each chain comprises a variable region of about 100 to 110 or more amino acids primarily responsible for antigen recognition, generally referred to in the art and herein as the "Fv domain" or "Fv region." In the variable region, three loops are gathered for each of the V domains of the heavy chain and light chain to form an antigen-binding site. Each of the loops is referred to as a CDR, in which the variation in the amino acid sequence is most significant. "Variable" refers to the fact that some segments of the variable region differ extensively in sequence among antibodies. Variability within the variable region is not evenly distributed. Instead, the V regions consist of relatively invariant stretches called framework regions (FRs) of about 15 to 30 amino acids separated by shorter regions of extreme variability called "hypervariable regions" that are each about 9 to 15 amino acids long or longer.

The variable domains of an antibody heavy chain and light chain generally have similar structures, with each domain comprising four conserved framework regions (FRs) and three hypervariable regions (HVRs) such that the framework region is interrupted by three CDRs or "antigen binding regions" (ABRs). The framework regions serve to align the CDRs or ABRs for specific binding to an epitope of an antigen. The CDRs or ABRs contribute to the formation of the antigen-binding, or more specifically, epitope binding site of antibodies and antibody derivatives. From amino- to carboxy-terminus, both VH and VL domains comprise the following FR and CDR regions or ABR regions in the following order: FR1-CDR1-FR2-CDR2-FR3-CDR3-FR4; or, similarly, FR1-ABR1-FR2-ABR2-FR3-ABR3-FR4.

The PD-1 binding proteins of the disclosure each comprise at least one immunoglobulin antigen binding region such that the PD-1 binding protein binds PD-1. In some embodiments, the antigen binding region comprises at least one heavy chain variable domain and at least one light chain variable domain, whether within a single polypeptide or separate polypeptide chains.

As used herein, "antigen binding domain" or "ABD" refers to a set of three or six CDRs that, when present as part of a PD-1 binding protein, specifically binds a PD-1 antigen. As is known in the art, these CDRs are generally present as a first set of variable heavy CDRs (vhCDRs or HCDRs) and a second set of variable light CDRs (vlCDRs or LCDRs), each comprising three CDRs: HCDR1, HCDR2, HCDR3 for the heavy chain and LCDR1, LCDR2, and LCDR3 for the light chain. As is understood in the art, the CDRs are separated by framework regions in each of the heavy variable and light variable regions.

In another aspect, provided herein is a PD-1 binding protein comprising at least three or six CDRs. In some embodiments, the PD-1 binding protein comprises an immunoglobulin heavy chain variable region (VH) and/or an immunoglobulin light chain variable region (VL). In some further embodiments, the PD-1 binding protein comprises a VH comprising three CDRs (HCDRs) and/or an immunoglobulin light chain variable region (VL) comprising three CDRs (LCDRs). In some embodiments, the immunoglobulin heavy chain variable region (VH) comprises a heavy chain framework 4 region (VH-FR4). In some further embodiments, the VH-FR4 further comprises an amino acid residue substitution relative to a reference sequence, such as, e.g., the heavy chain sequence of nivolumab (SEQ ID NO: 23) or any one of SEQ ID NOs: 23-24 and 27. In some embodiments, the immunoglobulin heavy chain variable region (VH) comprises a heavy chain framework 1 region (VH-FR1). In some further embodiments, the VH-FR1 further comprises an amino acid residue substitution relative to a reference sequence, such as, e.g., the heavy chain sequence of nivolumab (SEQ ID NO: 23) or any one of SEQ ID NOs: 23-24 and 27. In some embodiments, the immunoglobulin light chain variable region (VL) comprises a light chain framework 3 region (VH-FR3). In some further embodiments, the VH-FR3 further comprises an amino acid residue substitution relative to a reference sequence, such as, e.g., the light chain sequence of nivolumab (SEQ ID NO: 29) or any one of SEQ ID NOs: 30-32. In some further embodiments, the PD-1 binding protein comprises: (a) a heavy chain variable domain (VH) comprising: 1) a HCDR1 comprising the sequence of SEQ ID NO: 2; 2) a HCDR2 comprising the sequence of SEQ ID NO: 3; and 3) a HCDR3 comprising the sequence of SEQ ID NO: 4; (b) a light chain variable domain (VL) comprising: 1) a LCDR1 comprising the sequence of SEQ ID NO: 5; 2) a LCDR2 comprising the sequence of SEQ ID NO: 6; and 3) a LCDR3 comprising the sequence of SEQ ID NO: 7; and (c) any combination of a heavy chain framework 1 region (VH-FR1) comprising SEQ ID NO: 26, a heavy chain framework 4 region (VH-FR4) comprising one of SEQ ID NOs: 28 and 43-44, and a light chain framework 3 region (VL-FR3) comprising SEQ ID NO: 32.

In some embodiments, the PD-1 binding protein comprises: a) a heavy chain variable domain (VH) comprising: 1) a HCDR1 comprising the sequence of SEQ ID NO: 2; 2) a HCDR2 comprising the sequence of SEQ ID NO: 3; and 3) a HCDR3 comprising the sequence of SEQ ID NO: 4; and b) a light chain variable domain (VL) comprising: 1) a LCDR1 comprising the sequence of SEQ ID NO: 5; 2) a LCDR2 comprising the sequence of SEQ ID NO: 6; and 3) a LCDR3 comprising the sequence of SEQ ID NO: 7. In some further embodiments, the immunoglobulin heavy chain region comprises a heavy chain framework 4 region (VH-FR4) comprising an amino acid residue substitution relative to a reference sequence, such as, e.g., the heavy chain sequence of nivolumab (SEQ ID NO: 23) or any one of SEQ ID NOs: 23-24 and 27. In some further embodiments, the immunoglobulin heavy chain region comprises a heavy chain framework 1 region (VH-FR1) comprising an amino acid residue substitution relative to a reference sequence, such as, e.g., the heavy chain sequence of nivolumab (SEQ ID NO: 23) or any one of SEQ ID NOs: 23-24 and 27. In some further embodiments, the immunoglobulin light chain region comprises a light chain framework 3 region (VL-FR3) comprising an amino acid residue substitution relative to a reference sequence, such as, e.g., the light chain sequence of nivolumab (SEQ ID NO: 26) or any one of SEQ ID NOs: 29-31. In some embodiments, the PD-1 binding protein binds to PD-1 with high affinity, such as, e.g., capable of exhibiting a $K_D$ of at least about $10^{-7}$ M, at least about $10^{-8}$ M, and/or at least about $10^{-9}$ M. In some embodiments, the PD-1 binding protein binds to PD-1 and inhibits a function(s) of PD-1, such as, e.g. signaling via a ligand like PD-L1 or PD-L2. In some further embodiments, the PD-1 is human PD-1. In some further embodiments, the PD-1 binding protein comprises the polypeptide sequence of any one of SEQ ID NOs: 8-21. In some further embodiments, the PD-1 binding protein comprises or consists of the polypeptide sequence of any one of SEQ ID NOs: 10-15 and 18-22.

In some embodiments, the PD-1 binding protein comprises: a) a heavy chain variable domain (VH) comprising: 1) a HCDR1 comprising the sequence of SEQ ID NO: 2; 2)

TABLE 1

Immunoglobulin Amino Acid Residue Changes Relative to Reference Sequences.
The CDRs are in bold type. The mutations are underlined.

| | immunoglobulin polypeptide sequence |
|---|---|
| nivolumab HV (SEQ ID NO: 24) V5, L108, T110 | QVQLVESGGGVVQPGRSLRLDCKASGITFSNSGMHWVRQAP GKGLEWVAVIWYDGSKRYYADSVKGRFTISRDNSKNTLFLQ MNSLRAEDTAVYYCATNDDYWGQGTLVTVSS |
| anti-PD-1dm HV (SEQ ID NO: 8) L108G, T110R | VQLVESGGGVVQPGRSLRLDCKASGITFSNSGMHWVRQAPG KGLEWVAVIWYDGSKRYYADSVKGRFTISRDNSKNTLFLQM NSLRAEDTAVYYCATNDDYWGQGTGVRVSS |
| anti-PD-1tm HV (SEQ ID NO: 16) V5K, L108G, T110R | VQLKESGGGVVQPGRSLRLDCKASGITFSNSGMHWVRQAPG KGLEWVAVIWYDGSKRYYADSVKGRFTISRDNSKNTLFLQM NSLRAEDTAVYYCATNDDYWGQGTGVRVSS |
| nivolumab HV FR4 (SEQ ID NO: 27) | WGQGTLVTVSS |
| PD-1dm HV FR4 (SEQ ID NO: 28) | WGQGTGVRVSS |
| nivolumab HV FR1 (SEQ ID NO: 25) | QVQLVESGGGVVQPGRSLRLDC |
| PD-1tm HV FR1 (SEQ ID NO: 26) | QVQLKESGGGVVQPGRSLRLDC |
| nivolumab LV (SEQ ID NO: 30) I53 | EIVLTQSPATLSLSPGERATLSCRASQSVSSYLAWYQQKPGQA PRLLIYDASNRATGIPARFSGSGSGTDFTLTISSLEPEDFAVYYC QQSSNWPRTFGQGTKVEIK |
| anti-PD-1tm LV (SEQ ID NO: 17) I53R | EIVLTQSPATLSLSPGERATLSCRASQSVSSYLAWYQQKPGQA PRLLIYDASNRATGRPARFSGSGSGTDFTLTISSLEPEDFAVYY CQQSSNWPRTFGQGTKVEIKR |
| nivolumab LV FR3 (SEQ ID NO: 31) | GIPARFSGSGSGTDFTLTISSLEPEDFAVYYC |
| PD-1tm LV FR3 (SEQ ID NO: 32) | GRPARFSGSGSGTDFTLTISSLEPEDFAVYYC |

Table 1 shows variable domain sequences from nivolumab and some embodiments of the PD-1 binding proteins provided herein. In some embodiments, the PD-1 binding proteins differ from nivolumab as shown in Table 1. For example as shown in SEQ ID NO: 8 above, the PD-1 binding protein may comprise relative to positions 108 and 110 in the heavy chain variable domain SEQ ID NO: 24 respectively a glycine and arginine residue instead of a leucine and threonine residue. As shown in Table 1, position 108 is six amino acid residues carboxy-terminal to the last amino acid residue of H-CDR-3 (NDDY (SEQ ID NO: 4)) and position 110 is eight amino acid residues carboxy-terminal to the last amino acid residue of the H-CDR-3. For example, the PD-1 binding protein may comprises relative to position 5 in SEQ ID NO: 24 a lysine residue instead of a valine residue, as show in SEQ ID NO: 16. As shown in Table 1, position 5 is positioned four amino acid residues carboxyl-terminal from the first amino acid of the VH-FR1 and the entire heavy chain variable region domain, and position 5 is positioned 26 amino acid residues amino-terminal from the first amino acid of the H-CDR-1.

As shown in Table 1, the PD-1 binding protein may comprise relative to position 58 in the light chain variable domain SEQ ID NO: 30 an arginine residue instead of an isoleucine residue. Position 58 in SEQ ID NO: 30 is second amino acid carboxy-terminal from the last residue of L-CDR-2.

a HCDR2 comprising the sequence of SEQ ID NO: 3; and 3) a HCDR3 comprising the sequence of SEQ ID NO: 4; and b) a light chain variable domain (VL) comprising: 1) a LCDR1 comprising the sequence of SEQ ID NO: 5; 2) a LCDR2 comprising the sequence of SEQ ID NO: 6; and 3) a LCDR3 comprising the sequence of SEQ ID NO: 7. In some further embodiments, the PD-1 binding protein comprises the polypeptide sequence of any one of SEQ ID NOs: 10-15 or a sequence having at least 95%, at least 96%, at least 97%, at least 98%, or at least 99% amino acid identity thereto so long as the HCDR1 comprises SEQ ID NO: 2; 2) the HCDR2 comprises SEQ ID NO: 3; 3) the HCDR3 comprises SEQ ID NO: 4; 4) the LCDR1 comprises SEQ ID NO: 5; the LCDR2 comprises SEQ ID NO: 6; and 3) the LCDR3 comprises SEQ ID NO: 7; and so long as the VH comprises an arginine at position 110 relative to SEQ ID NO: 23 or 24 and/or an arginine residue positioned eight amino acid residues carboxy-terminal to the last amino acid residue of the HCDR3 (e.g. R110). In some further embodiments, the PD-1 binding protein comprises the polypeptide sequence of any one of SEQ ID NOs: 10-15 or a sequence having at least 95%, at least 96%, at least 97%, at least 98%, or at least 99% amino acid identity thereto so long as the HCDR1 comprises SEQ ID NO: 2; 2) the HCDR2 comprises SEQ ID NO: 3; 3) the HCDR3 comprises SEQ ID NO: 4; 4)

the LCDR1 comprises SEQ ID NO: 5; the LCDR2 comprises SEQ ID NO: 6; and 3) the LCDR3 comprises SEQ ID NO: 7; and so long as the VH comprises a glycine at position 108 and an arginine at position 110 relative to SEQ ID NO: 23 or 24, or a glycine residue positioned six amino acid residues carboxy-terminal to the last amino acid residue of the HCDR3 (e.g. G108) and an arginine residue positioned eight amino acid residues carboxy-terminal to the last amino acid residue of the HCDR3 (e.g. R110). In some further embodiments, the PD-1 binding protein has a VH comprising or consisting of the sequence of SEQ ID NO: 8 and/or a VL comprising or consisting of the sequence of SEQ ID NO: 9. In some further embodiments, the PD-1 binding protein comprises or consists of the polypeptide sequence of any one of SEQ ID NOs: 10-15.

In some embodiments, the PD-1 binding protein comprises: a) a heavy chain variable domain (VH) comprising: 1) a HCDR1 comprising the sequence of SEQ ID NO: 2; 2) a HCDR2 comprising the sequence of SEQ ID NO: 3; and 3) a HCDR3 comprising the sequence of SEQ ID NO: 4; and b) a light chain variable domain (VL) comprising: 1) a LCDR1 comprising the sequence of SEQ ID NO: 5; 2) a LCDR2 comprising the sequence of SEQ ID NO: 6; and 3) a LCDR3 comprising the sequence of SEQ ID NO: 7. In some further embodiments, the PD-1 binding protein comprises the polypeptide sequence of any one of SEQ ID NOs: 10-15 and 18-22 or a sequence having at least 95%, at least 96%, at least 97%, at least 98%, or at least 99% amino acid identity thereto so long as the HCDR1 comprises SEQ ID NO: 2; 2) the HCDR2 comprises SEQ ID NO: 3; 3) the HCDR3 comprises SEQ ID NO: 4; 4) the LCDR1 comprises SEQ ID NO: 5; the LCDR2 comprises SEQ ID NO: 6; and 3) the LCDR3 comprises SEQ ID NO: 7; and so long as the VH comprises a glycine at position 108 and an arginine at position 110 relative to SEQ ID NO: 23 or 24, or a glycine residue positioned six amino acid residues carboxy-terminal to the last amino acid residue of the HCDR3 (e.g. G108) and an arginine residue positioned eight amino acid residues carboxy-terminal to the last amino acid residue of the HCDR3 (e.g. R110). In some further embodiments, the PD-1 binding protein comprises a sequence having at least 95%, at least 96%, at least 97%, at least 98%, or at least 99% amino acid identity to any one of SEQ ID NOs: 10-15 and 18-22 so long as the HCDR1 comprises SEQ ID NO: 2; 2) the HCDR2 comprises SEQ ID NO: 3; 3) the HCDR3 comprises SEQ ID NO: 4; 4) the LCDR1 comprises SEQ ID NO: 5; the LCDR2 comprises SEQ ID NO: 6; and 3) the LCDR3 comprises SEQ ID NO: 7; and so long as the VH comprises a lysine at position 5, a glycine at position 108, and/or an arginine at position 110 relative to SEQ ID NO: 23 or 24; or a lysine residue positioned 26 amino acid residues amino-terminal from the first amino acid of the HCDR1, a glycine residue positioned six amino acid residues carboxy-terminal to the last amino acid residue of the HCDR3 (e.g. G108), and/or an arginine residue positioned eight amino acid residues carboxy-terminal to the last amino acid residue of the HCDR3 (e.g. R110). In some further embodiments, the PD-1 binding protein comprises a sequence having at least 95%, at least 96%, at least 97%, at least 98%, or at least 99% amino acid identity to SEQ ID NOs: 10-15 and 18-22 so long as the HCDR1 comprises SEQ ID NO: 2; 2) the HCDR2 comprises SEQ ID NO: 3; 3) the HCDR3 comprises SEQ ID NO: 4; 4) the LCDR1 comprises SEQ ID NO: 5; the LCDR2 comprises SEQ ID NO: 6; and 3) the LCDR3 comprises SEQ ID NO: 7; and so long as the VH comprises a lysine at position 5, a glycine at position 108, and/or an arginine at position 110 relative to SEQ ID NO: 23 or 24 and/or the VL comprises an arginine at position 58 relative to SEQ ID NO: 29 or 30; or so long as the VH comprises a lysine residue positioned 26 amino acid residues amino-terminal from the first amino acid of the HCDR1 (e.g. K5), a glycine residue positioned six amino acid residues carboxy-terminal to the last amino acid residue of the HCDR3 (e.g. G108), and/or an arginine residue positioned eight amino acid residues carboxy-terminal to the last amino acid residue of the HCDR3 (e.g. R110), and/or so long as the VL comprises an arginine residue positioned one amino acid residue carboxy-terminal to the last amino acid residue of the LCDR2 (e.g. R58). In some further embodiments, the PD-1 binding protein has a VH comprising or consisting of the sequence of SEQ ID NO: 8 or 16 and/or a VL comprising or consisting of the sequence of SEQ ID NO: 9 or 17 or the light chain variable fragment sequence of nivolumab (SEQ ID NO: 9). In some further embodiments, the PD-1 binding protein has a VH comprising or consisting of the sequence of SEQ ID NO: 8 or 16 and/or a VL comprising or consisting of the sequence of SEQ ID NO: 9 or 17 or the light chain variable fragment sequence of nivolumab (SEQ ID NO: 9).

In some embodiments, the PD-1 binding protein comprises a polypeptide sequence having at least 95%, at least 96%, at least 97%, at least 98%, or at least 99% amino acid identity to any one of SEQ ID NOs: 10-15 and 18-22 so long as the HCDR1 comprises SEQ ID NO: 2; 2) the HCDR2 comprises SEQ ID NO: 3; 3) the HCDR3 comprises SEQ ID NO: 4; 4) the LCDR1 comprises SEQ ID NO: 5; the LCDR2 comprises SEQ ID NO: 6; and 3) the LCDR3 comprises SEQ ID NO: 7; and so long as the PD-1 binding protein comprises a VH comprising an amino acid substitution at position 5, 108, or 110 relative to SEQ ID NO: 23 or 24. In some further embodiments, the PD-1 binding protein comprises a VL comprising an amino acid substitution at position 58 relative SEQ ID NO: 29 or 30. In some further embodiments, the amino acid substitution relative to any one of SEQ ID NOs: 23-24 or 29-30, changes a residue having a hydrophobic and/or nonpolar side chain (R group) to a residue having a polar and/or charged side chain. In some further embodiments the amino acid substitution changes, relative to any one of SEQ ID NOs: 23-24 or 29-30, a valine, leucine, or isoleucine to an arginine, asparagine, aspartate, glutamate, glutamine, histidine, lysine, serine, threonine, or glycine; and typically to an arginine, aspartate, glutamate, histidine, or lysine. In some embodiments, the amino acid substitution changes a polar residue to a more polar residue. In some embodiments, the amino acid substitution changes an uncharged polar residue to a charged polar residue. In some further embodiments, the amino acid substitution changes a threonine to an arginine, aspartate, glutamate, histidine, or lysine; and typically to an arginine or lysine.

In some embodiments, the PD-1 binding protein has a VH comprising the sequence of SEQ ID NO: 8 and VL comprising the sequence of SEQ ID NO: 9 or 17. In some embodiments, the PD-1 binding protein has a VH consisting of the sequence of SEQ ID NO: 8 and VL consisting of the sequence of SEQ ID NO: 9 or 17.

In some embodiments, the PD-1 binding protein has a VH comprising the sequence of SEQ ID NO: 16 and VL comprising the sequence of SEQ ID NO: 9 or 17. In some embodiments, the PD-1 binding protein has a VH consisting of the sequence of SEQ ID NO: 16 and VL consisting of the sequence of SEQ ID NO: 9 or 17.

In some embodiments, the PD-1 binding protein comprises the polypeptide sequence of any one of SEQ ID NOs: 8-21. In some embodiments, the PD-1 binding protein comprises or consists of the polypeptide sequence of any one of SEQ ID NOs: 10-15 and 18-22.

In some embodiments, the PD-1 binding protein comprises a linker. In some embodiments, the linker comprises or consists of the sequence of any one of SEQ ID NOs: 35-39. In some embodiments, the PD-1 binding protein comprises a linker (a first linker) fused between the VL and VH polypeptides, wherein the linker is a peptide of about 1 to about 40 amino acids. In some further embodiments, the linker comprises at least 12 amino acid residues, optionally comprising the sequence of any one of SEQ ID NOs: 38-39. In some embodiments, the PD-1 binding protein comprises a linker that comprises or consists of the sequence of any one of SEQ ID NOs: 35-41, or a sequence having at least 85%, at least 90%, at least 95%, at least 96%, at least 97%, at least 98%, or at least 99% amino acid sequence identity thereto. In further aspects, the linker comprises the sequence (Gly4Ser (SEQ ID NO: 36))n (SEQ ID NO: 47), wherein n is equal to 1, 2, 3, 4, or 5, and optionally with n equal to at least 3 in some embodiments.

In some embodiments, the PD-1 binding protein comprises, from its amino (N)- to carboxy (C)-terminus, VH-linker-VL. In other embodiments, the PD-1 binding protein comprises, from its amino (N)- to carboxy (C)-terminus, VL-linker-VH. In some embodiments, the PD-1 binding protein comprises, from its amino (N)- to carboxy (C)-terminus, VH::linker::VL. In other embodiments, the PD-1 binding protein comprises, from its amino (N)- to carboxy (C)-terminus, VL::linker::VH.

In some embodiments, the PD-1 binding protein further comprises a polypeptide fused carboxy-terminal (C-term) to the VL polypeptide, referred to herein as "C-term-polypeptide". In some embodiments, the PD-1 binding protein comprises, from its amino (N)- to carboxy (C)-terminus, VH-linker-VL-(C-term-polypeptide). In some further embodiments, the C-term-polypeptide is about 10 to about 400 amino acids in length. In some embodiments, the C-term-polypeptide is from about 30 to about 300 amino acids in length. In some embodiments, the C-term-polypeptide is from about 50 to about 200 amino acids in length. In some embodiment, the C-term-polypeptide is fused to the VL polypeptide indirectly via one or more linkers, such as, e.g., a proteinaceous linker described herein.

In some embodiments, the PD-1 binding protein comprises a polypeptide wherein the carboxy-terminal (C-term) amino acid residue is a cysteine. In some further embodiments, the polypeptide comprises or consists of SEQ ID NO: 11 or 19.

In some embodiments, the PD-1 binding protein comprises a carboxy-terminal (C-term) polypeptide selected from any one of SEQ ID NOs: 33-35 and 40.

In some embodiments, the PD-1 binding protein comprises an amino-terminal (N-term) polypeptide selected from any one of SEQ ID NOs: 33-35 and 41.

In some embodiments, the PD-1 binding protein does not comprise SEQ ID NO: 42 or does not comprise SEQ ID NO: 35 or 40 further having a substitution of phenylalanine (F) to glycine (G).

In some embodiments, the PD-1 binding protein is monomeric and/or has a size less than 40 kDa, 35 kDa, 30 kDa, or 28 kDa.

In some embodiments, the PD-1 protein further comprises a peptide or polypeptide tag, such as, e.g., a tag or label known in the art and/or described herein. In some embodiments, the peptide or polypeptide tag is fused to the PD-1 protein. The label or tag may include a tag recognized by another antigen binding moiety or an antibody, such as a FLAG tag or His tag or the label may be a label detected via an assay or fluorescence such as luciferase, fluorescent proteins such as GFP (e.g., SEQ ID NO: 33) or other means of detection known to those skilled in the art. The tag may include an engineered O(6)-alkylguanine-DNA alkyltransferase (AGT), such as, e.g., a SNAP tag providing for convenient attachment of a cargo, e.g., a SNAP tag substrate like a fluorescent dye.

In some embodiments, the PD-1 binding protein further comprises a radioisotope.

In some embodiments, the PD-1 binding protein is a homodimer or monomeric.

In some embodiments, the PD-1 binding protein is monovalent or multivalent (e.g. bivalent).

In some embodiments, the PD-1 binding protein has one or more post-translational modifications of at least one polypeptide component.

In some embodiments, the PD-1 binding protein does not comprise a functional Fc region of an antibody.

In additional aspects, the PD-1 binding protein is immobilized to a solid support, such as a solid substrate known in the art and/or described herein (e.g. beads, polymers, microarrays, or microtiter plates).

For some embodiments, the PD-1 binding protein binds to PD-1 with high affinity, such as, e.g., capable of exhibiting a Kd of at least about $10^{-7}$ M, at least about $10^{-8}$ M, at least about $10^{-9}$ M, at least about $10^{-10}$ M, at least about $10^{-11}$ M, at least about $10^{-12}$ M, at least about $10^{-13}$ M, and/or at least about $10^{-14}$ M. In some further embodiments, the PD-1 is human PD-1. In some embodiments, the human PD-1 comprises or consists of SEQ ID NO: 1. For some embodiments, the PD-1 binding proteins binds to an epitope of PD-1 that is conserved among PD-1 proteins from different species (e.g. human and non-human primates). For some embodiments, the PD-1 binding proteins binds human PD-1 and/or cynomolgus macaque PD-1.

For some embodiments, the PD-1 binding protein is capable of binding PD-1 present on a cellular surface (such as, e.g., PD-1 expressing cell or PD-1 positive cell) and/or an extracellular part of PD-1 (such as, e.g., an epitope present within the extracellular domain of PD-1). For some further embodiments, the PD-1 binding protein is capable of binding a polypeptide comprising amino acids 1-167 of SEQ ID NO: 1, amino acids 29-53 of SEQ ID NO: 1, or amino acids 85-103 of SEQ ID NO: 1.

For some embodiments, the PD-1 binding protein binds to PD-1 and inhibits a function(s) of PD-1, such as, e.g. signaling via a ligand(s) like PD-L1 and/or PD-L2. For some embodiments, the PD-1 binding protein binds to PD-1 and inhibits a function(s) of PD-1, such as, e.g. signaling via a B7 Family member, such as, e.g., B7-H1, B7-DC, B7-H2, B7-H3, B7-H4, B7-H5, B7-H6, and/or B7-H7. In some further embodiments, the PD-1 is human PD-1. In some embodiments, the human PD-1 comprises or consists of SEQ ID NO: 1.

In some embodiments, the PD-1 binding protein is capable of exhibiting a half-maximal inhibitory concentration (IC50) of less than 80 nM, 60 nM, 50 nM, or 40 nM in a PD-1/PD-L1 TR-FRET interaction assay; or a half-maximal effective concentration (EC50) of less than 100 nM or 50 nM in a PD-1/PD-L1 interaction cell-based assay using Jurkat cells and PD-L1 expressing CHO cells.

In other aspects, provided herein are compositions comprising a PD-1 binding protein described herein and a pharmaceutically acceptable carrier or excipient, such as, e.g., as described in (Remington's Pharmaceutical Sciences 16th edition, Osol, A. Ed. (1980) and/or known in the art.

Preferably, the pharmaceutically acceptable carrier is a liquid suitable for intravenous administration and/or injection of the PD-1 binding protein.

In further aspects, provided herein are nucleic acids encoding the PD-1 binding proteins, as well as an expression vectors comprising an aforementioned nucleic acid, and host cells comprising an aforementioned nucleic acid and/or expression vector herein. Provided herein are methods comprising culturing a host cell comprising a nucleic acid and/or expression vector described herein under conditions wherein a PD-1 binding protein is expressed, and recovering, extracting or isolating the PD-1 binding protein.

In a further aspect, provided herein is a PD-1 binding protein further comprising a detection-promoting agent. In another aspect, provided herein is a diagnostic composition comprising a PD-1 binding protein comprising a detection-promoting agent and an acceptable carrier or excipient. The ability to conjugate detection-promoting agents known in the art to a PD-1 binding protein provides useful compositions for the detection of certain cells, such as, e.g., PD-1 expressing cancer, tumor, immune, and/or infected cells. These diagnostic embodiments of the PD-1 binding protein may be used for information gathering via various imaging techniques and assays known in the art. For example, diagnostic embodiments of the PD-1 binding proteins of the invention may be used for information gathering via imaging of individual cancer cells, immune cells (e.g. a T cell, NK cell, B cell, tumor infiltrating immune cell (e.g. APC), myeloid derived immune cell (e.g. MDSC), or macrophage), and/or infected cells in a patient or biopsy sample.

Linkers

Individual PD-1 immunoglobulin regions and/or components of the PD-1 binding proteins (e.g. a cargo or detection-promoting agent) of the instant disclosure may be suitably linked to each other via one or more linkers well known in the art and/or described herein. Individual polypeptide subcomponents of the binding regions, e.g. heavy chain variable regions ($V_H$), light chain variable regions ($V_L$), CDR, and/or ABR regions, may be suitably linked to each other via one or more linkers well known in the art and/or described herein. Proteinaceous components of the invention, e.g., multi-chain binding regions, may be suitably linked to each other or other polypeptide components via one or more linkers well known in the art. Proteinaceous components, e.g., a peptide tag or fluorescent protein, may be suitably linked to another component of the invention via one or more linkers, such as a proteinaceous linker, which are well known in the art.

Suitable linkers are generally those which allow each polypeptide component of the present invention to fold with a three-dimensional structure very similar to the polypeptide components produced individually without any linker or other component. Suitable linkers include single amino acids, peptides, polypeptides, and linkers lacking any of the aforementioned, such as various non-proteinaceous carbon chains, whether branched or cyclic.

By "linker" herein is meant a domain linker that joins two protein domains together, such as are used in scFv and/or other protein and protein fusion structures. Generally, there are a number of suitable linkers that can be used, including traditional peptide bonds, generated by recombinant techniques that allows for recombinant attachment of the two domains with sufficient length and flexibility to allow each domain to retain its biological function. The linker should have a length that is adequate to link two molecules in such a way that they assume the correct conformation relative to one another so that they retain the desired activity.

Proteinaceous linkers may be selected based upon the properties desired. Proteinaceous linkers may be chosen by the skilled worker with specific features in mind, such as to optimize one or more of the PD-1 binding protein's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability. The skilled worker may use databases and linker design software tools when choosing linkers. In some instances, certain linkers may be chosen to optimize expression. Certain linkers may be chosen to promote intermolecular interactions between identical polypeptides or proteins to form homomultimers such as homodimers.

In some embodiments, the linker is from about 1 to about 50 amino acids in length. In some embodiments, the linker is from about 1 to about 30 amino acids in length. In one embodiment, linkers of 1 to 20 amino acids in length may be used, with from about 5 to about 10 amino acids or 8 to 15 amino acids finding use in some embodiments. Commonly, proteinaceous linkers comprise a majority of amino acid residues with polar, uncharged, and/or charged residues, such as, e.g., serine, threonine, proline, glutamine, glycine, and alanine. A linker peptide may predominantly include the following amino acid residues: Gly, Ser, Ala, or Thr. Useful linkers include glycine-serine polymers, glycine-alanine polymers, alanine-serine polymers, and other flexible linkers.

While any suitable linker can be used, many embodiments utilize a glycine-serine polymer, including for example (GGGGS)n (SEQ ID NO: 47), where n is an integer of at least one (and generally from 3 to 5). "scFv linkers" generally include these glycine-serine polymers.

Linkers may be derived from an immunoglobulin heavy and/or light chains of any type or isotype. A linker sequences may include any sequence of any length of a CL/CH1 domain but not all residues of CL/CH1 domain; for example, the first 5-12 amino acid residues of a CL/CH1 domains. Linker sequences may also be derived from other proteins such as Ig-like proteins (e.g., TCR, FcR, or KIR), hinge region-derived sequences, and other natural sequences from other proteins.

Proteinaceous linkers may be chosen for incorporation into recombinant PD-1 binding proteins of the present invention. In some embodiments of the PD-1 binding protein is linked to a cargo via a linker using any number of means known to the skilled worker, including both covalent and noncovalent linkages.

In some embodiments, the VH and the VL of the PD-1 binding protein are on a single polypeptide chain but the linker between them is too short to allow intramolecular association, and thus a homodimer forms, that contains two anti-PD-1 binding regions (i.e. a bivalent homodimer PD-1 binding protein). In other embodiments, the linker between the VH and the VL is long enough to allow for monomeric scFv formation, and thus the PD-1 binding protein is monovalent.

Suitable linkers may be non-proteinaceous, such as, e.g. chemical linkers. Various non-proteinaceous linkers known in the art may be used to link immunoglobulin binding regions to each other or other components of the PD-1 binding proteins of the instant disclosure, such as linkers commonly used to conjugate immunoglobulin polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides. In addition, non-natural amino acid residues may be used with other functional side chains, such as ketone groups. Examples of non-proteinaceous chemical linkers include but are not limited to N-succinimidyl (4-iodoacetyl)-aminobenzoate, S-(N-succinimidyl) thioacetate (SATA), N-succinimidyl-oxycarbonyl-cu-methyl-α-(2-pyridyldithio) toluene (SMPT), N-succinimidyl4-(2-pyridyldithio)-pentanoate (SPP), succinimidyl4-(N-maleimidomethyl) cyclohexane carboxylate (SMCC or MCC), sulfosuccinimidyl (4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(−2-pyridyldithio)-proprionate (SPDP), succinimidyl 6(3(−(−2-pyridyldithio)-proprionamido) hexanoate, sulfosuccinimidyl 6(3(−(−2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanine]), sulfodichlorophenol, 2-iminothiolane, 3-(2-pyridyldithio)-propionyl hydrazide, Ellman's reagent, dichlorotriazinic acid, and S-(2-thiopyridyl)-L-cysteine.

Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers.

Suitable methods for linkage of the components of the PD-1 binding proteins may be by any method presently known in the art for accomplishing such, so long as the attachment does not substantially impede the binding capability of the immunoglobulin binding region to a PD-1 molecule, or when appropriate, an additional desired function as measured by an appropriate assay, including assays described herein, such as, e.g., PD-1 signaling inhibition or cargo attachment.

Variations of the PD-1 Binding Protein

In some embodiments, amino acid sequence variants of the PD-1 binding proteins of the instant disclosure are contemplated. For example, it may be desirable to improve the binding affinity and/or other biological properties of a PD-1 binding protein. Amino acid sequence variants of PD-1 binding protein may be prepared by introducing appropriate modifications into the nucleotide sequence encoding the PD-1 binding protein or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., a certain PD-1 binding affinity and specificity level, a certain level of Kd, and/or a certain level of Koff.

In some embodiments, the PD-1 binding protein can comprise modifications and/or mutations that alter the properties of the PD-1 binding protein, such as those that increase half-life, decrease immunogenicity, increase or decrease cytotoxicity, alter glycosylation, and/or increase or decrease ADCC, CDC, antibody-dependent cell-mediated phagocytosis (ADCP), antigen crosslinking, PD-1 antagonism, PD-L1 antagonism, PD-L2 antagonism, PD-1 agonist activity, and/or cellular internalization, as is known in the art. In some embodiments, the PD-1 binding protein sequence is modified to provide for non-natural amino acid or radioisotope incorporation. In some embodiments, the PD-1 binding protein sequence is modified to provide for conjugation or fusion to a cargo or other moiety, e.g. site-specific attachment. In some embodiments, an immunoglobulin binding region of the PD-1 binding protein is chimeric, humanized, or camelized.

Also included herein are anti-PD-1 ABDs that have amino acid modifications in one or more of the CDRs and/or the framework regions. As outlined herein, in some embodiments the set of 6 CDRs can have from 0, 1, 2, 3, 4, 5 or 6 amino acid modifications (with amino acid substitutions finding particular use). The CDRs can have amino acid modifications (e.g. from 1, 2, 3, 4, 5 or 6 amino acid modifications in the set of CDRs (that is, the CDRs can be modified as long as the total number of changes in the set of 6 CDRs is less than 6 amino acid modifications, with any combination of CDRs being changed; e.g. there may be one change in vLCDR1, two in vHCDR2, none in vHCDR3, etc.). In some embodiments, each CDR has no more than a single amino acid substitution. In some embodiments, amino acid substitutions in the vHCDR3 are avoided. In some cases, the binding affinity for either or both of human and cyno PD-1 may be increased, while in other embodiments the binding affinity may be reduced. Suitable assays for testing whether an anti-PD-1 antigen binding domain that contains mutations as compared to the VH and VL sequences outlined herein are known in the art, such as Biacore assays.

In some embodiments, the anti-PD-1 ABDs outlined herein may also have amino acid modifications (again, with amino acid substitutions finding particular use) in the framework regions of either or both of the variable heavy and variable light framework regions, as long as the frameworks (excluding the CDRs) retain at least about 80%, about 85% or about 90% identity to a sequence provided herein. Thus, for example, the identical CDRs as described herein can be combined with different framework sequences from human germline sequences, as long as the framework regions retain at least 80%, at least 85% or at least 90% identity to a sequence provided herein.

In another aspect, provided herein are PD-1 immunoglobulin binding regions that include variants of the above listed heavy chain variable and light chain variable regions. The heavy chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VH" sequences herein, and/or contain from 1, 2, 3, 4, 5, 6, 7, 8, 9, 10 amino acid changes. The light chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VL" sequences herein, and/or contain 1, 2, 3, 4, 5, 6, 7, 8, 9, 10 amino acid changes. In these embodiments, the invention includes these variants as long as the antigen binding domains still bind to human PD-1. Suitable assays for testing whether an anti-PD-1 antigen binding domain that contains mutations as compared to the VH and VL sequences outlined herein are known in the art, such as Biacore assays.

Any of the aforementioned immunoglobulin binding regions or PD-1 binding proteins may be suitable for use in the methods herein or may be modified to create one or more PD-1 binding proteins of the instant disclosure. Any of the above antibody structures may be used as a component of a PD-1 binding protein of the instant disclosure as long as the PD-1 binding is capable of exhibiting binding to a PD-1 molecule characterized by a dissociation constant of $10^4$ to $10^{-13}$ M or less, preferably less than 200 nanomolar (nM).

In some embodiments, the nucleic acid encoding a PD-1 binding protein comprises one or more modifications. For example, the nucleic acid can encode a PD-1 binding protein comprising a secretory signal. In other cases, the nucleic acid can encode a PD-1 binding protein further comprising a detectable label such as a fluorophore, 5-carboxyfluorescein, radiolabel, green fluorescent protein (GFP) or a derivative thereof, or other detectable cargo (i.e. a detection-promoting agent). Other modifications appropriate for use with the PD-1 binding proteins provided herein include, without limitation, include a modification at the amino—(N) and/or carboxy—(C) terminus of a PD-1 binding protein described herein and as incorporated via the nucleic acid encoding the PD-1 binding protein.

II. PD-1 Binding Protein Function

The PD-1 binding proteins described herein have one or multiple uses, such as, e.g., for detecting or quantitating PD-1, labeling PD-1 expressing cells, inhibiting PD-1 function, and treating disorders involving PD-1 expressing cells. The PD-1 binding proteins of the instant disclosure have various biological activities, such as, e.g., inhibiting a PD-1 function(s), targeting and internalizing into a PD-1 expressing cell to deliver a cargo or detection-promoting agent, and/or killing a PD-1 expressing cell. The PD-1 binding proteins are useful, such as, e.g., as an immunologic adjuvant, for increasing or enhance immune responses, and/or as a component of an immunization or vaccination regimen. The PD-1 binding proteins are useful, such as, e.g., for monitoring patient responses to therapies, diagnosing PD-1 related conditions, and treating disorders involving PD-1 expressing cells, including cancers and autoimmune diseases.

Certain PD-1 binding proteins described herein are PD-1 signaling modulators. By inhibiting PD-1, certain PD-1 binding proteins described herein may modulate immune checkpoint mechanisms, T cell anergy, tolerance, and the tumor microenvironment, and, thus, may be useful in treating cancers or autoimmune diseases. PD-1 modulators may promote T cell functions and restore immune responses, such as, e.g., normal levels of T cell proliferation, cytokine production, and cytotoxic T cell activity, particularly in a tumor microenvironment and/or for tumor-infiltrating lymphocytes. PD-1 modulators may increase an immune response(s), promote anti-tumor activity(ies), and/or alter the balance of immune tolerance, including self and non-self tolerance, whether locally or systemically (e.g. via peripheral or central immune mechanisms), such as within a tumor microenvironment. By inhibiting PD-1, certain PD-1 binding proteins described herein may increase or enhance immune responses and, thus, may be useful as immunologic adjuvants, such as, e.g., to enhance a vaccination effect or immunization. For certain embodiments, an immunologic adjuvant effect may be a result of or may be monitored by an increase in the number of memory CD8+ T cells and/or central memory T cells in a subject upon administration of a PD-1 binding protein described herein. By activating PD-1, certain PD-1 binding proteins described herein may reduce or inhibit immune responses and, thus, may be useful for treating autoimmune diseases involving overactive immune responses, for reducing inflammation, and/or treating inflammatory diseases.

Methods of Characterizing PD-1 Binding Proteins: Functional Activity Assays

A PD-1 binding protein may be tested for various biological activities besides binding affinity using methods known in the art. A possible biological activity of a PD-1 binding protein of the instant disclosure may include, e.g., binding to different PD-1 molecules or epitopes, detecting PD-1 levels in samples or in vivo, stimulating ADCC, stimulating CDC, stimulating programmed cell death (e.g. apoptosis), stimulating ADCP, depletion/consumption of PD-1, and modulating PD-1 signaling (e.g. inhibition of signal transduction). Antibodies having such biological activity in vivo and/or in vitro are also provided. Due to the immunoglobulin component(s) of the PD-1 binding protein of the instant disclosure, certain biological activities may be considered to be "antibody" activities, and an antibody activity of a PD-1 binding protein can be determined by common methods known in the art.

A. PD-1 Binding Affinity, Epitope Mapping, and Binding Competition

A PD-1 binding protein's ability to bind a target PD-1 can be characterized by common methods known in the art. The PD-1 binding protein of the instant disclosure may "bind specifically" to a PD-1 protein. A PD-1 binding protein is considered to bind specifically if the PD-1 binding protein binds to the PD-1 target with a threshold level of binding activity. Binding affinity of an antibody can be characterized using the dissociation constant "Kd" or the association constant "Ka." Binding affinity may be determined using various techniques known in the art, for example, using an enzyme-linked immunosorbent assay (ELISA), isothermal titration calorimetry, Western blot, surface-plasmon resonance, protein display, fluorescent polarization, bio-layer interferometry, dual polarization interferometry, static light scattering, dynamic light scattering, analytical ultracentrifugation, flow cytometry, and other methods described herein. For some embodiments, the Kd is measured by using surface-plasmon resonance assays using a Biacore™ instrument (GE Healthcare, Chicago, IL, ET.S.A.) at 25° C. with immobilized antigen using standard techniques known to the skilled worker.

A PD-1 binding protein of the instant disclosure may specifically bind the PD-1 protein comprising or consisting of SEQ ID NO: 1 and/or a polypeptide comprising amino acids 1-167 of SEQ ID NO: 1. A PD-1 binding protein of the instant disclosure may bind with high affinity to the PD-1 protein comprising or consisting of SEQ ID NO: 1 and/or a polypeptide comprising amino acids 1-167 of SEQ ID NO: 1. A PD-1 binding protein of the instant disclosure may selectively bind the PD-1 protein comprising or consisting of SEQ ID NO: 1 and/or a polypeptide comprising amino acids 1-167 of SEQ ID NO: 1. A PD-1 binding protein of the instant disclosure may specifically bind a polypeptide comprising, consisting essentially of, or consisting of an amino acid sequence that is at least 75% (e.g. at least 80%, 85%, 90%, 91%, 92%, 93%, 94%, 95%, 96%, 97%, 98% or 99%) identical to SEQ ID NO: 1 and/or a polypeptide comprising amino acids 1-167 of SEQ ID NO: 1.

B. PD-1 Antagonistic Activity

In one embodiment, the PD-1 binding protein may act as an antagonist that blocks, reduces or inhibits the biological activity of PD-1. The binding of PD-1 by the PD-1 binding protein may prevent binding or association of the bound PD-1 with a binding partner such as a ligand (e.g. PD-L1 and/or PD-L2) or substrate, thereby interrupting a biological response that otherwise would result from the interaction of the molecules. For example, cell-based reporter assays for immune checkpoint activation known in the art may be used by the skilled worker to characterize a PD-1 binding protein. One example is a coculture cell assay using PD-1 effector cells (like Jurkat cells expressing PD-1) and PD-L1 expressing cells (like CHO-K1 cells expressing PD-L1 and a cell surface protein designed to activate cognate T-cell receptors (TCRs) in an antigen dependent manner) (see e.g., Promega, Madison, WI: "PD-1/PD-L 1 Blockade Bioassay Protocol"; and BPS Bioscience PD-1: PD-L1/L2 Screening Services, biochemical and cell-based profiling). PD-1 Signaling Axis Blockade, e.g. PD-L1/PD-1 Signaling Interference In one embodiment, the PD-1 binding protein may interfere with the PD-L1/PD-1 signaling axis, and thus may be used for inhibiting PD-1 signaling, such as, e.g., in applications involving immune checkpoint inhibition, anti-cancer immunotherapy, and autoimmune disease therapy. For some embodiments, the PD-1 binding protein exhibits EC50 values (e.g. 1 to 200 nM).

Blockade of the PD-L1/PD-1 signaling axis may promote epitope spreading by reducing CD8+ T cell fratricidal lysis of neighboring CD8+ T cells restricted to less immunodominant antigens (Haeryfar S and Schell, Cancer Immunol Immunother 67: 1669-72 (2018)), and T cell effector cells specific to certain less dominant neoantigens may be important for therapeutic effectiveness (see e.g. Braunlein E, Krackhardt A, Front Immunol 8: 1702 (2017)). The reduction in fratricide of CD8+ T-cells restricted to less immunodominant antigens may reinvigorate subdominant CD8+ T-cells responses that might contribute to antitumor immunity (Memamejadian A et al., J Immunol 199: 3348-59 (2017); Haeryfar S and Schell, Cancer Immunol Immunother 67: 1669-72 (2018)). Thus, PD-1 is a putative target for immunomodulatory agents for increasing immune responses to less dominant antigens, such as, e.g. locally in the tumor microenvironment.

C. PD-1 Agonist Activity

In another embodiment, the PD-1 binding protein may act as an agonist that stimulates or increases the biological activity of the PD-1. The binding of PD-1 by the PD-1 binding protein may facilitate binding or association of PD-1 to a binding partner such as a receptor or substrate, thereby promoting a biological response (e.g. increasing signal transduction). For example, cell-based reporter assays for immune checkpoint signaling known in the art may be used by the skilled worker to characterize agonist action of a PD-1 binding protein.

D. Cellular Internalizing Activity

A PD-1 binding protein's cellular internalization activity can be determined by common methods known in the art. For some embodiments, the PD-1 binding protein may have an internalizing function such that when the PD-1 binding protein binds to PD-1 on a cellular surface (e.g. PD-1 on the surface of a PD-1 expressing cell), the PD-1 binding protein will be internalized (along with any cargo) into the cell, e.g. a PD-1 expressing cell.

E. Delivery of Cargo into the Interior of Targeted Cells

Certain PD-1 binding proteins may be used as delivery vehicles for targeted delivery of cargos. Cargos include toxic payloads (e.g. a chemotherapeutic or radioisotope) and non-toxic cargos, such as, e.g. certain detection-promoting agents, enzymes, or polynucleotides. Some cytotoxic PD-1 binding proteins may be rendered non-cytotoxic, such as, e.g., via the addition of one or more amino acid substitutions known to the skilled worker (e.g. to an Fc region) to render the PD-1 binding protein more suitable in certain situations for delivery of a cargo to PD-1 expressing cell. Various types of cells and/or cell populations which express PD-1 to at least one cellular surface may be targeted by the PD-1 binding proteins described herein for receiving cargos.

F. Cytotoxic Activity to a PD-1 Expressing Cell Type

Certain PD-1 binding proteins may be used to kill a PD-1 expressing cell. For some embodiments, the PD-1 binding protein is cytotoxic but only after binding to cell surface PD-1 and internalizing into a PD-1 expressing cell. For some embodiments, the PD-1 binding protein is cytotoxic due to a cargo, e.g., a chemotherapeutic and/or radioisotope. For some embodiments, the PD-1 binding protein is cytotoxic due to its agonist or antagonist activity to PD-1, or its ligands. For some embodiments, the PD-1 binding protein is cytotoxic due to an antibody Fc region. For some embodiments, the PD-1 binding protein is cytotoxic due to its multivalent PD-1 binding and crosslinking activity.

The expression of the target PD-1 by a cell need not be native in order for cell targeting by a PD-1 binding protein, such as, e.g., for direct cell-kill, indirect cell-kill (including ADCC and/or CDC), delivery of a cargo, and/or information gathering. Cell surface expression of the target PD-1 biomolecule could be the result of an infection, the presence of a pathogen, and/or the presence of an intracellular microbial pathogen. Expression of a target biomolecule could be artificial such as, for example, by forced or induced expression after infection with a viral expression vector, see e.g. adenoviral, adeno-associated viral, and retroviral systems, after inoculation with a microbe, and/or after introduction of a malignant cell type (e.g. a tumor cell).

III. Methods

Provided herein are methods of using the PD-1 binding proteins described herein, variants thereof, and compositions of the aforementioned. The PD-1 binding proteins described herein have multiple uses, e.g., for detecting PD-1 and/or quantitating PD-1 levels, which can be used in various applications, such as diagnosing PD-1 related conditions, therapeutic strategy decisions, and monitoring patient responses to therapies. The PD-1 binding proteins described herein have multiple uses, e.g., for treating a disease or condition involving a PD-1 expressing cell, such as a cancer or autoimmune condition. The PD-1 binding proteins described herein have multiple uses, e.g., for increasing the effectiveness of a vaccine or immunization method, for treating cancer, for diagnosing resistance to a cancer therapeutic.

In some aspects, provided herein is a method of detecting PD-1, the method comprising (i) contacting a sample with a PD-1 binding protein described herein, and (ii) detecting the PD-1 binding protein. In some aspects, provided herein is a method of treatment comprising administering to a subject in need thereof a therapeutically effective amount of a PD-1 binding protein described herein or a composition thereof. In some aspects, provided herein is use of a PD-1 binding protein described herein for the treatment of disease, such as, e.g., a cancer or autoimmune disorder. In another aspect, provided herein is use of a PD-1 binding protein described herein or a polynucleotide encoding it and/or a composition of the aforementioned in the manufacture of a medicament.

A. PD-1 Detection and Quantitation

In some aspects, provided herein is a method of detecting PD-1, the method comprising (i) contacting a sample with a PD-1 binding protein described herein, and (ii) detecting the PD-1 binding protein. In some embodiments, the contacting step occurs in vitro. In some embodiments, the detecting step occurs in vitro. In some embodiments, the contacting step occurs in vivo. In some embodiments, the detecting step occurs in vivo. In some embodiments, the detection of PD-1 is indicative of the presence of an activated T cell in the sample.

For some embodiments, the method comprises the step of (a) contacting a biological sample with the PD-1 binding protein under conditions that allow binding of the PD-1 binding protein to a PD-1 molecule to form an immunocomplex; and the step of (b) detecting the immunocomplex to detect the presence of PD-1. In some embodiments, the PD-1 binding protein is immobilized to a solid support or substrate and the method further comprises after step (b), the step of (c) separating an immunocomplex of immobilized PD-1 binding protein bound to PD-1 from a biological sample. In some embodiments, the biological sample is taken from a human subject that has been treated with an immune checkpoint inhibitor and/or PD-1 targeted therapy, such as, e.g. an anti-PD-1 antibody (e.g. nivolumab, pembrolizumab, or cemiplimab), anti-PD-L1 antibody, anti-B7-1 antibody, anti-PD-L2 antibody, anti-CTLA-4 antibody, and/or anti-LAG-3 antibody.

For some embodiments, the method comprises (a) contacting a biological sample with a capture agent, wherein the capture agent is a composition comprising a PD-1 binding protein as provided herein, thereby forming an immunocomplex; (b) contacting the immunocomplex from (a) with a detectable antibody that binds to the PD-1 binding protein; and (c) measuring the level of the PD-1 binding protein bound to the composition by detecting the detectable antibody in order to measure the PD-1 present in the sample.

In some embodiments, PD-1 binding protein has uses in the in vitro and/or in vivo detection of PD-1 and specific cells, cell types, and/or cell populations (e.g. activated T and/or B cells). PD-1 binding proteins that are conjugated to detection-promoting agents optionally may be used for diagnostic functions, such as for companion diagnostics used in conjunction with a therapeutic regimen comprising the same or a related binding region, such as, e.g., a binding region with high-affinity binding to the same target biomolecule, an overlapping epitope, and/or the same epitope, such as, e.g., a nivolumab therapy.

In some embodiments, the PD-1 binding protein has uses for detecting the presence of PD-1, e.g. in vivo or in a biological sample. The PD-1 binding proteins or compositions thereof can be used in a variety of different detection assays, including but not limited to ELISA, immunoprecipitation, bead-based immunoassays, flow cytometry, mass spectrometry, and immunofixation electrophoresis (IFE). In some embodiments, the PD-1 binding protein is immobilized to a solid support or conjugated to biotin and bound to a streptavidin coated microtiter plate. For some embodiments, the PD-1 binding protein is directly detectable, such as, e.g., due to the presence of a label including but not limited to an enzyme (e.g. horseradish peroxidase), a fluorescent agent, radiological, or a colorimetric reagent.

For some embodiments, the PD-1 binding protein or compositions thereof are useful to quantitate PD-1 amounts in a sample, e.g. a biological sample. In some embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain the PD-1 of interest. In various embodiments, the sample is a body sample isolated or obtained from any vertebrate. In some embodiments, the sample is isolated or obtained from a mammal. In some embodiments, the sample is isolated or obtained from a human subject. In some embodiments, the biological sample is serum from a human subject. In some embodiments the biological sample is biopsy material. In some embodiments, the biological sample is biopsy material from a human subject. In some embodiments the biological sample is biopsy material from a tumor. In some embodiments the biological sample is biopsy material comprising tumor cells or cancer cells. In some embodiments the biological sample is primary cell culture material. In some embodiments, the biological sample is primary cell culture material from a human subject. In some embodiments, the biological sample is from a human subject or subjects treated with a therapeutic anti-PD-1 antibody or antibodies (e.g. nivolumab, pembrolizumab, and/or cemiplimab) or some other therapeutic directed to an immune checkpoint, such as, e.g. one or more of an anti-B7-1 antibody, anti-PD-L1 antibody, anti-PD-L2 antibody, anti-CTLA-4 antibody, and anti-LAG-3 antibody.

In some embodiments of the methods and uses of detecting and/or quantifying the presence of PD-1 described herein, the method or use comprises the detection of a "label" or "detection-promoting agent." In some further embodiments, the detection-promoting agent is a colorimetric, enzymatic, fluorescent, chromophoric, electron-dense, chemiluminescent, radiological, and/or other label, which may be detected directly using routine methods known to the skilled worker. In some embodiments, the detection-promoting agent is a fluorescent polypeptide or protein, such as, e.g., a GFP, blue fluorescent protein (BFP), cyan fluorescent protein (CFP), yellow fluorescent protein (YFP), or red fluorescent protein (RFP), which may optionally be fused, or a subunit thereof fused, to the PD-1 binding protein. In some further embodiments, the detection-promoting agent is an enzyme or ligand, which may be detected indirectly using routine methods known to the skilled worker. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives (e.g., 5-carboxyfluorescein), rhodamine and its derivatives, dansyl, umbelliferone, luciferin, luciferases (e.g., firefly luciferase and bacterial luciferase), 2,3-dihydrophthalazinediones, biotin/avidin, horseradish peroxidase (HRP), alkaline phosphatase, J3-galactosidase, glucoamylase, lysozyme, saccharide oxidases (e.g., glucose oxidase, galactose oxidase, and glucose-6-phosphate dehydrogenase), heterocyclic oxidases (e.g., uricase or xanthine oxidase) coupled with an enzyme that employs hydrogen peroxide to oxidize a dye precursor such as HRP, lactoperoxidase, or microperoxidase, spin labels, bacteriophage labels, and relatively stable radicals (also known as stable free radicals).

In some other embodiments, the method comprises (b) analyzing a sample by immunofixation electrophoresis (IFE) to compare the sample contacted with the PD-1 binding protein to a sample that has not been contacted with the PD-1 binding protein; (c) detecting the presence of the PD-1 binding protein in the biological sample; wherein a difference in the migration between the sample contacted with the PD-1 binding protein and the sample that has not been contacted with the PD-1 binding protein indicates the presence of the PD-1 binding protein in the biological sample. In some embodiments, the biological sample is isolated from a human subject.

For some embodiments of the methods herein, the PD-1 binding protein is immobilized to a solid support, and the method further comprises the step of separating the biological sample from the immobilized PD-1 binding protein bound to PD-1. In some embodiments, the immobilized PD-1 binding protein is conjugated to biotin and bound to a streptavidin coated microtiter plate.

In some embodiments, the PD-1 binding protein described herein, or a polynucleotide encoding it, is immobilized on a solid substrate. Solid substrates contemplated herein include, but are not limited to, microbeads, nanoparticles, polymers, matrix materials, microarrays, microtiter plates, or any solid surface known in the art (see e.g. U.S. Pat. No. 7,771,955). In accordance with these embodiments, a molecule of the present invention may be covalently or non-covalently linked to a solid substrate, such as, e.g, a bead, particle, or plate, using techniques known to the skilled worker (see e.g. Jung Y et ah, Analyst 133: 697-701 (2008)). Immobilized molecules of the invention may be used for screening applications using techniques known in the art. Non-limiting examples of solid substrates to which a molecule of the invention may be immobilized on include: microbeads, nanoparticles, polymers, nanopolymers, nanotubes, magnetic beads, paramagnetic beads, superparamagnetic beads, streptavidin coated beads, reverse-phase magnetic beads, carboxy terminated beads, hydrazine terminated beads, silica (sodium silica) beads and iminodiacetic acid (IDA)-modified beads, aldehyde-modified beads, epoxy-activated beads, diaminodipropylamine (DADPA)-modified beads (beads with primary amine surface group), biodegradable polymeric beads, polystyrene substrates, amino-polystyrene particles, carboxyl-polystyrene particles, epoxy-polystyrene particles, dimethylamino-polystyrene particles, hydroxy-polystyrene particles, colored particles, flow cytometry particles, sulfonate-polystyrene particles, nitrocellulose surfaces, reinforced nitrocellulose membranes, nylon membranes, glass surfaces, activated glass surfaces, activated quartz surfaces, polyvinylidene difluoride (PVDF) membranes, polyacrylamide-based substrates, poly-vinyl chloride substrates, poly-methyl methacrylate substrates, poly(dimethyl siloxane) substrates, and photopolymers which contain photoreactive species (such as nitrenes, carbenes, and ketyl radicals) capable of forming covalent linkages. Other examples of solid substrates to which a molecule of the invention may be immobilized on are commonly used in molecular display systems, such as, e.g., cellular surfaces, phages, and virus particles.

In another aspect, provided herein is a method for monitoring a treatment involving immunotherapy and/or related to immune checkpoint modulation in a subject. In some embodiments, the method comprises: (a) obtaining a biological sample from a subject, (b) contacting the biological sample with a PD-1 binding protein as provided herein, or a composition thereof, under a condition to allow binding of the PD-1 binding protein to PD-1 molecules in the sample to form a complex; wherein the subject has been treated with an immune checkpoint inhibitor and/or PD-1 targeted therapy. In some further embodiments, the subject has been diagnosed with and/or treated for bladder cancer, breast cancer (including triple negative for HER2, estrogen receptor, and progesterone receptor), Hodgkin's lymphoma, lung cancer, melanoma, Merkel cell cancer, multiple myeloma, non-small cell lung cancer, ovarian cancer, sarcoma, soft tissue sarcoma, and/or urothelial carcinoma. In some embodiments, the subject has been treated with an immune checkpoint inhibitor and/or PD-1 targeted therapy (e.g. nivolumab, pembrolizumab, or cemiplimab). In some further embodiments, the subject has been or will be treated with an anti-PD-1 antibody, anti-B7-1 antibody, anti-PD-L1 antibody, anti-PD-L2 antibody, anti-CTLA-4 antibody, and/or anti-LAG-3 antibody. In some embodiments, the subject is a human.

Various types of information may be gathered using the diagnostic embodiments of the PD-1 binding protein whether for diagnostic uses or other uses. This information may be useful, for example, in diagnosing neoplastic cell types, determining therapeutic susceptibilities of a patient's disease, determining the progression of anti-neoplastic therapies over time, determining the progression of immunomodulatory therapies over time, determining the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the PD-1 binding protein, and then individual patients could be further categorized into subpopulations based on their unique characteristic(s) revealed using those diagnostic embodiments. For example, the effectiveness of specific pharmaceuticals or therapies might be a criterion used to define a patient subpopulation. For example, a diagnostic PD-1 binding protein described herein may be used to differentiate which patients are in a class or subpopulation of patients predicted to respond positively to a therapeutic variant of that PD-1 binding protein, such as, e.g., lacking any label or detection-promoting agent. Accordingly, associated methods for patient identification, patient stratification, and diagnosis using PD-1 binding proteins are considered to be within the scope of the present invention.

B. Treatment of a Disease or Condition Using a PD-1 Binding Protein

In some aspects, provided herein is a method of treatment comprising administering to a subject in need thereof a therapeutically effective amount of a PD-1 binding protein described herein and/or a composition thereof. A PD-1 binding protein described herein can be administered using any appropriate delivery vehicle.

As used herein, the term "treating" refers to improving, reducing, eliminating, or lessening the severity of any aspect of a condition or disease in a subject, e.g. a cancer or autoimmune disease.

As used herein, the terms "subject" and "patient" are used interchangeably and can encompass a human or animal including, without limitation, a dog, cat, horse, cow, pig, sheep, goat, chicken, rodent, e.g., rat and mouse, and non-human primate, e.g., monkey. Preferred subjects are human subjects. The human subject may be a pediatric, adult or a geriatric subject. As used herein, the phrase "in need thereof" indicates the state of the subject, wherein therapeutic or preventative measures are desirable. Appropriate subjects for the methods described herein include, without limitation, humans diagnosed as having or suspected of having a cancer involving a PD-1 expressing cell.

In some embodiments, the method comprises administering a therapeutically effective amount of a PD-1 binding protein or composition thereof. As used herein, the terms "effective amount" or "therapeutically effective amount" refer to a sufficient amount of a compound being administered which will relieve to some extent one or more of the symptoms of the disease or condition being treated (e.g. cancer). The result can be reduction and/or alleviation of the signs, symptoms, or causes of a disease, or any other desired alteration of a biological system. For example, an "effective amount" for a method provided herein can be the amount of a compound described herein (e.g., a PD-1 binding protein) that is required to provide a clinically significant decrease in tumor growth or increase in lifespan. An appropriate effective amount in any individual case may be determined using techniques known to those in the art, such as a dose escalation study. Effective amounts of therapeutic agents can depend on other various factors, such as the frequency of administration, the duration of treatment, the severity of the condition being treated, the condition and prior medical history of the subject being treated, the possibility of co-administration with other therapeutic treatments such as use of other agents, and the judgment of the treating physician. A dose that is lower than an effective dose can initially be administered to a subject, and the dose can then be gradually increased over time until the desired effect is achieved.

The frequency and duration of administration can be any frequency or duration that improves a symptom of, for example, tumor growth without being toxic. For example, an agent can be administered once or twice a day, once every other day, once or twice a week, or as needed. The frequency of administration can remain constant or can be variable during the duration of treatment. An effective duration of treatment can vary from several weeks to several months or years. For example, an effective duration of treatment can be six months, five years, or a lifetime. In addition, a course of treatment can include rest periods. Multiple factors can influence the actual effective frequency and duration of treatment. For example, the activities of the particular therapeutic agents used, the severity of the condition being treated, the doses administered, and the condition and prior medical history of the mammal being treated can affect the effective frequency and duration of treatment.

In some embodiments of the method of treatment, the condition or disease being treated is a tumor, cancer, or autoimmune disorder. In some further embodiments, the condition or disease involves a PD-1 expressing cell type and/or a PD-1-ligand expressing cell, such as, e.g., a tumor cell expressing PD-L1 or PD-L2. In some further embodiments, the cancer is selected from bladder cancer, breast cancer (including triple negative for HER2, estrogen receptor, and progesterone receptor), Hodgkin's lymphoma, lung cancer, melanoma, Merkel cell cancer, multiple myeloma, non-small cell lung cancer, ovarian cancer, sarcoma, soft tissue sarcoma, and/or urothelial carcinoma. In some embodiments, the tumor or cancer is not characterized as "cold" or immune-excluded compared to "hot" tumors, such as, e.g., melanoma, bladder, kidney, head and neck, non-small cell lung cancers. In some embodiments, the tumor or cancer is not characterized as "cold" or immune-excluded due to a relative absence of CD8+ T cells, interferon-gamma signaling, and PD-L1 expression compared to "hot" tumors. In some embodiments, the tumor or cancer is not characterized as "cold" or immune-excluded due to a relative absence of PD-L1 and/or PD-L2 expression in the tumor compared to "hot" tumors. In some embodiments, the tumor or cancer is not characterized as having a high mutational burden as compared to "hot" tumors.

In some embodiments of the method of treatment, the method comprises administering to the subject the PD-1 binding protein and an additional therapeutic. In some further embodiments, the additional therapeutic is an immune checkpoint inhibitor and/or an anti-PD-1 antibody, anti-B7-1 antibody, anti-PD-L1 antibody, anti-PD-L2 antibody, anti-CTLA-4 antibody, and/or anti-LAG-3 antibody (e.g. fianlimab or relatlimab). In some embodiments, the subject has not been diagnosed with and/or is not a risk of developing an autoimmune disease, such as, e.g., Crohn Disease, dermatomyositis, inflammatory bowel disease, multiple sclerosis, rheumatoid arthritis, psoriasis, polymyalgia rheumatic, Addison disease, Sjogren syndrome, systemic lupus erythematosus, systemic scleroderma, ulcerative colitis, giant cell arteritis, sicca syndrome, regional enteritis, or Meniere disease.

In some embodiments of the method of treatment, the condition or disease being treated is a tumor or cancer but the subject also has an autoimmune disease. In some further embodiments, the autoimmune disease is selected from Crohn Disease, dermatomyositis, inflammatory bowel disease, multiple sclerosis, rheumatoid arthritis, psoriasis, polymyalgia rheumatic, Addison disease, Sjogren syndrome, systemic lupus erythematosus, systemic scleroderma, ulcerative colitis, giant cell arteritis, sicca syndrome, regional enteritis, and Meniere disease.

In some embodiments of the method of treatment, the condition or disease is inflammation, inflammatory disease, and/or autoimmune disease. In certain embodiments, the inflammation or inflammatory disease is associated with an autoimmune disease. In certain further embodiments, the autoimmune disease is selected from Crohn Disease, dermatomyositis, inflammatory bowel disease, multiple sclerosis, rheumatoid arthritis, psoriasis, polymyalgia rheumatic, Addison disease, Sjogren syndrome, systemic lupus erythematosus, systemic scleroderma, ulcerative colitis, giant cell arteritis, sicca syndrome, regional enteritis, and Meniere disease.

In some embodiments of the method of treatment, the condition or disease is an autoimmune disease or disorder selected from a B-cell-, plasma cell- or antibody-mediated disease or disorder, such as for example leukemia, lymphoma, myeloma, rheumatic disease, spondylitis, Human Immunodeficiency Virus-related diseases, amyloidosis, hemolytic uremic syndrome, polyarteritis, septic shock, Crohn's Disease, rheumatoid arthritis, ankylosing spondylitis, psoriatic arthritis, ulcerative colitis, psoriasis, asthma, allergic asthma, Sjogren's syndrome, graft-versus-host disease, graft rejection, diabetes, vasculitis, scleroderma, and systemic lupus erythematosus.

C. Vaccine Adjuvant

In some aspects, provided herein is a method of vaccination comprising administering to a subject a vaccine and an effective amount of a PD-1 binding protein described herein, and/or a composition thereof, to increase or enhance an immune response to the vaccine. For some embodiments, the amount of PD-1 binding protein is effective in increasing the strength of a humoral response to the vaccine as compared to a control without administering any PD-1 binding protein. For some embodiments, the amount of PD-1 binding protein is effective in increasing the quantity of antibody titer(s) resulting from vaccine administration. For some embodiments, the PD-1 binding protein is effective in increasing the number of memory CD8+ T cells and/or central memory T cells.

IV. Articles of Manufacture

Provided herein is a kit comprising a (i) PD-1 binding protein as described herein, or a polynucleotide encoding it, and (ii) a device or at least one additional reagent.

Provided herein is a kit for administering to a subject a PD-1 binding protein as described herein. In some embodiments, the PD-1 binding protein is formulated, delivered and/or stored for use in physiologic conditions, such as, e.g., via intravenous (IV) administration or injection. In some embodiments, the kit further comprises an injection device.

Provided herein is a kit for detecting PD-1 in a sample or subject using a PD-1 binding protein as described herein. In some embodiments, the kit comprises a reagent for detecting the PD-1 binding protein. In some embodiments, the PD-1 binding protein is formulated, delivered and/or stored for use in physiologic conditions, such as, e.g., via intravenous (IV) administration or injection. In some embodiments, the kit further comprises an injection device.

In another aspect, the kit is an immunoassay kit for specifically detecting PD-1 in a biological sample, the kit comprising a labeled PD-1 binding protein or a composition as thereof (e.g. a diagnostic composition). In some further embodiments, the PD-1 binding protein is labeled with a detection-promoting agent known to the skilled worker and/or described herein. In some embodiments, the immunoassay kit comprises: (a) the PD-1 binding protein or a composition thereof; (b) a detectable antibody that binds to the PD-1 binding protein; and (c) instructions for detecting said PD-1 binding protein. In some embodiments, the kit is useful in an immunoassay for detecting or quantitating PD-1.

The kit may further comprise instructions for use, such as, e.g. a publication, a recording, a diagram, or any other medium of expression which is used to communicate the usefulness of the PD-1 binding protein for one of the purposes set forth herein. The instructional material of the kit can, for example, be affixed to a container which contains the PD-1 binding protein or be shipped together with a container which contains the PD-1 binding protein.

V. Additional Antigen Binding Proteins

Figure 15A:
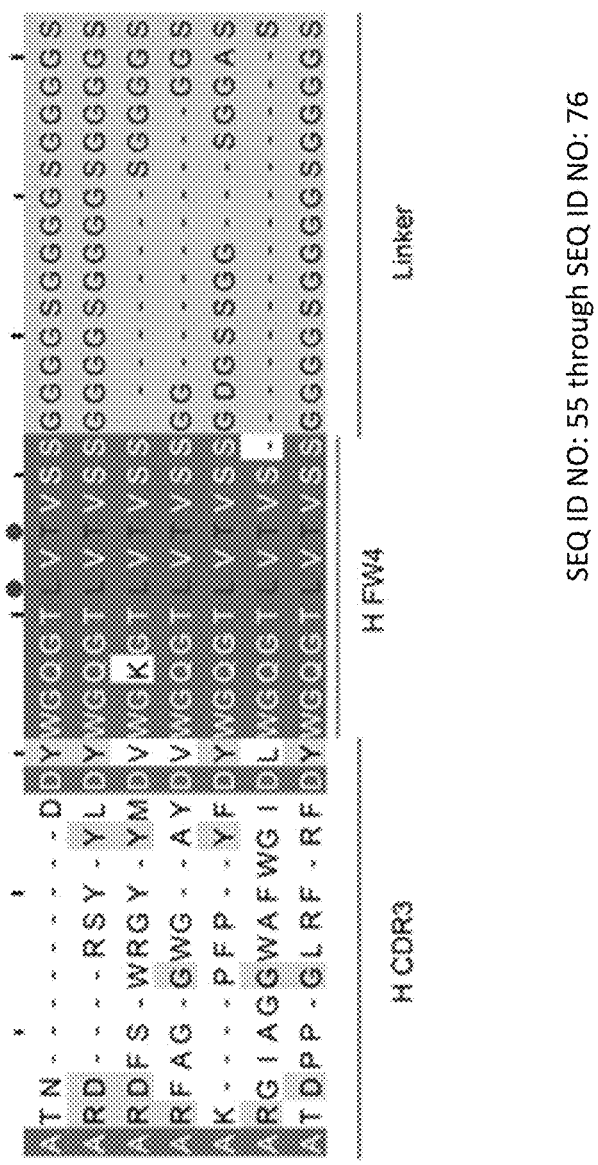
Figure 15B:
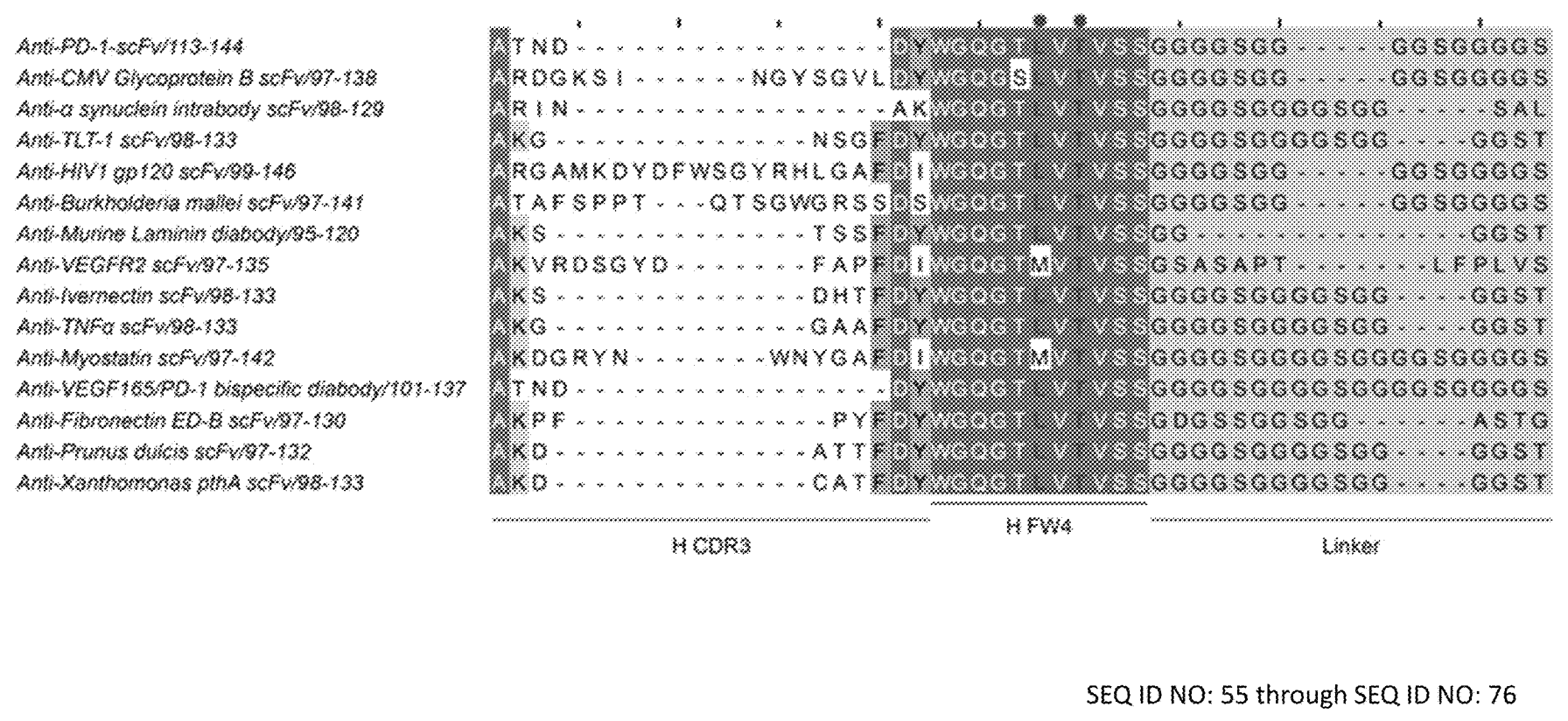

The solubility, aggregation and functional properties of the anti-PD-1 scFv were all improved by the L124G and T126R mutations. As shown in FIG. 15, a wide array of scFv's and diabodies contain both Leu and Thr residues at analogous positions to anti-PD-1 scFv residues Leu 124 and Thr 126 (the scFv's in FIG. 15A have known structures, while those in FIG. 15B have unknown structures). Moreover, additional Aggrescan 3D based analyses of the scFv's presented in FIG. 15A revealed that the conserved Leu and Thr residues are in APR regions. Thus, a number of previously described scFv's contain APRs that are formed, in part, by the conserved Leu and Thr residues. The scFv's listed in FIG. 15 include those targeting HIV GP120, alpha synuclein, VEGF and TNF alpha. Therefore, in some embodiments, mutations of the conserved Leu and Thr residues, to those analogous to the ones described herein are used to enhance the properties, e.g. solubility and functional properties, of a range of important scFv molecules and other antigen binding proteins.

Accordingly, in some embodiments, provided herein is an antigen binding protein comprising a heavy chain framework 4 region (VH-FR4) comprising at least one of: a glycine residue positioned six amino acid residues carboxyl-terminal from the last amino acid residue of a heavy chain CDR-3, and an arginine residue positioned eight amino acid residues carboxy-terminal to the last amino acid residue of a heavy chain CDR-3. The VH-FR4 may be derived from the conserved VH-FR4 of SEQ ID NO: 27 (WGQGTLVTVSS). In some embodiments, the VH-FR4 comprises a sequence selected from: WGQGTGVRVSS (SEQ ID NO: 28), WGQGTGVTVSS (SEQ ID NO: 43), and WGQGTLVRVSS (SEQ ID NO: 44).

The binding protein may be a recombinantly produced antibody, monoclonal antibody, multiclonal antibody, chimeric antibody, humanized antibody, primatized antibody, CDR-grafted antibody, human antibody (including recombinantly produced human antibodies), multispecific antibody (e.g. bispecific antibody), monovalent antibody, multivalent antibody, synthetic antibody, and antigen binding fragment or derivative of an antibody, such as, e.g., an antibody variable fragment (Fv), single-chain variable fragment (scFv), scFv-Fc fusion, single chain Fv-CFB minibody, bispecific tandem scFv fragment, multimerizing scFv fragment (diabody, triabody, tetrabody), Fd fragment, Fab fragment, F(ab') fragment, bivalent F(ab')2 fragment, single-domain antibody fragment (sdAb) or Nanobody®, bivalent Nanobody®, bispecific Nanobody®, bivalent minibody, bispecific minibody, autonomous VH domain, VHH, bispecific tandem VHH fragment, VNAR fragment, Fc antigen binding domain (Fcab), isolated complementary determining region 3 (CDR3) fragment, constrained framework region 3, framework region 4 (FR3-CDR3-FR4) polypeptide, dimeric CH2 domain fragment (CH2D), heavy-chain antibody domain derived from a camelid VHH fragment or VH domain fragment, a heavy-chain antibody domain derived from a cartilaginous fish; or any other immunoreactive molecule or genetically manipulated counterparts of any of the foregoing which retain binding functionality.

Antigens targeted by the antigen binding protein may include, without limitation, PD-1, connexin26, fibronectin ED-B, DENV1 FAB 14C10, SARS-CoV-2 RBD, CMV Glycoprotein B, α synuclein intrabody, TLT-1, HIV1 gp120, *Burkholderia mallei*, murine laminin, VEGFR2, ivermectin, TNFα, myostatin, VEGF165, *Prunus dulcis, Xanthomonas* pthA.

In other aspects, provided herein are compositions comprising an antigen binding protein described herein and a pharmaceutically acceptable carrier or excipient, such as, e.g., as described in (Remington's Pharmaceutical Sciences 16th edition, Osol, A. Ed. (1980) and/or known in the art. Preferably, the pharmaceutically acceptable carrier is a liquid suitable for intravenous administration and/or injection of the antigen binding protein.

In further aspects, provided herein are nucleic acids encoding the antigen binding proteins, as well as expression vectors comprising an aforementioned nucleic acid, and host cells comprising an aforementioned nucleic acid and/or expression vector herein. Provided herein are methods comprising culturing a host cell comprising a nucleic acid and/or expression vector described herein under conditions wherein an antigen binding protein is expressed, and recovering, extracting or isolating the antigen binding protein.

In a further aspect, provided herein is an antigen binding protein further comprising a detection-promoting agent. In another aspect, provided herein is a diagnostic composition comprising an antigen binding protein comprising a detection-promoting agent and an acceptable carrier or excipient. The ability to conjugate detection-promoting agents known in the art to an antigen binding protein provides useful compositions for the detection of certain cells, such as, e.g., cancer expressing the target antigen, tumor, immune, and/or infected cells. These diagnostic embodiments of the antigen binding protein may be used for information gathering via various imaging techniques and assays known in the art. For example, diagnostic embodiments of the antigen binding proteins of the invention may be used for information gathering via imaging of individual cancer cells, immune cells (e.g. a T cell, NK cell, B cell, tumor infiltrating immune cell (e.g. APC), myeloid derived immune cell (e.g. MDSC), or macrophage), and/or infected cells in a patient or biopsy sample.

Also provided herein is a kit comprising a (i) antigen binding protein as described herein, or a polynucleotide encoding it, and (ii) a device or at least one additional reagent.

Provided herein is a kit for administering to a subject an antigen binding protein as described herein. In some embodiments, the antigen binding protein is formulated, delivered and/or stored for use in physiologic conditions, such as, e.g., via intravenous (IV) administration or injection. In some embodiments, the kit further comprises an injection device.

Provided herein is a kit for detecting an antigen of interest in a sample or subject using an antigen binding protein as described herein. In some embodiments, the kit comprises a reagent for detecting the antigen binding protein. In some embodiments, the antigen binding protein is formulated, delivered and/or stored for use in physiologic conditions, such as, e.g., via intravenous (IV) administration or injection. In some embodiments, the kit further comprises an injection device.

In another aspect, the kit is an immunoassay kit for specifically detecting a target antigen in a biological sample, the kit comprising a labeled antigen binding protein or a composition as thereof (e.g. a diagnostic composition). In some further embodiments, the antigen binding protein is labeled with a detection-promoting agent known to the skilled worker and/or described herein. In some embodiments, the immunoassay kit comprises: (a) the antigen binding protein or a composition thereof; (b) a detectable antibody that binds to the antigen binding protein; and (c) instructions for detecting said antigen binding protein. In some embodiments, the kit is useful in an immunoassay for detecting or quantitating antigen.

The kit may further comprise instructions for use, such as, e.g. a publication, a recording, a diagram, or any other medium of expression which is used to communicate the usefulness of the antigen binding protein for one of the purposes set forth herein. The instructional material of the kit can, for example, be affixed to a container which contains the antigen binding protein or be shipped together with a container which contains the antigen binding protein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

The indefinite articles "a" and "an," as used herein in the specification and in the claims, unless clearly indicated to the contrary, should be understood to mean "at least one."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

All references, patents and patent applications disclosed herein are incorporated by reference with respect to the subject matter for which each is cited, which in some cases may encompass the entirety of the document.

The present invention has been described in terms of one or more embodiments, and it should be appreciated that many equivalents, alternatives, variations, and modifications, aside from those expressly stated, are possible and within the scope of the invention. The following examples are meant only to be illustrative and are not meant as limitations on the scope of the invention or of the appended claims.

EXAMPLES

The PD-1 pathway plays a vital role in inhibiting immune responses, promoting self-tolerance, and cancer immune escape. PD-1 binding proteins have been approved for use in immunotherapy for cancer patients, e.g. for melanoma, breast cancer, cervical cancer, liver cancer, lung cancer, lymphoma, and stomach cancer.

In the following examples, PD-1 binding proteins, each comprising six CDRs, were designed and tested. The compositions and methods provided herein are based at least in part on the development of single chain variable fragment (scFv) variants from nivolumab. The initial scFv was not soluble in tissue culture media after production in BL21-DE3 *E. coli* and failed to block PD-1 signaling via PD-L1 in a cell-based assay. The scFv was modified into several variants to increase solubility in tissue culture media. Uses of the modified scFv in blocking PD-1 signaling, for detecting PD-1, and targeted delivery to PD-1 expressing cells are explored. Advantages of scFv molecules compared to antibodies include relatively smaller size, increased tissue and tumor penetration, and reduced manufacturing costs.

Example 1. Single-Chain Fv Design

Using the nivolumab sequence, several scFv polypeptides were designed and tested. An anti-PD-1 scFv was generated comprising the heavy chain variable from nivolumab (SEQ ID NO: 24) and the light chain variable domain from nivolumab (SEQ ID NO: 9) separated by a scFv linker (SEQ ID NO: 38). This scFv failed to block human PD-1/PD-L1 interactions in cell-based assays and in vivo most likely due to a solubility and/or aggregation issue as observed in tissue culture media (see Example 3, below, and FIG. 6).

To solve this problem, studies of variants of this original scFv were performed wherein the variants had different point mutations of particular residues, such as, e.g., substituting one or more hydrophobic residues with a more hydrophilic and/or smaller residue to enhance solubility of the scFv's.

Figure 2:
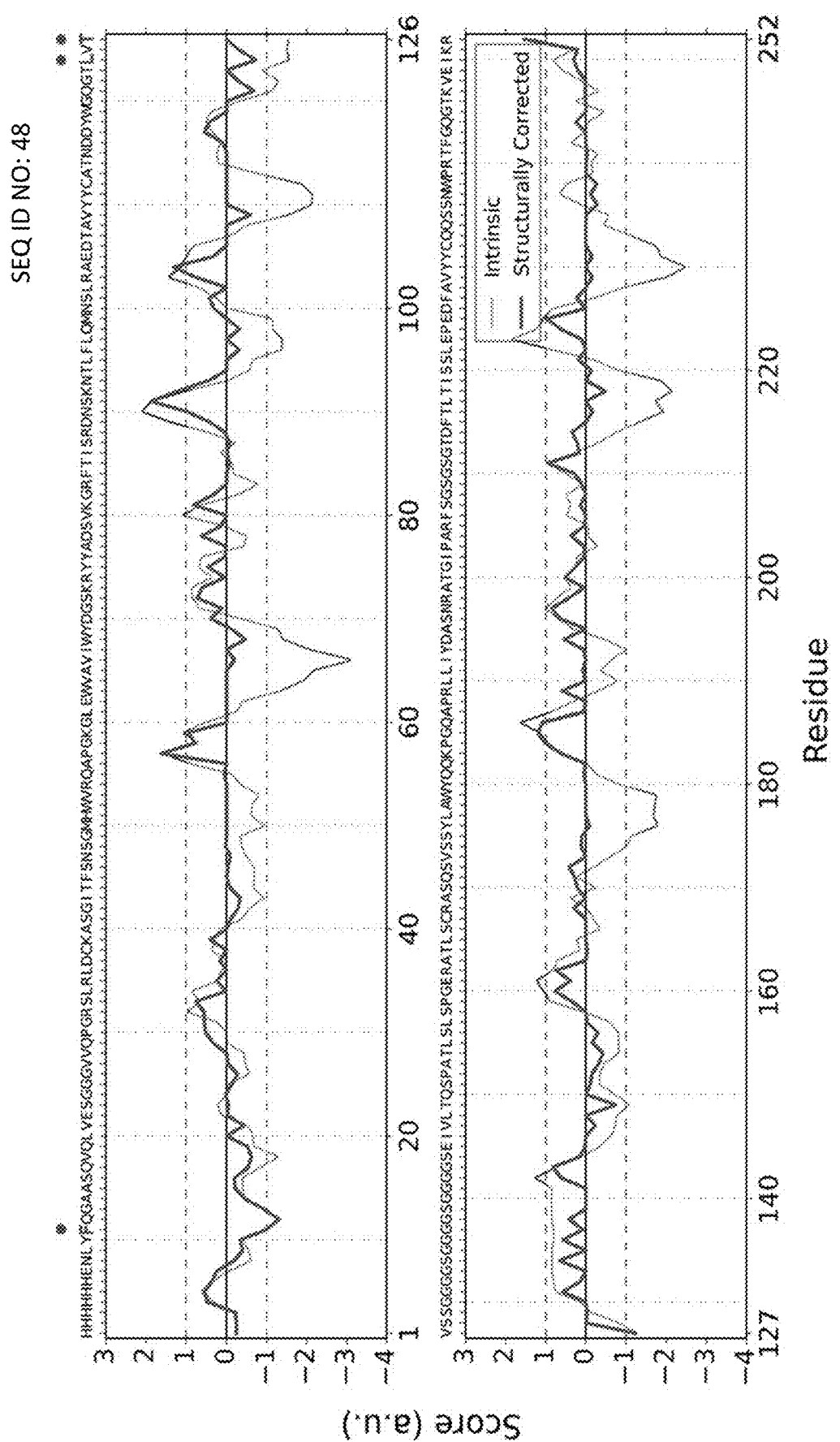
FIG. 2 displays results of CamSol software-based analyses modeling of an anti-PD-1 scFv derived from nivolumab. The amino acid residues comprising the anti-PD-1 scFv are listed above the figure. The "intrinsic" data (light blue (gray); some containing red tips) is for the unfolded molecule. The "structurally corrected" data (in green (darker line)) aided in the identification of hydrophobic residues on the surface of the anti-PD-1 scFv. Certain residues identified as candidates for mutation are shown on the top line highlighted by an asterisk.

Existing nivolumab structural data, and "molecular threading" techniques were used to generate a structural model of the anti-PD-1 scFv and a PDB file was generated. CamSol software was used to identify hydrophobic residues on a 3D structural model of the anti-PD-1 scFv using the PDB file (see e.g. Sormanni et al., *J Mol Biol* 427: 478-90 (2015)). Sormanni et al. have described an algorithm, termed CamSol, that predicts what residues contribute the greatest amount of hydrophobicity to a folded protein or protein domain. This program requires structural information about proteins of interest, which were available for nivolumab. The coordinates for the anti-PD-1 scFv model were input into the CamSol program, which predicted the "structurally corrected" hydrophobicity of each residue (FIG. 2, green line). It is noted that many of the identified hydrophobic residues were not candidates for mutations because they are derived from intrinsically hydrophobic regions (light blue and red line) of the molecule. This analysis highlighted L124 and T126 in the scFv as potential residues for mutation. The mutations made herein are often referred to in the Examples by their position relative to the scFv. They may also be referred to relative to the nivolumab reference heavy and light chain sequences. Table 2 and paragraph 217 may be used to coordinate the reference sequences with the mutations. L124G in the scFv is position 108 in the nivolumab heavy chain reference sequence. T126G in the scFV is position 110 in the nivolumab heavy chain reference sequence.

Figures 3A, 3B:
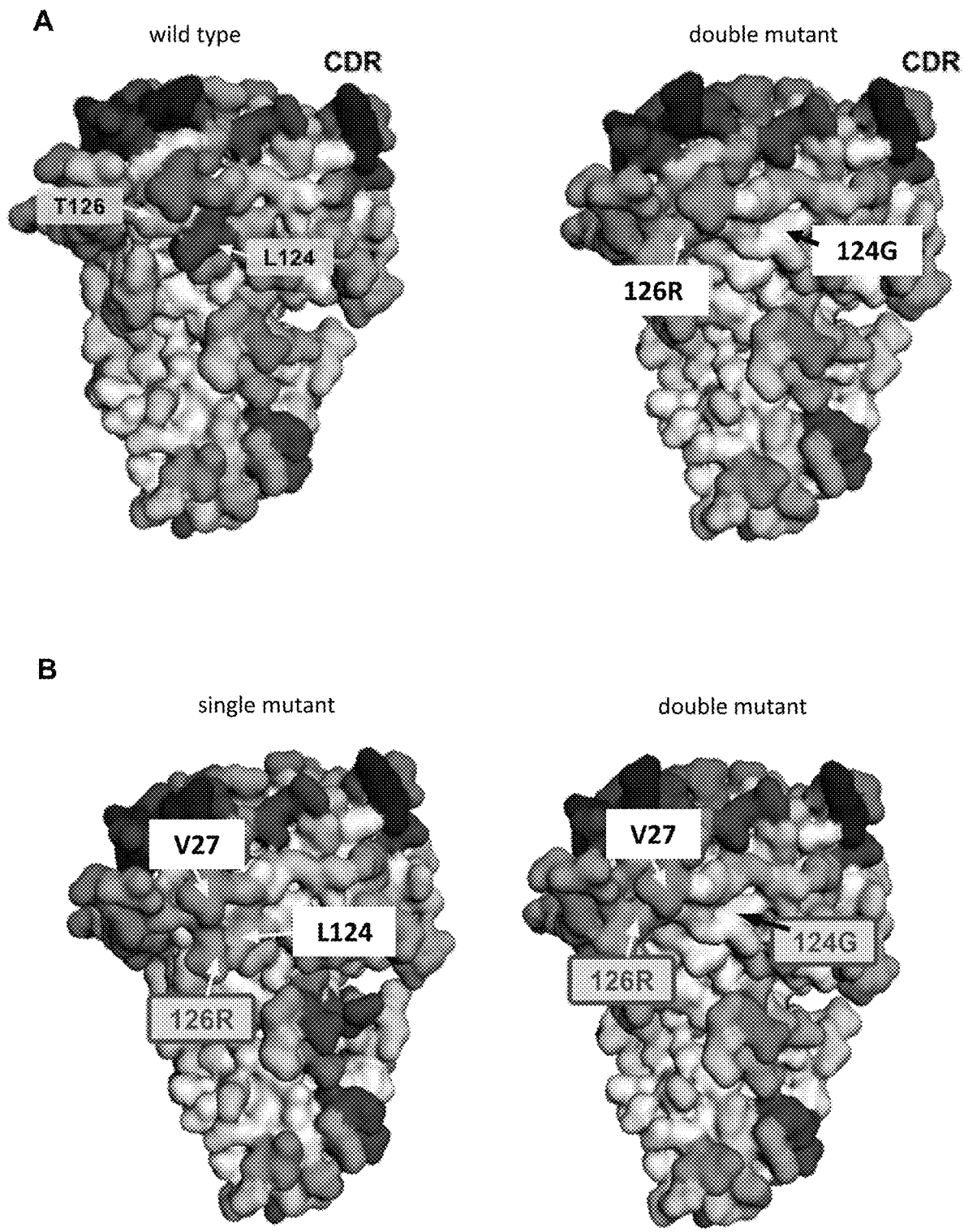
FIGS. 3A-3B show results of Aggrescan3D software-based analyses modeling an anti-PD-1 scFv derived from nivolumab. For each residue, the darker the blue indicates higher contributions to solubility, whereas the darker the red indicates higher insolubility and aggregation propensity.

Another algorithm similar to CamSol is Aggrescan3D (see e.g. Gil-Garcia M et al., *Mol Pharm* 15: 3846-59 (2018)). Aggrescan3D was also used to identify candidate residues for mutation. When any given residue is analyzed by the Aggrescan3D program, the darker the blue, the higher its contribution to solubility. In contrast, the darker the red, the higher the insolubility and aggregation propensity. This analysis highlighted L124 and T126 as potential residues for mutation (FIG. 3A). FIG. 3A (left) shows the results for the original anti-PD-1 scFv ("wild-type"). FIG. 3A (right) shows the results for an anti-PD-1 "double mutant" (abbreviated hereafter as anti-PD-1dm), which comprises two point mutations: L124G and T126R. As shown in FIG. 3A (left), the Aggescan3D algorithm labeled L124 and T126 as two of the most insoluble/aggregation promoting residues on the surface of the scFv. As shown in FIG. 3A (right), the anti-PD-1dm ("double mutant") was predicted to have greatly improved solubility (note the absence of a cluster of red colored residues present in the right model). It is apparent that the L124G and T126R substitutions have eliminated a cluster of "red residues" and thus predicted to have improved the solubility of the molecule. Furthermore, the Aggrescan3D program assigns each residue a structurally corrected aggregation value that is termed the A3D score. The more positive the A3D score the higher the aggregation propensity (i.e., the deeper the red color). The A3D scores for Leu 124 and Thr 126 were 1.495 and 0.2765 respectively; where 1.495 was the highest A3D score for all residues on the surface of the molecule and 0.2765 was the eleventh. Therefore, in agreement with the CamSol program, the region containing Leu 124 and Thr 126 was predicted to form an aggregation prone region (APR) that promotes aggregation and insolubility.

Additional Aggrescan3D models of the anti-PD-1sm and the anti PD-1dm are presented in FIG. 3B. The mutated residues are depicted within purple borders. When compared to the wt anti-PD-1 (FIG. 3A, left) it is apparent that the APR in both mutants is greatly diminished. An additional advantage of the L124G/T126R anti-PD-1dm is suggested by a comparison of the model of the anti-PD-1dm presented in FIG. 3B (right), with that of the wt in FIG. 3A (left); namely, that owing to changes in the hydrophobic pocket in the double mutant, Val27 is predicted to promote diminished levels of aggregation (the Aggrescan 3D core for residue Val27 was 1.4893 in the wt and 0.7936 in the double mutant (also represented by the intensity of the red color for Val 27 in the two figures)).

Figure 4:
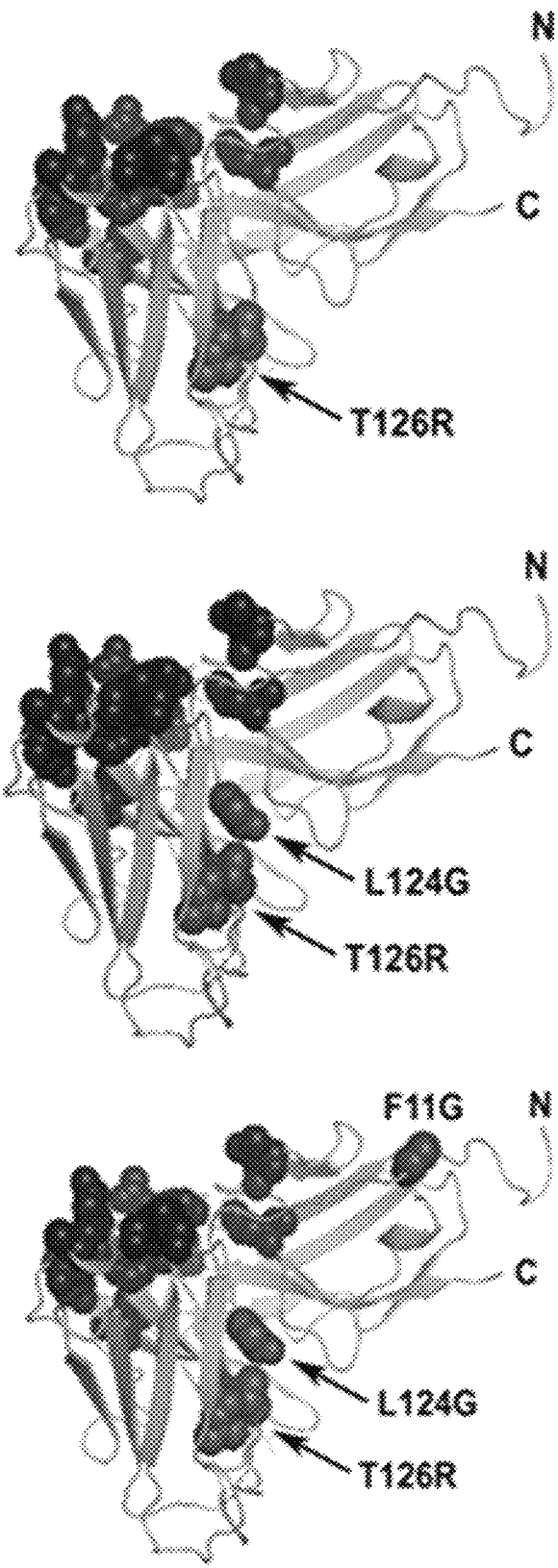
FIG. 4 shows structural models depicting variant scFv's having different mutations (in red, residues indicated with arrows and labeled) that were introduced onto the surface of the original anti-PD-1 scFv. On the top is the model of the T126R ("single mutation"), in the middle is T126R/L124G ("double mutation"), and on the bottom is the "triple mutation" T codons for the 124G/126R double mutations. (For the single T126R mutant, the sequence for Leu124 is ctg). Finally, according to the Kabat numbering system for immunoglobulins (Kabat et al, *Sequences of Proteins of Immunological Interest,* 5th Ed. Public Health Service, National Institutes of Health, Bethesda, Md. (1991)), anti-PD-1 scFv residues Leu 124 & Thr 126 are numbered 108 and 110, respectively.

Thus, these analyses both predicted that mutating L124 and/or T126 to residues of less hydrophobic character (e.g. L124G or T126R) may have the potential to increase the solubility of the anti-PD-1 scFv. The hydrophobic residue threonine at position 126 was changed to arginine to increase hydrophilic nature at this position. Candidate residues for mutation were based on multiple parameters besides hydrophobicity contributions, such as, e.g., surface exposure, avoiding clashes with neighboring side-chain residues, the isoelectric points (pI's) of mutated molecules, and maintaining antigen binding function. The leucine residue at position 124 was changed to glycine, which has the smallest R group, to reduce hydrophobicity without disturbing nearby residues required for binding to PD-1 (blue residues in FIG. 4; middle and bottom models). Likewise, because of additional concerns about disruption of the PD-1 binding site, the phenylalanine residue at position 11 was selected for mutation to a glycine residue. Structural models depicting the locations of Thr 126, Leu 124, and Phe 11 are presented in FIG. 4. The pI of the T126R mutant, as determined using the ExPASy portal, was 8.87 versus 8.65 for the wt scFv. Hydrophobic residue Leu 124 was eliminated by changing it to Gly (FIG. 4). A small residue was substituted in this location because of concerns about disturbing nearby CDR residues (i.e., the blue residues in FIG. 4) required for binding to PD-1 (see, e.g. Lee). The L124G mutation did not change the pI of the molecule.

An additional feature of the Aggrescan 3D program is the average score, which is a normalized indicator of the aggregation propensity/solubility of proteins. The average score allows a comparison of the solubility of wt and mutant protein structures. The more negative the value, the higher the normalized solubility. Therefore, this feature was used to predict whether the anti-PD-1 scFv's containing either the T126R single mutant (sm) or the L124G/T126R double mutant (dm) would have increased solubility compared to the wt scFv. The Aggrescan 3D based average scores for the wt anti-PD-1 scFv, the anti-PD-1sm and the anti-PD-1dm were −0.7198, −0.7655 and −0.7698 respectively. Thus, relative to the wt anti-PD-1 scFv, the anti-PD-1sm and the anti-PD-1dm were predicted to have increased solubility.

Figures 5A, 5B, 5C:
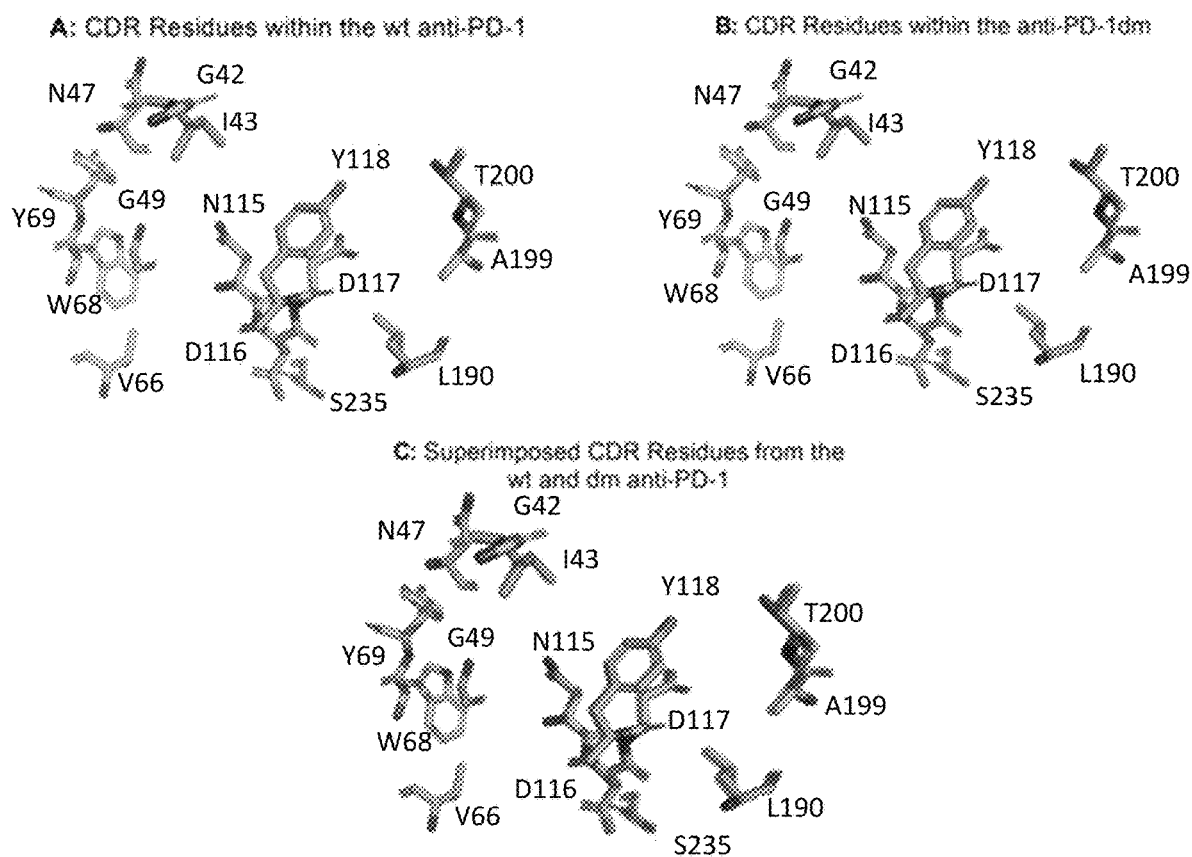

The AGGRESCAN 3D program was used to generate models of both the original anti-PD-1 scFv ("wild-type") and of the anti-PD-1dm ("double mutant"). The resulting PDB files were then uploaded into PyMOL and then the structures were superimposed. Representations of the locations of the residues within the CDRs of the original anti-PD-1 scFv and the anti-PD-1dm are shown in FIGS. 5A and 5B, respectively. FIG. 5C presents the results of the superposition of CDR residues of the original anti-PD-1 scFv and the anti-PD-1dm. This analysis predicts that the anti-PD-1dm containing the L124G and T126R mutations (the "double mutant") would not sustain any changes in the CDRs compared to the "wild-type" anti-PD-1 scFv. Based on these modeling studies, it was concluded that the double mutant would not change the distribution of residues within the CDR regions.

Structures of anti-PD1 wild-type and mutants were also predicted, using AlphaFold2 conjugated with MMseqs2, a fast homology searching algorithm (see Mirdita et al. 2021. Research Square). The Alpha Fold based model of the anti-PD-1 scFv was compared to the original structure (Shin J et al., Protein Expr Purif 177: 105766 (2001)) generated using SWISS-MODEL (Waterhouse, et al. Nucleic Acids Res 46:W296-W303). In FIG. 12, the Alpha Fold based structure of the "wild-type" anti-PD-1 scFv is labeled A.1, the SWISS-MODEL generated structure is labeled A.2, and the PyMol (50) based superposition of the two molecules is labeled A.3. Inspection of the superimposed structures establishes that with the exception of the $(Gly4S)_3$ linker, the Alpha Fold based model of the anti-PD-1 scFv is nearly identical to the previously reported SWISS-MODEL (RMSD of 1.056). To determine if the L124G/T126R mutations alter the structure of the anti-PD-1 scFv, Alpha Fold was also used to determine the structure of the anti-PD-1dm (FIG. 12 B.2). Using the superimpose function of PyMol, the structure of the anti-PD-1dm (B.2) was also aligned with the Alpha Fold based model of the anti-PD-1 scFv (A.1). It is clear from this alignment that the structures of the wild-type and double-mutant are nearly identical (B.3: RMSD value of 0.403). The results were also highly consistent with those obtained using the structure prediction program RoseTTA Fold (see Baek et al. Science 373:871-876 (2021)). All calculations were made using the default parameters. Based on these structure-based superposition studies, it was concluded that the L124G and T126R mutations would have little impact on the structure of the anti-PD-1 scFv.

ScFv's homologous to the anti-PD-1 double mutant were identified using Protein BLAST (NCBI). The identified scFv sequences were aligned, relative to the two residues mutated in this study (i.e., Leu 124 and Thr 126) using clustal-omega.

Example 2. Single-Chain Fv Generation

The T126R anti-PD-1 single mutant (anti-PD-1sm) was generated using the primer 5' ggccagggcaccctggtgagggtgagcagcggc 3' (SEQ ID NO: 45) and its complement. The L124G/T126R double mutant (anti-PD-1dm) was prepared in a QuikChange reaction (Agilent) using the primer 5' ggccagggcaccggggtgagggtgagcagcggc 3' (SEQ ID NO: 46) and its complement. Codons for the Gly and Arg residues are underlined. The DNA sequence of the resulting mutants, and the amino acid sequence of the corresponding proteins (both shown in FIG. 13), were generated using the ExPASy resource portal. Once the necessary plasmids were generated and transformed into *E. coli* BL21 cells, the mutant anti-PD-1 scFv's were isolated using the urea/high pH and Ni-NTA chromatography protocol, presented in Shin et al.

SDS-PAGE analyses of ~1 & 4 ug aliquots of the purified wt anti-PD-1 scFv, the anti-PD-1sm and anti-PD1 dm are presented in FIG. 14. All three of the −27 kDa anti-PD-1 scFv's are highly purified; they migrate at the expected locations (the presence of the N-terminal 6×His and TEV sequences likely explain the slightly higher mobility of the scFv's relative to the 27 kDa marker).

The three mutant anti-PD-1 scFv variants depicted in FIG. 4 were purified using the following method. The coding sequence for each was contained within a pLIC-His plasmid in frame with a 6×His tag and a TEV protease cleavage site (see e.g. Shin J et al., Protein Expr Purif 177: 105766 (2021)). Then, plasmid pLIC-His-anti-PD-1 scFv was transformed into *E. coli* (BL21 DE3; pLysS). Protein expression was induced at an OD 600 of ~ 0.6 by addition of IPTG (0.1 mM), and the cells were grown for 8 hours at 30° C. The cells were then harvested by centrifugation. The cell pellet was re-suspended in 100 mL of Buffer A (50 mM Tris·HCl pH 8.0, 0.3 M NaCl, 2 mM EDTA, 10% glycerol, 1 mM PMSF, 1% Igepal CA-630 and 0.1% 0-mercaptoethanol), and the cells were lysed by passage through a homogenizer. To remove cell debris and insoluble proteins, the lysate was centrifuged for 30 min at 18,000 rpm (38,700 g) at 4° C. Next, a urea/high pH-based protocol was used to extract the anti-PD-1 scFv variants. The pellet was re-suspended in 100 mL of Buffer B (100 mM Tris·HCl pH 12.5, 2 M urea, 20 mM imidazole, 10% glycerol and 0.02% Tween 80) and incubated at room temperature for 30 minutes with gentle rocking (see e.g. Patra A et al., *Protein Expr Purif* 18: 182-92 (2000)). Following incubation, the pH was lowered to pH 8.0 via addition of 1 N HCl, while stirring. The suspension was then centrifuged for 20 min at 18,000 rpm at 4° C. to obtain the solubilized anti-PD-1 scFv of interest.

The three mutant anti-PD-1 scFv variants depicted in FIG. 4 were refolded using the following method. The solubilized anti-PD1 scFv was mixed with QIAGEN Ni-NTA agarose beads (~2 mL of beads) for 1 hour at 4° C. with gentle rocking. The Ni-NTA beads, bound to the unfolded anti-PD1 scFv, were then pelleted in a centrifuge; non-bound material was removed by aspiration. As an initial wash, the Ni-NTA agarose resin was re-suspended in Buffer B (5×column volume), incubated for five minutes and then re-pelleted in the centrifuge. The Ni-NTA beads were re-suspended in ten times the bead volume of Buffer C (20 mM Tris·HCl pH 8.0, 100 mM NaCl, 0.1% Triton X-100, 4 mM oxidized glutathione and 4 mM reduced glutathione) and incubated for 30 minutes at 4° C. Upon centrifugation for 10 min, and aspiration of Buffer C, the pellet was re-suspended in ten times column volumes of Buffer D (20 mM Tris·HCl pH 8.0, 100 mM NaCl, 5 mM β-cyclodextrin, 4 mM oxidized glutathione and 4 mM reduced glutathione) and incubated for 1 hour at 4° C. After an additional cycle of centrifugation and aspiration, the pellet was re-suspended in ten times the bead volume of Buffer E (20 mM Tris·HCl pH 8.0 and 0.5 M NaCl). The beads bound to the scFv were then divided into two 1 mL polypropylene disposable columns (QIAGEN) and the resin allowed to settle by gravity. Prior to elution, the Ni-NTA agarose resin containing the bound anti-PD-1 scFv was washed in ten column volumes of low imidazole "Wash buffer" (20 mM Tris·HCl pH 8.0, 300 mM NaCl, 10% glycerol, 20 mM imidazole and 0.02% Tween 80). The bound anti-PD-1 scFv was then eluted with 5 mL of "Elution buffer" (20 mM Tris·HCl pH 8.0, 0.3 M NaCl, 10% glycerol, 0.02% Tween 80 and 300 mM imidazole) and ten 0.5 mL fractions were collected. Each Eppendorf collection tube contained 0.5 mL of 2× collection buffer (25 mM Hepes, pH 6.8, 0.4 M NaCl, 100 mM Na citrate dihydrate (pH 6.0), 25% glycerol and 0.02% Tween 80). Fractions containing the highest concentrations of the anti-PD-1 scFv were then dialyzed overnight at 4° C. against 2 L of "Storage buffer" (25 mM HEPES, pH 6.8, 0.125 M NaCl, 0.2 M Mannitol, 21.5 μM EDTA, 0.02% Tween 80, 40 mM Na citrate dihydrate and 20% glycerol). The purified anti-PD-1 scFv (~0.2 mg/mL) was stored at −80° C. until needed.

Example 3. Single-Chain Fv Characterization

Figure 6:
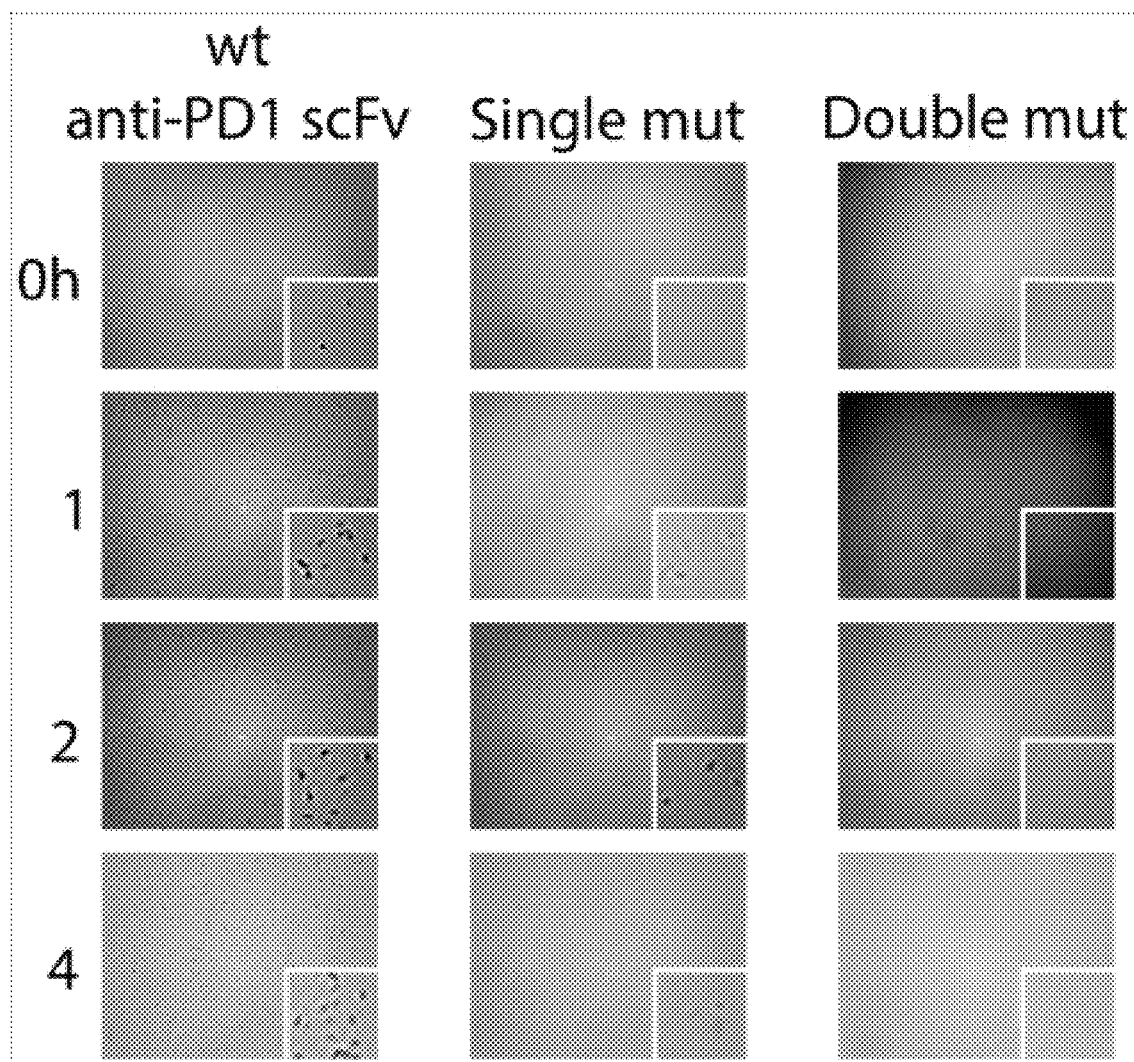

The solubility of the scFv variants were tested. First, solubility in cell culture media was tested, such as, e.g. in the medium RPMI1640. Some results of these solubility studies are shown in FIG. 6. The data showed that the original or wild-type anti-PD-1 scFv forms a precipitate after one hour of incubation (FIG. 6; left column). Moreover, the addition of a small amount of a detergent (e.g., 0.02% Tween 80) did not eliminate the aggregation problem. An identical experiment conducted with the T126R "single mutant" established that there was still detectable precipitation, albeit less than the wild type molecule (lower middle panel). However, the striking result was that even after incubation for 24 hours, no precipitation was detected for the T126R/L124G "double mutant" anti-PD-1dm. Due to a lack of activity in binding to human PD-1, the triple mutant (T126R/L124G/F11G; see FIG. 4) was not chosen to be characterized in a solubility assay. Based on a human PD-1/PD-L1 interaction biochemical assay, it was determined that the triple mutant (T126R/L124G/F11G) did not bind to PD-1.

Based on the results presented in FIG. 6, subsequent studies were focused exclusively on anti-PD-1dm. It was important to determine whether the anti-PD-1dm maintained the critical activities of the original anti-PD-1 scFv; namely, its ability to both bind to PD-1 and to block the PD-1/PD-L1 interaction. Assays were performed to test the ability of the anti-PD-1dm to bind to PD-1 and block PD-L1 signaling and to compare its activities to the original anti-PD-1 scFv from which it was derived.

Figure 7:
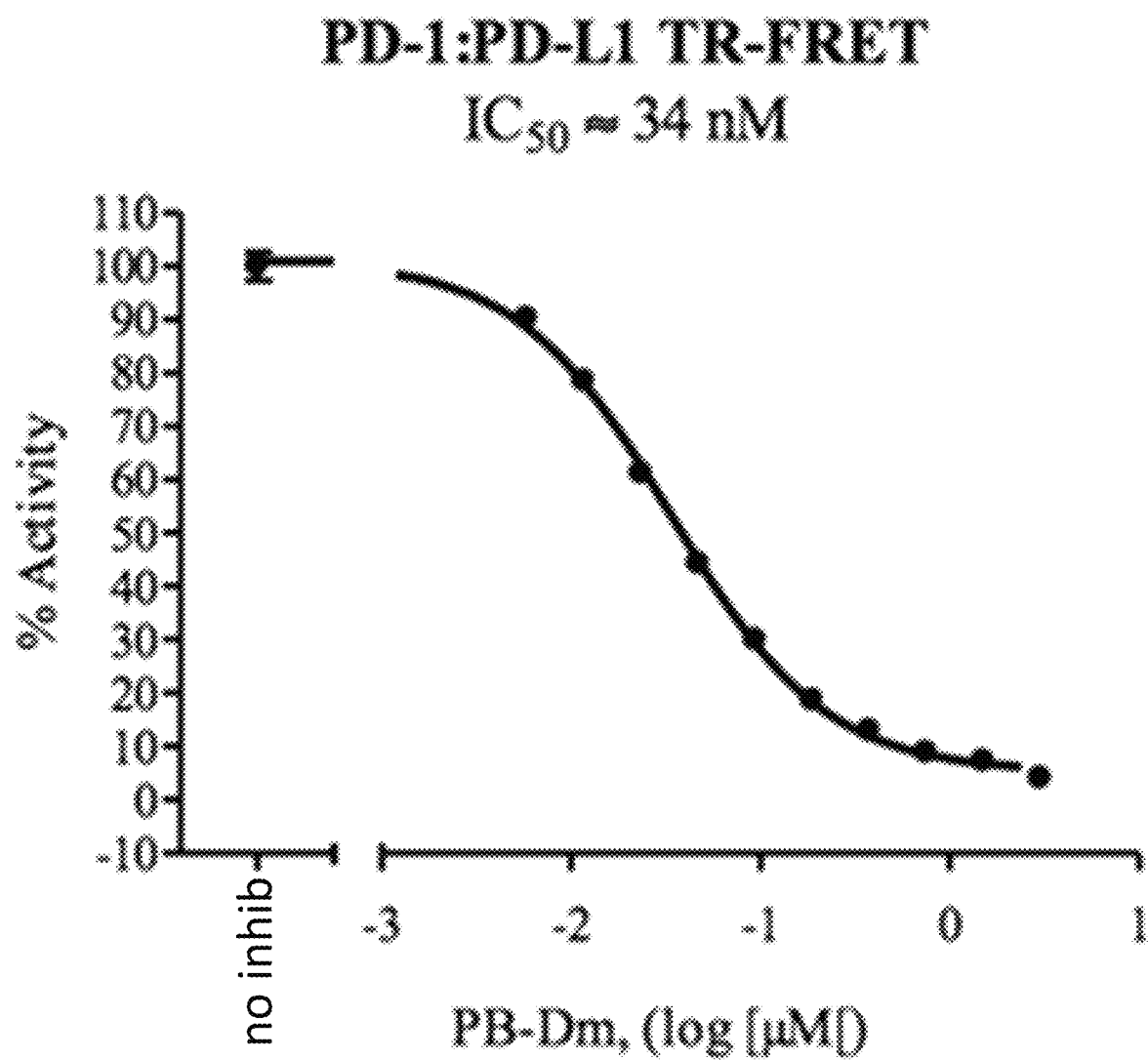

In a biochemical assay, the anti-PD-1dm bound to human PD-1 and inhibited PD-1 interactions with PD-L1 with an IC50 of 34 nM (FIG. 7). In the same assay, the original anti-PD-1 scFv bound to human PD-1 and inhibited PD-1 interactions with PD-L1 with an IC50 of 26 nM (Shin J et al., Protein Expr Purif 177: 105766 (2001)). Thus, the anti-PD-1dm retained the PD-1 antigen binding ability of the anti-PD-1 scFv and a PD-1 inhibitory activity of blocking PD-L1 interacting with PD-1. The equivalent IC50 values for the original and the anti-PD-1dm variant of the anti-PD-1 scFv confirmed the predictions of the CamSol, Aggrescan3D, and PyMOL modeling shown in Example 1. In particular, the Aggrescan3D data uploaded into PyMOL predicted that the anti-PD-1dm double mutant would not result in any changes in the relative positions of CDR amino acid residues relative to the "wildtype."

Figure 8A:
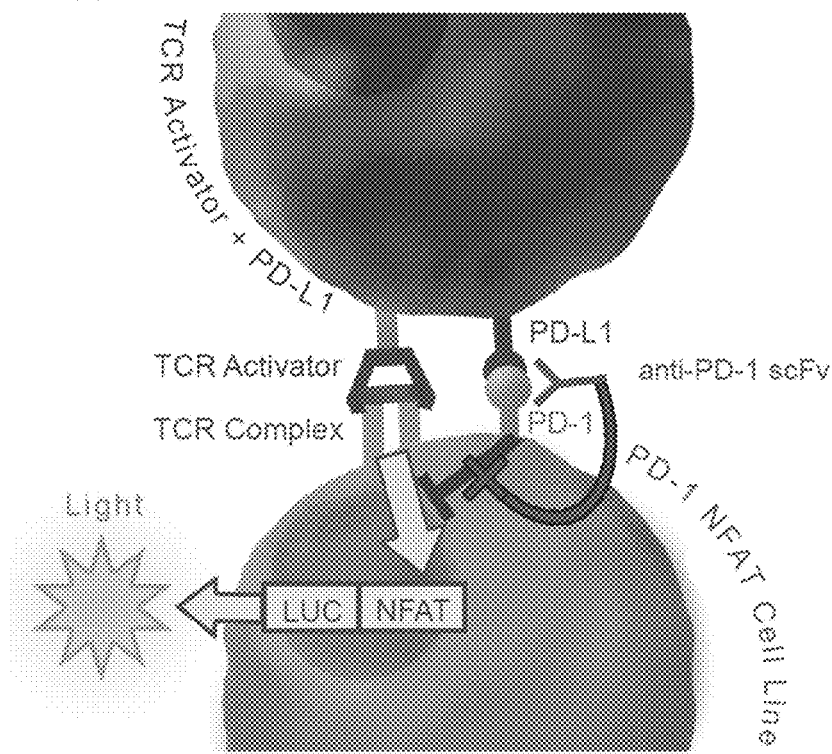
Figure 8B:
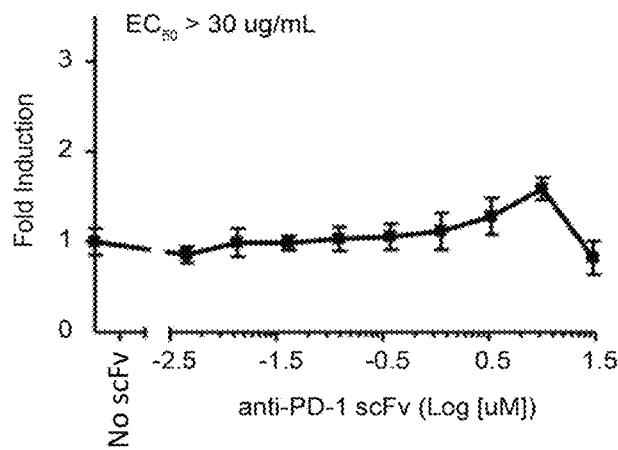

In a cell-based assay, the anti-PD-1dm inhibited the human PD-1/PD-L1 interaction with an EC50 of 42 nM (FIG. 8). The critical feature of the assay depicted in FIG. 8A, which shows that levels of the reporter (i.e., Nuclear Factor of Activated T-cell (NFAT (59, 60); reviewed in (61), linked to luciferase) increase when inhibitors are added that disrupt the interaction between PD-L1 expressed on CHO cells and PD-1 expressed on Jurkat cells. As mentioned previously, the original anti-PD-1 scFv did not produce any positive result in this assay, likely due to a solubility and/or aggregation issues. This assay is based on the interaction of human PD-1 on Jurkat cells (a type of T-cell) with human PD-L1 on PD-L1-expressing CHO cells (a transformed cell line). Briefly, the day prior to conducting the assay, TCR/PD-L1 CHO cells were seeded, at a density of 35,000 cells per well, into a white clear-bottom 96-well microplate in 100 μL of growth media. The next day, the anti-PD-1dm and the control compounds were diluted in assay media (RPMI1640, 10% FBS and 1% Pen/Strep). In addition, the PD-1-NFAT-reporter Jurkat cells were harvested and following centrifugation, re-suspended in assay media (~4×10$^5$ cells/mL). All test samples were then incubated (11 in volume) with the reporter Jurkat cells for forty minutes. After incubation, the media was removed from the CHO cells and 100 μL/well of the reporter-Jurkat/test sample mixture was added to the CHO cells. After 5 hours of treatment, cells were lysed and a luciferase assay was performed.

Figure 8C:
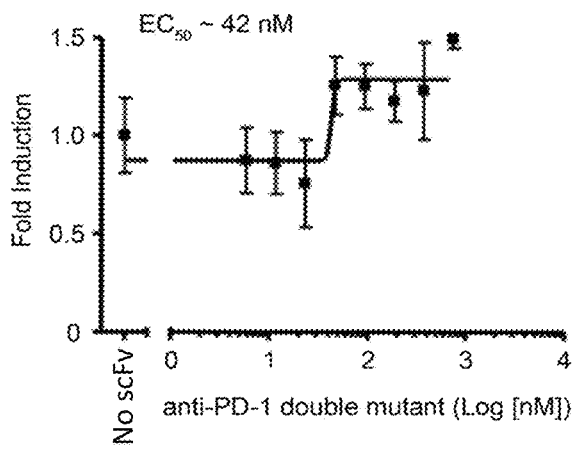

In this cellular assay, the anti-PD-1dm inhibited PD-1 signaling to a T cell via PD-L1 expressed on a transformed cell. After measuring luciferase luminescence values over a range of concentrations it was determined that the wt anti-PD-1 scFv did not function in this assay (it had an EC$_{50}$ of greater than 30 μg/ml (FIG. 8B)). In contrast, an EC$_{50}$ of 42 nM was calculated for the anti-PD-1dm (FIG. 8C). Thus, only the more soluble anti-PD-1dm functioned as a checkpoint inhibitor of the interaction between Jurkat cells expressing PD-1 and transformed cells expressing PD-L1.

Thus, the anti-PD-1dm retained the PD-1 inhibitory activity of nivolumab of inhibiting PD-L1 signaling via PD-1. Given that the key mechanism of nivolumab, a full IgG4 antibody, is based on the disruption of the interaction between PD-1 and its ligands, this finding indicates the potential therapeutic value of the much smaller anti-PD-1dm scFv.

Figure 9:
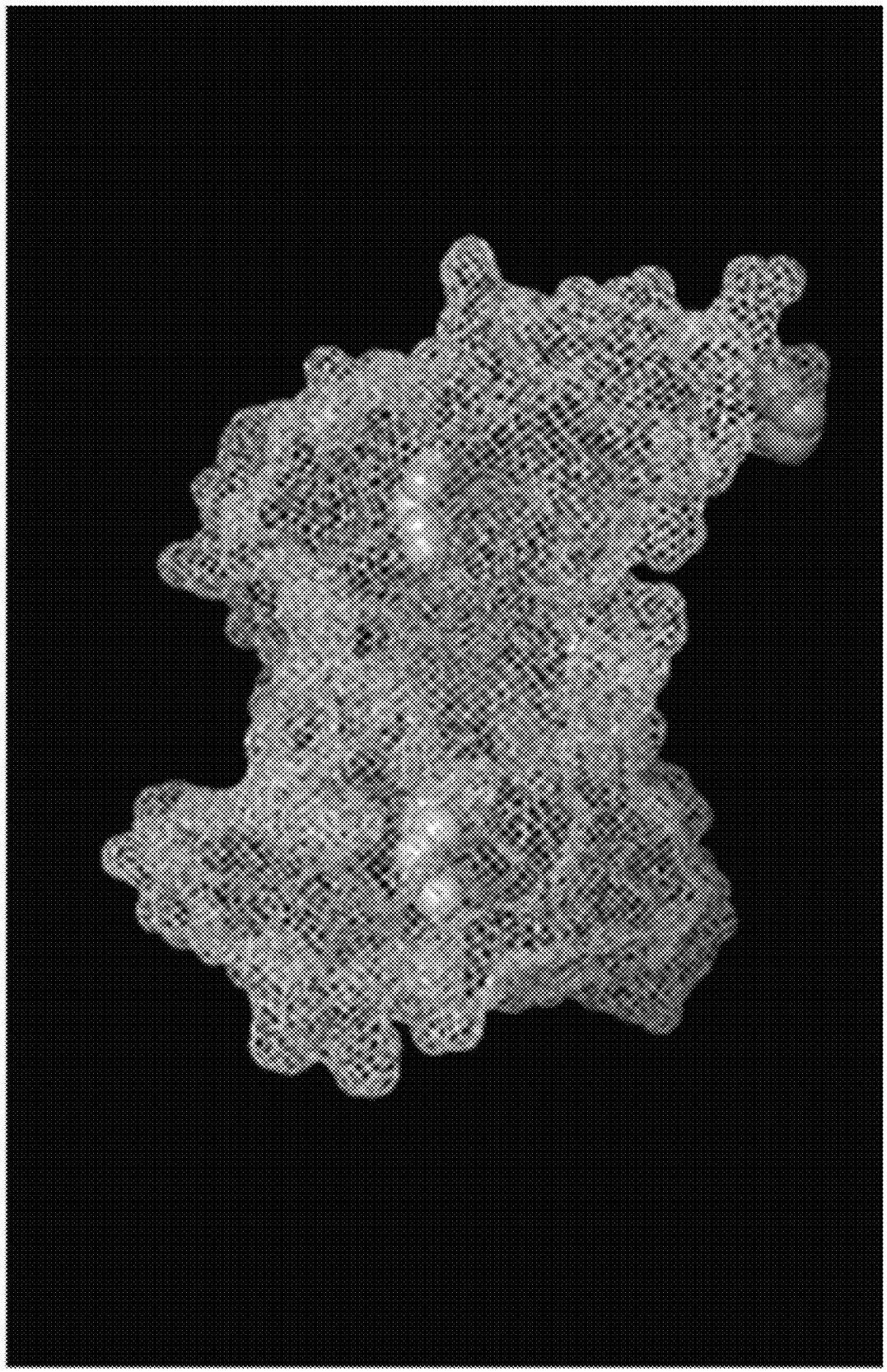

Example 4. Derivatives of Anti-PD-1 Single-Chain Fv Variants Suitable for Cargo Attachment Generation of a derivative of the anti-PD-1dm for use in coupling to other molecules. Using maleimide chemistry, it is straightforward to couple compounds (e.g., fluorescent dyes, drugs, etc.) to proteins, provided there is a cysteine on the surface of the molecule. Anti-PD-1 scFv variants do not have any free cysteine on its surface. Therefore, QuikChange mutagenesis was used to place a cysteine residue (Cys) at the extreme carboxy-terminus of anti-PD-1dm. The resulting molecule, termed "anti-PD-1dm-Cys", was purified and a model generated (FIG. 9).

Figure 10A:
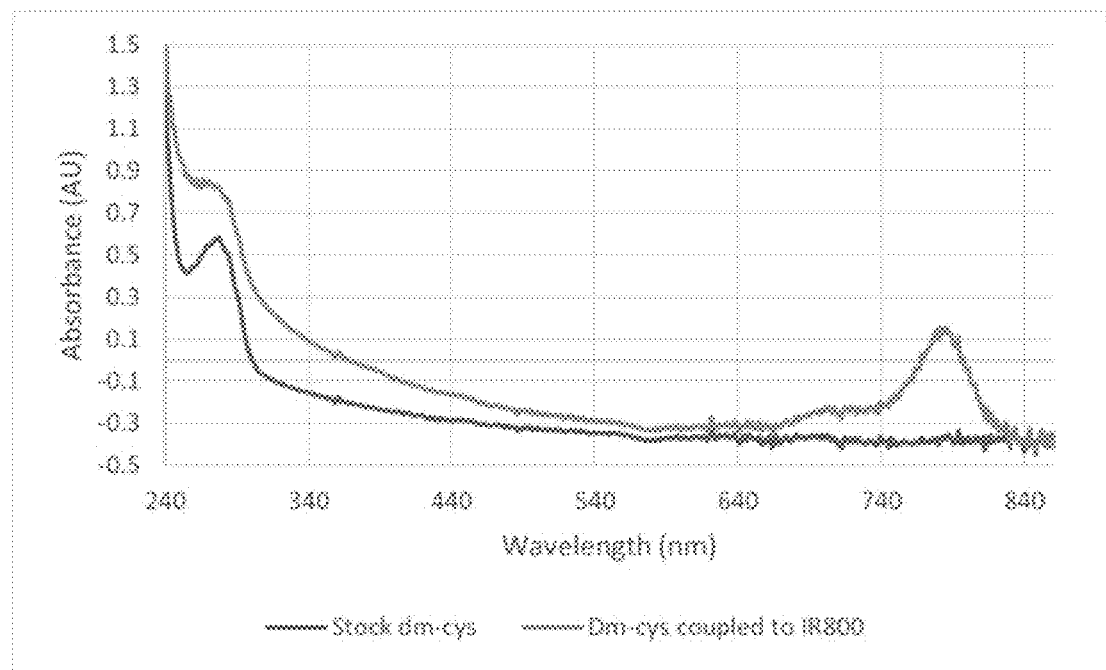
Figure 10B:
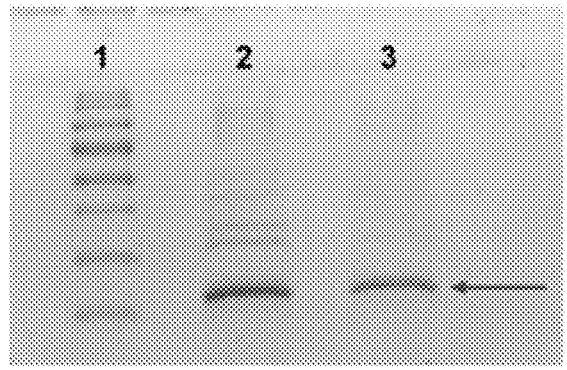

The anti-PD-1dm-Cys can be coupled to other compounds via maleimide chemistry. The anti-PD-1dm-Cys was attached to a maleimide linker and an IR800 cargo using routine maleimide chemical reactions. Following the maleimide reactions, unbound IR800 was removed via chromatography over Zebra Spin Desalting Columns (7K MWCO; Thermo Scientific)). That the anti-PD-1dm-Cys can be labeled via standard maleimide chemistry, with compounds including the near-infrared fluorescent probe IR800 (that is frequently used in animal studies), is demonstrated in FIG. 10. FIG. 10A presents the ultraviolet (UV) and visible (Vis) light spectra, using excitation wavelengths of 280 and 700 nm, of both the unlabeled anti-PD-1 dm-Cys and the anti-PD-1dm-Cys coupled to IR800 via maleimide chemistry. Note, IR800 is excited at 700 nm and emits at 830 nm. FIG. 10A shows UV/Vis spectra of 1) the control or "stock sample" of the anti-PD-1dm-Cys (blue line) and 2) the anti-PD-1dm-Cys coupled to IR800 (red line). Inspection of the "red line" spectrum indicates that the anti-PD-1dm-Cys was coupled to IR800.

Figure 10C:
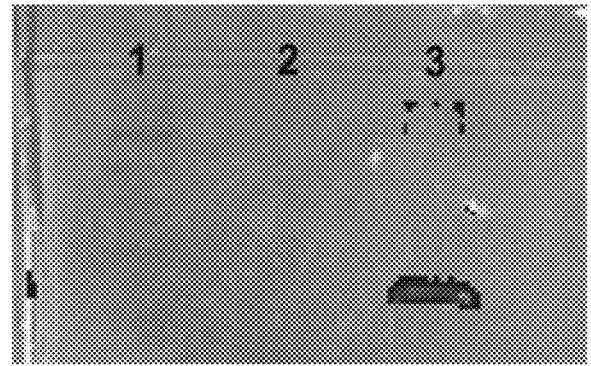

To confirm that IR800 was coupled to the anti-PD-1dm-Cys, 2 µg aliquots of both samples were separated on an SDS-PAGE gel (FIG. 10B); the location of the approximately 27 kDa anti-PD-1dm-Cys is indicated by the arrow. Protein Size Markers (Broad Range; NEB) were loaded in lane 1, an aliquot of stock anti-PD-1dm-Cys was loaded in lane 2 while an aliquot of the anti-PD-1dm-Cys coupled to IR800 was loaded on lane 3. The gel was then subsequently subjected to fluorescence analysis using a Xenogen IVIS 200 Biophotonic Imager (FIG. 10C). As expected, the untreated anti-PD-1dm-Cys lacked a fluorescent signal (lane 2) while the anti-PD-1dm-Cys coupled to IR800 had a strong fluorescent signal (lane 3). In summary, the data in FIG. 10 establishes that the anti-PD-1dm-Cys is readily coupled to compounds, such as IR800, via maleimide chemistry.

Example 5. PD-1 Detection with the Anti-PD-1dm Single-Chain Fv

The anti-PD-1dm scFv represents a new platform for use in detecting PD-1. A fusion protein (SEQ ID NO: 15) containing the anti-PD-1dm scFv fused to super-folded (sf) GFP (SEQ ID NO: 33) was generated and tested for its ability to detect PD-1 on the surface of cells via immunofluorescence and flow cytometry.

An expression plasmid encoding the anti-PD-1dm::sfGFP fusion protein was transformed into Rosetta-Gami™ E. coli, and expression was induced during culture using IPTG. When analyzed by SDS-PAGE, a protein of the expected molecular weight of the fusion protein was observed. Moreover, the fusion protein bound to Ni-NTA agarose beads. This anti-PD-1dm scFv-GFP fusion protein may be used as a reagent for measuring human PD-1 levels expressed by different cell types.

In particular, the anti-PD-1dm scFv-GFP fusion protein may be used in two assays: (A) Histopathology of tumor biopsies: For patients with solid tumors, anti-PD-1 immunotherapy is only viable if PD-1 containing T-cells are present in the tumor. Therefore, upon obtaining a tumor biopsy, the fluorescently labeled anti-PD-1dm-sfGFP may be used to determine if PD-1 containing T-cells are present (via standard fluorescent microscopy techniques). If so, then immunotherapy with anti-PD-1 antibodies is a viable option. (B) Liquid Biopsy-Based PD-1 detection: A recent study established that expansion of T cell clones within tumors is paralleled by their expansion within the peripheral blood (Wu T et al., Nature 579: 274-8 (2020)). Furthermore, it was reported that patients with T cell clonotypic expansion respond better to PD-1 checkpoint blockade (Wu T et al., Nature 579: 274-8 (2020)). Therefore, molecular profiling of peripheral T cells in blood may serve as a valuable assay for management of cancer patients (Kilgour E et al., Cancer Cell 37: 485-95 (2020)). The fluorescently labeled anti-PD-1dm-sfGFP may be used in flow cytometry studies designed to detect PD-1 positive T-cells in blood samples.

Figure 16:
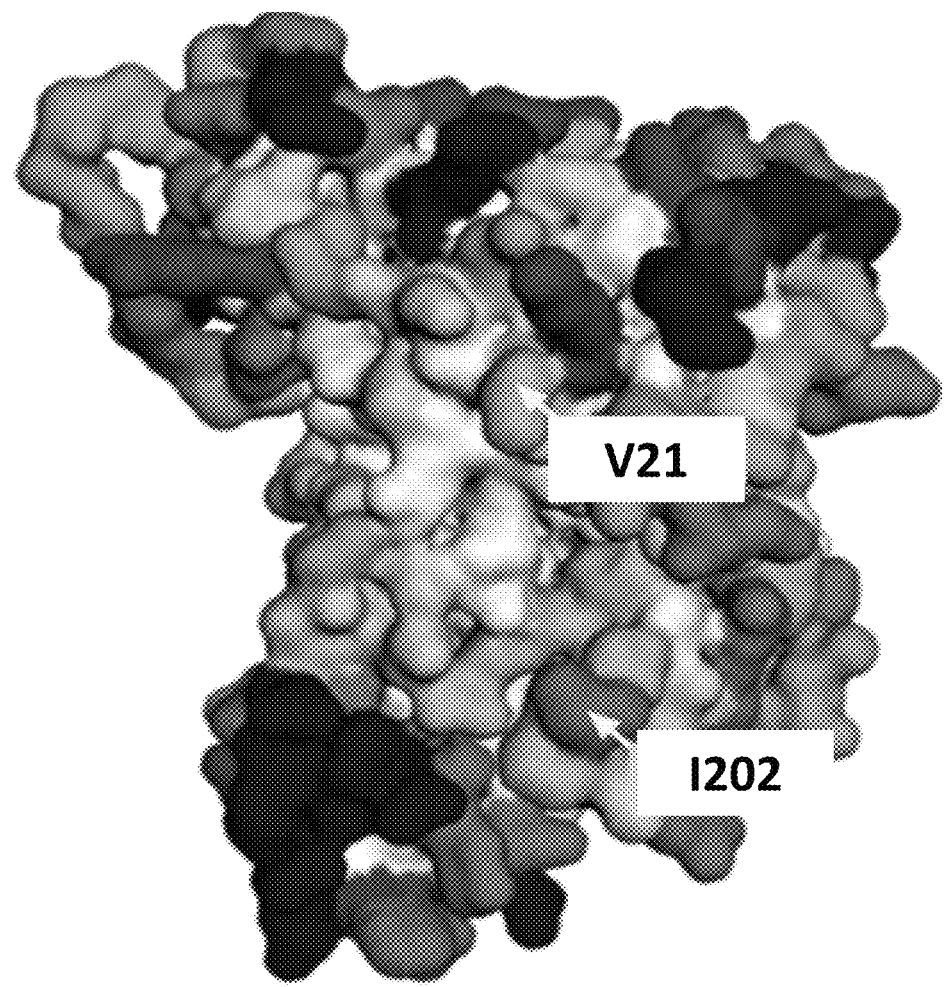
FIG. 16 shows a depiction of residue I202 on the surface of the anti-PD-1-dm derived from an Aggrescan 3D analyses. Also shown is residue V21 derived from the same Aggrescan 3D analyses. The more positive the A3D score, the higher the aggregation propensity (i.e., the deeper the red color).

Example 6. Additional Variants of the Anti-PD-1dm Single-Chain Fv Have Improved Solubility Additional residues in the anti-PD-1 scFv were assessed to determine if its solubility would be improved. Due to its A3D score of 1.3035, Ile 202 was considered a top candidate. A depiction of residue I202 on the surface of the anti-PD-1-dm (L124G, T126R) derived from an Aggrescan 3D analyses is shown at FIG. 16. An expression vector having the I202R mutation was prepared, and an anti-PD-1-tm ("tri-mutant") containing the L124G, T126R, I202R mutations was purified and analyzed by BPSBiosciences. However, the I202R anti-PD1-tm did not bind to PD-1 (presumably because the CDR was disrupted by the mutation). An additional round of molecular modeling studies indicated that the more conservative I202D mutation might work. However, the I202D anti-PD-1-tm was also inactive.

Figure 11A:
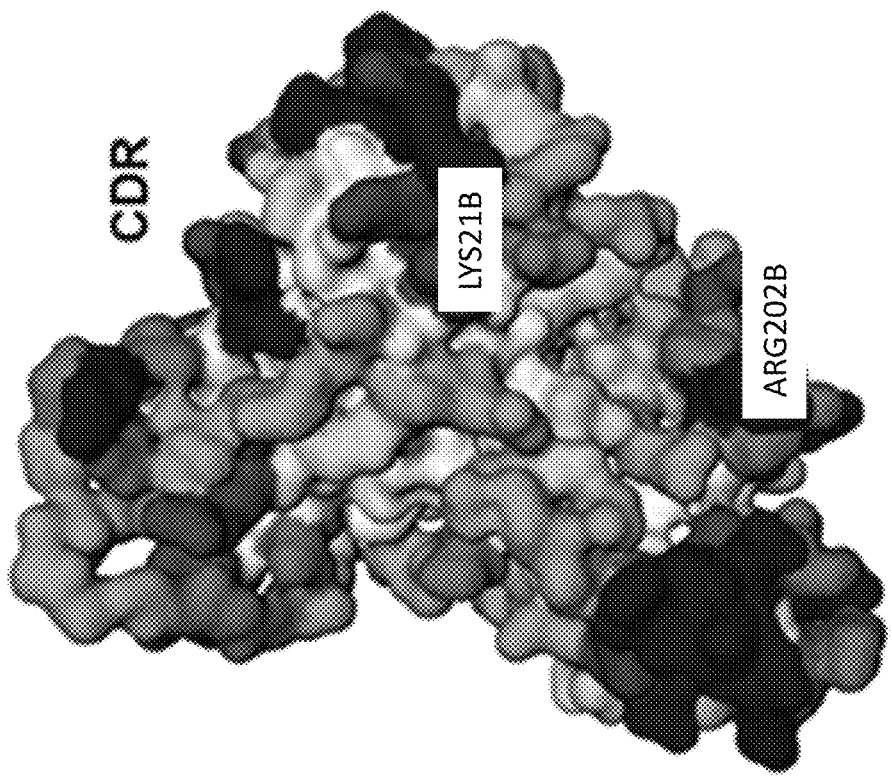

Directed evolution was used to further evolve the anti-PD-1dm scFv. For example, additional modifications can be engineered into the anti-PD-1dm scFv backbone to further improve solubility, stability, and functional properties. The AGGRESCAN 3D program predicted that the two residues in the double mutant anti-PD-1dm with the greatest aggregation propensity were the isoleucine residue at position 202 (discussed above) and the valine at position 21 (see FIG. 11A (left)). Based on several considerations, such as additional PyMOL based studies of potential changes to the CDRs by mutations under consideration and the predicted pI of the resultant mutant molecules determined by the ExPASy WEB site, the candidate mutations I202R and V21K were chosen to be made on the surface of the anti-PD-1dm molecule. The resulting anti-PD-1 scFv variant having V21K, L124G, T126R, and I202R, is referred to herein as anti-PD-1 "tetra mutant" and abbreviated hereafter as "anti-PD-1-tem." Both of the two additional mutations involve substituting a hydrophobic residue with a polar and positively charged residue. Table 2 may be used to coordinate the reference sequences with the mutations. As noted above, L124G in the scFv is position 108 in the nivolumab heavy chain reference sequence. T126G in the scFV is position 110 in the nivolumab heavy chain reference sequence. V21K in the scFV is position 5 in the nivolumab heavy chain reference sequence. I202R in the scFV is position 58 in the nivolumab light chain reference sequence.

Figure 11B:
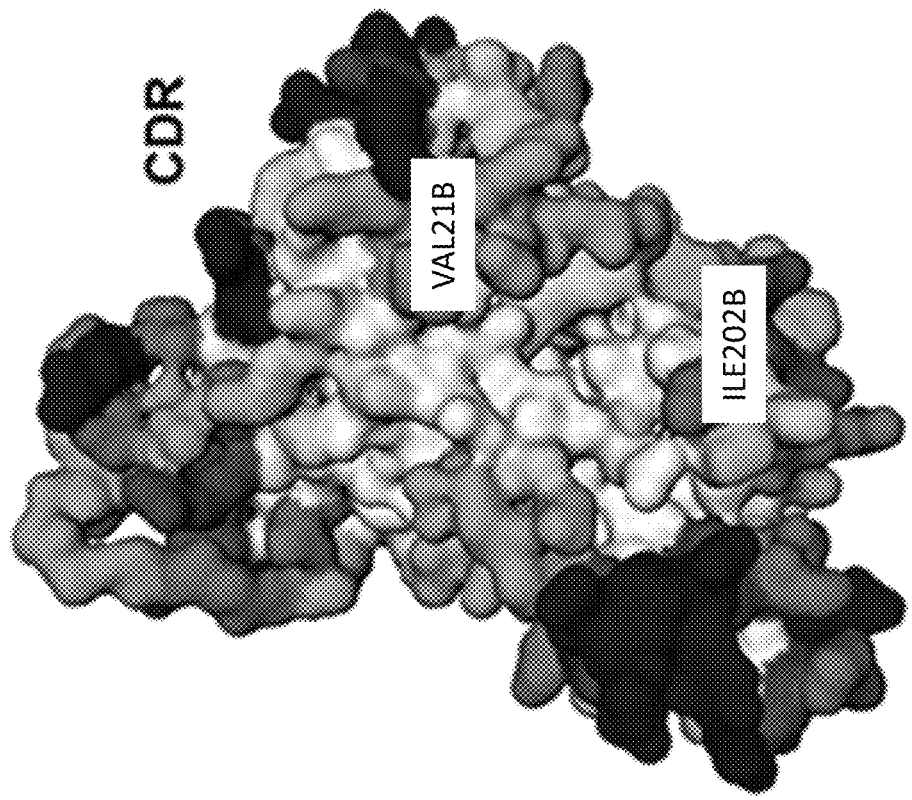
Figure 12:
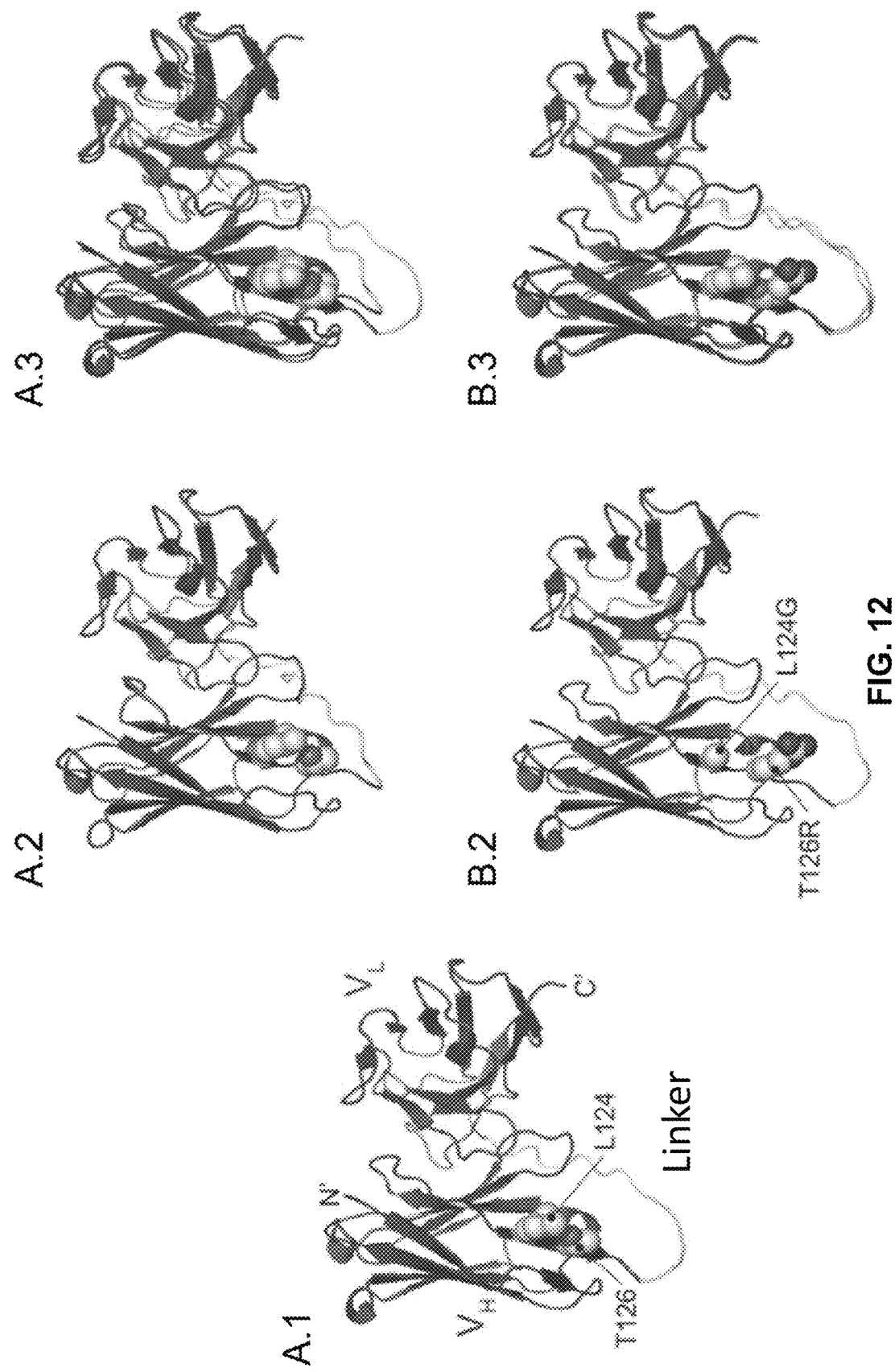
Figure 14:
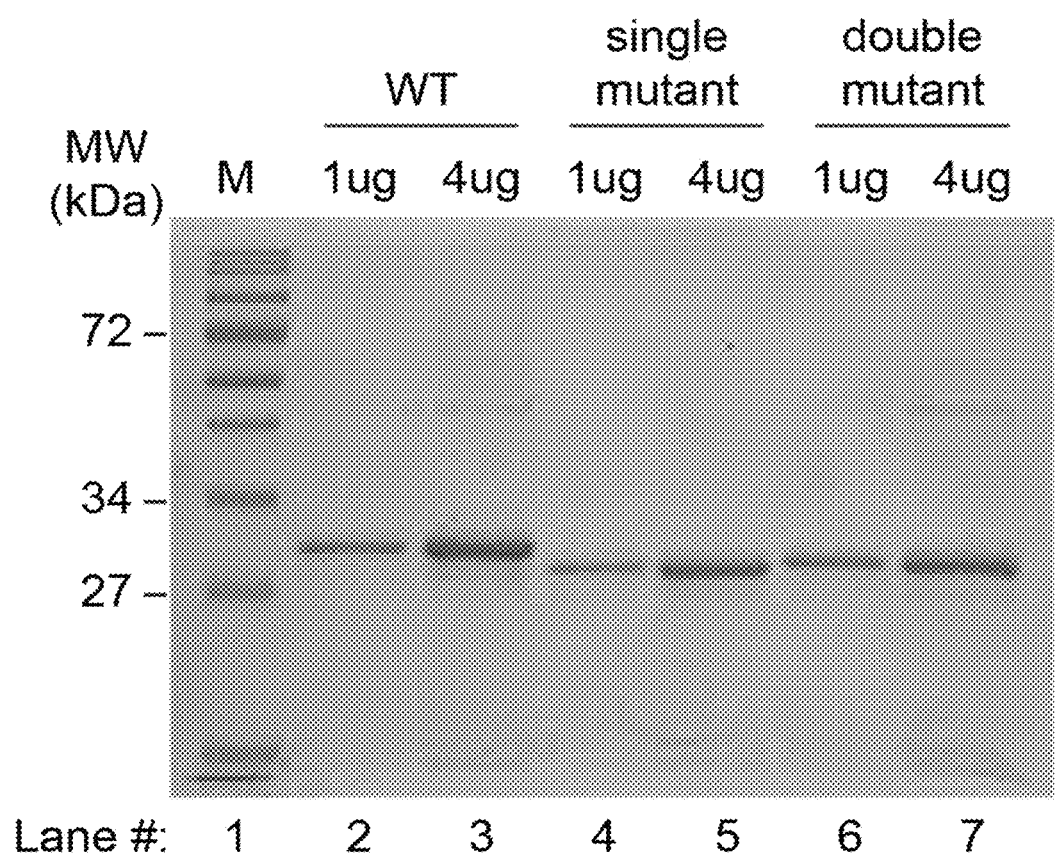
FIG. 14 shows SDS-PAGE analyses of aliquots of the purified anti-PD-1 scFv wild type, single mutant and double mutant. Lane 1 contains "Broad Range" Protein Standards (NEB). Lanes 2 & 3, 1 µg and 4 µg samples of the purified wt anti-PD-1 scFv. Lanes 4 & 5, 1 µg and 4 µg samples of the purified anti-PD-1 single mutant. Lanes 6 & 7, 1 µg and 4 µg samples of the purified anti-PD-1 double mutant.

An Aggrescan3D depiction of the anti-PD-tem structure is shown in FIG. 11B (right). Inspection of the surface of this molecule indicates that two clusters of red residues present on the anti-PD-1dm, indicative of aggregation propensity, have been removed by the I202R and V21K mutations.

Table 2 shows variable domain sequences from nivolumab and polypeptide regions of anti-PD-1 binding scFv constructs shown in the Examples. Table 2 shows the position and amino acid substitution relative to a nivolumab region as numbered in the anti-PD-1 scFv constructs. For example, the anti-PD-1dm "double mutant" has two modifications in its immunoglobulin regions at L124G and T126R (as numbered in the scFv construct) relative to the heavy chain Fv of nivolumab (SEQ ID NO: 24). Similarly, the anti-PD-1tm "tetra mutant" has four modifications in its immunoglobulin regions at V21K, L124G, T126R, and I202R as numbered in the scFv construct. The anti-PD-1tem "tetra mutant" has three modifications in its heavy chain immunoglobulin region at V21K, L124G, and T126R (as numbered in the scFv construct) relative to the heavy chain Fv of nivolumab (SEQ ID NO: 24), and one modification in its light chain immunoglobulin region at I202R (as numbered in the scFv construct) relative to the heavy chain variable region (HV) of nivolumab (SEQ ID NO: 30).

TABLE 2

Immunoglobulin Amino Acid Residue Changes as Numbered in the Examples. The CDRs are in bold type. The mutations are underlined.

| | immunoglobulin polypeptide sequence |
|---|---|
| nivolumab HV reference V5, L108, and T110 | QVQLVESGGGVVQPGRSLRLDCKASGITFSNSGMHWVRQAPG KGLEWVAVIWYDGSKRYYADSVKGRFTISRDNSKNTLFLQMN SLRAEDTAVYYCATNDDYWGQGTLVTVSS (SEQ ID NO: 24) |
| anti-PD-1dmmodified at positions L124G and T126R | VQLVESGGGVVQPGRSLRLDCKASGITFSNSGMHWVRQAPGK GLEWVAVIWYDGSKRYYADSVKGRFTISRDNSKNTLFLQMNS LRAEDTAVYYCATNDDYWGQGTGVRVSS (SEQ ID NO: 8) |
| anti-PD-1tm modified at positions V21K, L124G, and T126R | VQLKESGGGVVQPGRSLRLDCKASGITFSNSGMHWVRQAPGK GLEWVAVIWYDGSKRYYADSVKGRFTISRDNSKNTLFLQMNS LRAEDTAVYYCATNDDYWGQGTGVRVSS (SEQ ID NO: 16) |
| nivolumab LV reference I58 | EIVLTQSPATLSLSPGERATLSCRASQSVSSYLAWYQQKPGQAP RLLIYDASNRATGIPARFSGSGSGTDFTLTISSLEPEDFAVYYCQ QSSNWPRTFGQGTKVEIK (SEQ ID NO: 30) |
| anti-PD-1tm modified at position I202R | EIVLTQSPATLSLSPGERATLSCRASQSVSSYLAWYQQKPGQAP RLLIYDASNRATGRPARFSGSGSGTDFTLTISSLEPEDFAVYYCQ QSSNWPRTFGQGTKVEIKR (SEQ ID NO: 17) |

Tables 1 and 2 show that L124G and T126R in anti-PD-1dm correspond respectively to the substitutions L108G and T110R in the reference sequence SEQ ID NO: 24, the heavy chain variable domain of nivolumab. As shown in Tables 1 and 2, V21K, L124G, and T126R, in anti-PD-1tm correspond respectively to the substitutions V5K, L108G, and T110R in the heavy chain variable domain of nivolumab SEQ ID NO: 24. As shown in Tables 1 and 2, I202R in anti-PD-1tm corresponds to the substitution I58R in the light chain variable domain (LV) of nivolumab SEQ ID NO: 30.

REFERENCES

1. Shin J, Phelan P J, Gjoerup O, Bachovchin W, Bullock P A. 2021. Characterization of a single chain variable fragment of Nivolumab that targets PD-1 and blocks PD-L1 binding. Protein Expression and Purification 177: 105766.
2. Sormanni P, Aprile F A, Vendruscolo M. 2015. The CamSol Method of Rational Design of Protein Mutants with Enhanced Solubility. J Mol Biol 427:478-490.
3. Lee J Y, Lee H T, Shin W, Chae J, Choi J, Kim S H, Lim H, Won Heo T, Park K Y, Lee Y J, Ryu S E, Son J Y, Lee J U, Heo Y S. 2016. Structural basis of checkpoint blockade by monoclonal antibodies in cancer immunotherapy. Nat Commun 7:13354.
4. Zambrano R, Jamroz M, Szczasiuk A, Pujols J, Kmiecik S, Ventura S. 2015. AGGRESCAN3D (A3D): server for prediction of aggregation properties of protein structures. Nucleic Acids Res 43:10.1093.
5. Kuriata A, Iglesias V, Pujols J, Kurcinski M, Kmiecik S, Ventura S. 2019. Aggrescan3D(A3D) 2.0: prediction and engineering of protein solubility. Nucleic Acids Res 47:10.1093.
6. Wu T D, Madireddi S, de Almeida P E, Banchereau R, et. a. 2020. Perifpheral T cell expansion predicts tumor infiltration and clinical response. Nature 579:274-278.
7. Kilgour E, Rothwell D G, Brady G, Dive C. 2020. Liquid Biopsy-Based Biomarkers of Treatment Response and Resistance. Cancer Cell 37:485-495.
9. Niemeijer A N, Leung D, Huisman M C, Bahce I, Hoekstra O S, van Dongen GAMS, Boellaard R, Du S, Hayes W, Smith R, Windhorst A D, Hendrikse N H, Poot A, Vugts D J, Thunnissen E, Morin P, Lipovsek D, Donnelly D J, Bonacorsi S J, Velasquez L M, de Gruijl T D, Smit E F, De Langen A J. 2018. Whole body PD-1 and P D-L1 positron emission tomography in patients with non-small-cell lung cancer. Nature Communications 10.1038:s41467-018.
10. Sun X, Zhang A, Baker B, Sun L, Howard A, et. a. 2011. Development of SNAP-Tag Fluorogenic Probes for Wash-Free Fluorescence Imaging. Chembiochem 12:2217-2226.
12. Kohl J, Ng J, Cachero S, Ciabatti E, Dolan M-J, Sutcliffe B, Tozer A, Ruehle S, Krueger D, Frechter S, Branco T, Tripodi M, Jefferis SXE. 2014. Ultrafast tissue staining with chemical tags. PNAS:E3805-3814.
13. Celis-Gutierrez J, Blattmann P, Zhai Y, Roncagalli R, Gstaiger M, Malissen B. 2019. Quantitative Interactomics in Primary T Cells Provides a Rationale for Concomitant PD-1 and BTLA Coinhibitor Blockade in Cancer Immunotherapy. Cell Reports 27:3315-3330.
14. Mirdita M, Schutze K, Moriwaki Y, Heo L, Ovchinnikov S, Steinegger M. 2021. ColabFold-Making protein folding accessible to all. Research Square https://doi.org/10.21203/rs.3.rs-1032816/v1.
15. Baek M, DiMaio F, Anishchenko I, Dauparas J, Ovchinnikov S, al. e. 2021. Accurate prediction of protein structures and interactions using a three-track neural network. Science 373:871-876.
16. Waterhouse A, Bertoni M, Bienert S, Studer G, Tauriello G, Gumienny R, Heer F T, de Beer TAP, Rempfer C, Bordoli L, Lepore R, Schwede T. 2018. SWISS-MODEL: homology modelling of protein structures and complexes. Nucleic Acids Res 46:W296-W303.

I claim:

1. A PD-1 binding protein comprising:
   a) a heavy chain variable domain comprising:
      1) A heavy chain CDR-1 comprising the sequence NSGMH (SEQ ID NO: 2),
      2) A heavy chain CDR-2 comprising the sequence VIWYDGSKRYYADSVKG (SEQ ID NO: 3), and
      3) A heavy chain CDR-3 comprising the sequence NDDY (SEQ ID NO: 4); and
   b) a light chain variable domain comprising:
      1) A light chain CDR-1 comprising the sequence RASQSVSSYLA (SEQ ID NO: 5),
      2) A light chain CDR-2 comprising the sequence DASNRAT (SEQ ID NO: 6), and
      3) A light chain CDR-3 comprising the sequence QQSSNWPRT (SEQ ID NO: 7);
   wherein the heavy chain variable domain comprises a glycine at position 108 and/or an arginine at position 110 relative to SEQ ID NO: 24.

2. The PD-1 binding protein of claim 1, wherein the light chain variable domain comprises an arginine at position 58 relative to SEQ ID NO: 29; and/or wherein the heavy chain variable domain further comprises a lysine at position 5 relative to SEQ ID NO: 24.

3. The PD-1 binding protein of claim 1, comprising a polypeptide with a sequence having at least 90%, at least 95%, at least 96%, at least 97%, at least 98%, or at least 99% sequence identity to any one of SEQ ID NOs: 8-21.

4. The PD-1 binding protein of claim 1, wherein the heavy chain variable domain comprises a polypeptide comprising SEQ ID NO: 8 or 16.

5. The PD-1 binding protein of claim 1, wherein the light chain variable domain comprises a polypeptide comprising SEQ ID NO: 9 or 17.

6. A PD-1 binding protein comprising the polypeptide sequence of any one of SEQ ID NOs: 10-11, 14-15, 18-19, and 21.

7. A composition comprising a) the PD-1 binding protein of claim 1; and
   b) a pharmaceutically acceptable carrier or excipient.

8. A polynucleotide encoding the PD-1 binding protein of claim 1.

9. An expression vector comprising the polynucleotide according to claim 8.

10. A host cell comprising a polynucleotide according to claim 8.

11. A kit comprising the PD-1 binding protein of claim 1; and
    b) a device or at least one additional reagent.

12. A method of treatment, the method comprising administering to a subject in need thereof a therapeutically effective amount of a PD-1 binding protein of claim 1.

13. A method of detecting human PD-1 in a sample, the method comprising (i) contacting the sample in vitro with the PD-1 binding protein of claim 1, and
    (ii) detecting the PD-1 binding protein.

14. A method of detecting human PD-1, the method comprising (i) administering to a subject a PD-1 binding protein of claim 1, and
    (ii) detecting the PD-1 binding protein.

* * * * *

SEQUENCE LISTING

```
Sequence total quantity: 76
SEQ ID NO: 1               moltype = AA  length = 288
FEATURE                    Location/Qualifiers
source                     1..288
                           mol_type = protein
                           organism = Homo sapiens
SEQUENCE: 1
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL               288

SEQ ID NO: 2               moltype = AA  length = 5
FEATURE                    Location/Qualifiers
source                     1..5
                           mol_type = protein
                           organism = synthetic construct
SEQUENCE: 2
NSGMH                                                                 5

SEQ ID NO: 3               moltype = AA  length = 17
FEATURE                    Location/Qualifiers
source                     1..17
                           mol_type = protein
                           organism = synthetic construct
SEQUENCE: 3
VIWYDGSKRY YADSVKG                                                   17

SEQ ID NO: 4               moltype = AA  length = 4
FEATURE                    Location/Qualifiers
source                     1..4
                           mol_type = protein
                           organism = synthetic construct
SEQUENCE: 4
NDDY                                                                  4

SEQ ID NO: 5               moltype = AA  length = 11
FEATURE                    Location/Qualifiers
source                     1..11
                           mol_type = protein
                           organism = synthetic construct
SEQUENCE: 5
RASQSVSSYL A                                                         11

SEQ ID NO: 6               moltype = AA  length = 7
FEATURE                    Location/Qualifiers
source                     1..7
                           mol_type = protein
                           organism = synthetic construct
SEQUENCE: 6
DASNRAT                                                               7

SEQ ID NO: 7               moltype = AA  length = 9
FEATURE                    Location/Qualifiers
source                     1..9
                           mol_type = protein
                           organism = synthetic construct
SEQUENCE: 7
QQSSNWPRT                                                             9

SEQ ID NO: 8               moltype = AA  length = 112
FEATURE                    Location/Qualifiers
source                     1..112
                           mol_type = protein
                           organism = synthetic construct
SEQUENCE: 8
VQLVESGGGV VQPGRSLRLD CKASGITFSN SGMHWVRQAP GKGLEWVAVI WYDGSKRYYA    60
DSVKGRFTIS RDNSKNTLFL QMNSLRAEDT AVYYCATNDD YWGQGTGVRV SS           112

SEQ ID NO: 9               moltype = AA  length = 108
FEATURE                    Location/Qualifiers
source                     1..108
                           mol_type = protein
                           organism = synthetic construct
SEQUENCE: 9
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIKR                108
```

```
SEQ ID NO: 10            moltype = AA   length = 235
FEATURE                  Location/Qualifiers
source                   1..235
                         mol_type = protein
                         organism = synthetic construct
SEQUENCE: 10
VQLVESGGGV VQPGRSLRLD CKASGITFSN SGMHWVRQAP GKGLEWVAVI WYDGSKRYYA    60
DSVKGRFTIS RDNSKNTLFL QMNSLRAEDT AVYYCATNDD YWGQGTGVRV SSGGGGSGGG   120
GSGGGGSEIV LTQSPATLSL SPGERATLSC RASQSVSSYL AWYQQKPGQA PRLLIYDASN   180
RATGIPARFS GSGSGTDFTL TISSLEPEDF AVYYCQQSSN WPRTFGQGTK VEIKR        235

SEQ ID NO: 11            moltype = AA   length = 236
FEATURE                  Location/Qualifiers
source                   1..236
                         mol_type = protein
                         organism = synthetic construct
SEQUENCE: 11
VQLVESGGGV VQPGRSLRLD CKASGITFSN SGMHWVRQAP GKGLEWVAVI WYDGSKRYYA    60
DSVKGRFTIS RDNSKNTLFL QMNSLRAEDT AVYYCATNDD YWGQGTGVRV SSGGGGSGGG   120
GSGGGGSEIV LTQSPATLSL SPGERATLSC RASQSVSSYL AWYQQKPGQA PRLLIYDASN   180
RATGIPARFS GSGSGTDFTL TISSLEPEDF AVYYCQQSSN WPRTFGQGTK VEIKRC       236

SEQ ID NO: 12            moltype = AA   length = 236
FEATURE                  Location/Qualifiers
source                   1..236
                         mol_type = protein
                         organism = synthetic construct
SEQUENCE: 12
MVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTGVR VSSGGGGSGG   120
GGSGGGGSEI VLTQSPATLS LSPGERATLS CRASQSVSSY LAWYQQKPGQ APRLLIYDAS   180
NRATGIPARF SGSGSGTDFT LTISSLEPED FAVYYCQQSS NWPRTFGQGT KVEIKR       236

SEQ ID NO: 13            moltype = AA   length = 240
FEATURE                  Location/Qualifiers
source                   1..240
                         mol_type = protein
                         organism = synthetic construct
SEQUENCE: 13
GAASQVQLVE SGGGVVQPGR SLRLDCKASG ITFSNSGMHW VRQAPGKGLE WVAVIWYDGS    60
KRYYADSVKG RFTISRDNSK NTLFLQMNSL RAEDTAVYYC ATNDDYWGQG TGVRVSSGGG   120
GSGGGGSGGG GSEIVLTQSP ATLSLSPGER ATLSCRASQS VSSYLAWYQQ KPGQAPRLLI   180
YDASNRATGI PARFSGSGSG TDFTLTISSL EPEDFAVYYC QQSSNWPRTF GQGTKVEIKR   240

SEQ ID NO: 14            moltype = AA   length = 246
FEATURE                  Location/Qualifiers
source                   1..246
                         mol_type = protein
                         organism = synthetic construct
SEQUENCE: 14
GAASQVQLVE SGGGVVQPGR SLRLDCKASG ITFSNSGMHW VRQAPGKGLE WVAVIWYDGS    60
KRYYADSVKG RFTISRDNSK NTLFLQMNSL RAEDTAVYYC ATNDDYWGQG TGVRVSSGGG   120
GSGGGGSGGG GSEIVLTQSP ATLSLSPGER ATLSCRASQS VSSYLAWYQQ KPGQAPRLLI   180
YDASNRATGI PARFSGSGSG TDFTLTISSL EPEDFAVYYC QQSSNWPRTF GQGTKVEIKR   240
ENLYFQ                                                              246

SEQ ID NO: 15            moltype = AA   length = 497
FEATURE                  Location/Qualifiers
source                   1..497
                         mol_type = protein
                         organism = synthetic construct
SEQUENCE: 15
HHHHHHENLY FQGAASQVQL VESGGGVVQP GRSLRLDCKA SGITFSNSGM HWVRQAPGKG    60
LEWVAVIWYD GSKRYYADSV KGRFTISRDN SKNTLFLQMN SLRAEDTAVY YCATNDDYWG   120
QGTGVRVSSG GGGSGGGGSG GGGSEIVLTQ SPATLSLSPG ERATLSCRAS QSVSSYLAWY   180
QQKPGQAPRL LIYDASNRAT GIPARFSGSG SGTDFTLTIS SLEPEDFAVY YCQQSSNWPR   240
TFGQGTKVEI KRENLYFQGM SKGEEELFTGV VPILVELDGD VNGHKFSVRG EGEGDATNGK   300
LTLKFICTTG KLPVPWPTLV TTLTYGVQCF SRYPDHMKRH DFFKSAMPEG YVQERTISFK   360
DDGTYKTRAE VKFEGDTLVN RIELKGIDFK EDGNILGHKL EYNFNSHNVY ITADKQKNGI   420
KANFKIRHNV EDGSVQLADH YQQNTPIGDG PVLLPDNHYL STQSVLSKDP NEKRDHMVLL   480
EFVTAAGITH GMDELYK                                                  497

SEQ ID NO: 16            moltype = AA   length = 112
FEATURE                  Location/Qualifiers
source                   1..112
                         mol_type = protein
                         organism = synthetic construct
SEQUENCE: 16
```

```
VQLKESGGGV VQPGRSLRLD CKASGITFSN SGMHWVRQAP GKGLEWVAVI WYDGSKRYYA     60
DSVKGRFTIS RDNSKNTLFL QMNSLRAEDT AVYYCATNDD YWGQGTGVRV SS            112

SEQ ID NO: 17           moltype = AA  length = 108
FEATURE                 Location/Qualifiers
source                  1..108
                        mol_type = protein
                        organism = synthetic construct
SEQUENCE: 17
EIVLTQSPAT LSLSPGERAT LSCRASQSVS SYLAWYQQKP GQAPRLLIYD ASNRATGRPA    60
RFSGSGSGTD FTLTISSLEP EDFAVYYCQQ SSNWPRTFGQ GTKVEIKR                108

SEQ ID NO: 18           moltype = AA  length = 235
FEATURE                 Location/Qualifiers
source                  1..235
                        mol_type = protein
                        organism = synthetic construct
SEQUENCE: 18
VQLKESGGGV VQPGRSLRLD CKASGITFSN SGMHWVRQAP GKGLEWVAVI WYDGSKRYYA    60
DSVKGRFTIS RDNSKNTLFL QMNSLRAEDT AVYYCATNDD YWGQGTGVRV SSGGGGSGGG   120
GSGGGGSEIV LTQSPATLSL SPGERATLSC RASQSVSSYL AWYQQKPGQA PRLLIYDASN   180
RATGRPARFS GSGSGTDFTL TISSLEPEDF AVYYCQQSSN WPRTFGQGTK VEIKR        235

SEQ ID NO: 19           moltype = AA  length = 236
FEATURE                 Location/Qualifiers
source                  1..236
                        mol_type = protein
                        organism = synthetic construct
SEQUENCE: 19
VQLKESGGGV VQPGRSLRLD CKASGITFSN SGMHWVRQAP GKGLEWVAVI WYDGSKRYYA    60
DSVKGRFTIS RDNSKNTLFL QMNSLRAEDT AVYYCATNDD YWGQGTGVRV SSGGGGSGGG   120
GSGGGGSEIV LTQSPATLSL SPGERATLSC RASQSVSSYL AWYQQKPGQA PRLLIYDASN   180
RATGRPARFS GSGSGTDFTL TISSLEPEDF AVYYCQQSSN WPRTFGQGTK VEIKRC       236

SEQ ID NO: 20           moltype = AA  length = 236
FEATURE                 Location/Qualifiers
source                  1..236
                        mol_type = protein
                        organism = synthetic construct
SEQUENCE: 20
MVQLKESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTGVR VSSGGGGSGG   120
GGSGGGGSEI VLTQSPATLS LSPGERATLS CRASQSVSSY LAWYQQKPGQ APRLLIYDAS   180
NRATGRPARF SGSGSGTDFT LTISSLEPED FAVYYCQQSS NWPRTFGQGT KVEIKR       236

SEQ ID NO: 21           moltype = AA  length = 252
FEATURE                 Location/Qualifiers
source                  1..252
                        mol_type = protein
                        organism = synthetic construct
MUTAGEN                 21
MUTAGEN                 124
MUTAGEN                 126
MUTAGEN                 202
SEQUENCE: 21
HHHHHHENLY FQGAASQVQL KESGGGVVQP GRSLRLDCKA SGITFSNSGM HWVRQAPGKG    60
LEWVAVIWYD GSKRYYADSV KGRFTISRDN SKNTLFLQMN SLRAEDTAVY YCATNDDYWG   120
QGTGVRVSSG GGGSGGGGSG GGGSEIVLTQ SPATLSLSPG ERATLSCRAS QSVSSYLAWY   180
QQKPGQAPRL LIYDASNRAT GRPARFSGSG SGTDFTLTIS SLEPEDFAVY YCQQSSNWPR   240
TFGQGTKVEI KR                                                      252

SEQ ID NO: 22           moltype = AA  length = 240
FEATURE                 Location/Qualifiers
source                  1..240
                        mol_type = protein
                        organism = synthetic construct
SEQUENCE: 22
GAASQVQLKE SGGGVVQPGR SLRLDCKASG ITFSNSGMHW VRQAPGKGLE WVAVIWYDGS    60
KRYYADSVKG RFTISRDNSK NTLFLQMNSL RAEDTAVYYC ATNDDYWGQG TGVRVSSGGG   120
GSGGGGSGGG GSEIVLTQSP ATLSLSPGER ATLSCRASQS VSSYLAWYQQ KPGQAPRLLI   180
YDASNRATGR PARFSGSGSG TDFTLTISSL EPEDFAVYYC QQSSNWPRTF GQGTKVEIKR   240

SEQ ID NO: 23           moltype = AA  length = 440
FEATURE                 Location/Qualifiers
source                  1..440
                        mol_type = protein
                        organism = synthetic construct
SEQUENCE: 23
QVQLVESGGG VVQPGRSLRL DCKASGITFS NSGMHWVRQA PGKGLEWVAV IWYDGSKRYY    60
```

```
ADSVKGRFTI SRDNSKNTLF LQMNSLRAED TAVYYCATND DYWGQGTLVT VSSASTKGPS    120
VFPLAPCSRS TSESTAALGC LVKDYFPEPV TVSWNSGALT SGVHTFPAVL QSSGLYSLSS    180
VVTVPSSSLG TKTYTCNVDH KPSNTKVDKR VESKYGPPCP PCPAPEFLGG PSVFLFPPKP    240
KDTLMISRTP EVTCVVVDVS QEDPEVQFNW YVDGVEVHNA KTKPREEQFN STYRVVSVLT    300
VLHQDWLNGK EYKCKVSNKG LPSSIEKTIS KAKGQPREPQ VYTLPPSQEE MTKNQVSLTC    360
LVKGFYPSDI AVEWESNGQP ENNYKTTPPV LDSDGSFFLY SRLTVDKSRW QEGNVFSCSV    420
MHEALHNHYT QKSLSLSLGK                                                440

SEQ ID NO: 24           moltype = AA   length = 113
FEATURE                 Location/Qualifiers
source                  1..113
                        mol_type = protein
                        organism = synthetic construct
SEQUENCE: 24
QVQLVESGGG VVQPGRSLRL DCKASGITFS NSGMHWVRQA PGKGLEWVAV IWYDGSKRYY     60
ADSVKGRFTI SRDNSKNTLF LQMNSLRAED TAVYYCATND DYWGQGTLVT VSS           113

SEQ ID NO: 25           moltype = AA   length = 22
FEATURE                 Location/Qualifiers
source                  1..22
                        mol_type = protein
                        organism = synthetic construct
SEQUENCE: 25
QVQLVESGGG VVQPGRSLRL DC                                              22

SEQ ID NO: 26           moltype = AA   length = 22
FEATURE                 Location/Qualifiers
source                  1..22
                        mol_type = protein
                        organism = synthetic construct
SEQUENCE: 26
QVQLKESGGG VVQPGRSLRL DC                                              22

SEQ ID NO: 27           moltype = AA   length = 11
FEATURE                 Location/Qualifiers
source                  1..11
                        mol_type = protein
                        organism = synthetic construct
SEQUENCE: 27
WGQGTLVTVS S                                                          11

SEQ ID NO: 28           moltype = AA   length = 11
FEATURE                 Location/Qualifiers
source                  1..11
                        mol_type = protein
                        organism = synthetic construct
SEQUENCE: 28
WGQGTGVRVS S                                                          11

SEQ ID NO: 29           moltype = AA   length = 214
FEATURE                 Location/Qualifiers
source                  1..214
                        mol_type = protein
                        organism = synthetic construct
SEQUENCE: 29
EIVLTQSPAT LSLSPGERAT LSCRASQSVS SYLAWYQQKP GQAPRLLIYD ASNRATGIPA     60
RFSGSGSGTD FTLTISSLEP EDFAVYYCQQ SSNWPRTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 30           moltype = AA   length = 107
FEATURE                 Location/Qualifiers
source                  1..107
                        mol_type = protein
                        organism = synthetic construct
SEQUENCE: 30
EIVLTQSPAT LSLSPGERAT LSCRASQSVS SYLAWYQQKP GQAPRLLIYD ASNRATGIPA     60
RFSGSGSGTD FTLTISSLEP EDFAVYYCQQ SSNWPRTFGQ GTKVEIK                  107

SEQ ID NO: 31           moltype = AA   length = 32
FEATURE                 Location/Qualifiers
source                  1..32
                        mol_type = protein
                        organism = synthetic construct
SEQUENCE: 31
GIPARFSGSG SGTDFTLTIS SLEPEDFAVY YC                                   32

SEQ ID NO: 32           moltype = AA   length = 32
FEATURE                 Location/Qualifiers
```

```
source                          1..32
                                mol_type = protein
                                organism = synthetic construct
SEQUENCE: 32
GRPARFSGSG SGTDFTLTIS SLEPEDFAVY YC                                      32

SEQ ID NO: 33                   moltype = AA  length = 370
FEATURE                         Location/Qualifiers
source                          1..370
                                mol_type = protein
                                organism = synthetic construct
SEQUENCE: 33
SKGEELFTGV VPILVELDGD VNGHKFSVRG EGEGDATNGK LTLKFICTTG KLPVPWPTLV         60
TTLTYGVQCF SRYPDHMKRH DFFKSAMPEG YVQERTISFK DDGTYKTRAE VKFEGDTLVN        120
RIELKGIDFK EDGNILGHKL EYNFNSHNVY ITADKQKNGI KANFKIRHNV EDGSVQLADH        180
YQQNTPIGDG PVLLPDNHYL STQSVLSKDP NEKRDHMVLL EFVTAAGITH GMDELYKGPV        240
LLPDNHYLST QSVLSKDPNE KRDHMVLLEF VTAAGITHGM DELYKFTGVV PILVELDGDV        300
NGHKFSVRGE GEGDATNGKL TLKFICTTGK LPVPWPTLVT TLTYGVQCFS RYPDHMKRHD        360
FFKSAMPEGY                                                              370

SEQ ID NO: 34                   moltype = AA  length = 182
FEATURE                         Location/Qualifiers
source                          1..182
                                mol_type = protein
                                organism = synthetic construct
SEQUENCE: 34
GPGSDKDCEM KRTTLDSPLG KLELSGCEQG LHEIIFLGKG TSAADAVEVP APAAVLGGPE         60
PLMQATAWLN AYFHQPEAIE EFPVPALHHP VFQQESFTRQ VLWKLLKVVK FGEVISYSHL        120
AALAGNPAAT AAVKTALSGN PVPILIPCHR VVQGDLDVGG YEGGLAVKEW LLAHEGHRLG        180
KR                                                                      182

SEQ ID NO: 35                   moltype = AA  length = 7
FEATURE                         Location/Qualifiers
source                          1..7
                                mol_type = protein
                                organism = synthetic construct
SEQUENCE: 35
ENLYFQG                                                                   7

SEQ ID NO: 36                   moltype = AA  length = 5
FEATURE                         Location/Qualifiers
source                          1..5
                                mol_type = protein
                                organism = synthetic construct
SEQUENCE: 36
GGGGS                                                                     5

SEQ ID NO: 37                   moltype = AA  length = 10
FEATURE                         Location/Qualifiers
source                          1..10
                                mol_type = protein
                                organism = synthetic construct
SEQUENCE: 37
GGGGSGGGGS                                                               10

SEQ ID NO: 38                   moltype = AA  length = 15
FEATURE                         Location/Qualifiers
source                          1..15
                                mol_type = protein
                                organism = synthetic construct
SEQUENCE: 38
GGGGSGGGGS GGGGS                                                         15

SEQ ID NO: 39                   moltype = AA  length = 20
FEATURE                         Location/Qualifiers
source                          1..20
                                mol_type = protein
                                organism = synthetic construct
SEQUENCE: 39
GGGGSGGGGS GGGGSGGGGS                                                    20

SEQ ID NO: 40                   moltype = AA  length = 6
FEATURE                         Location/Qualifiers
source                          1..6
                                mol_type = protein
                                organism = synthetic construct
SEQUENCE: 40
ENLYFQ                                                                    6
```

```
SEQ ID NO: 41            moltype = AA  length = 4
FEATURE                  Location/Qualifiers
source                   1..4
                         mol_type = protein
                         organism = synthetic construct
SEQUENCE: 41
GAAS                                                                       4

SEQ ID NO: 42            moltype = AA  length = 123
FEATURE                  Location/Qualifiers
source                   1..123
                         mol_type = protein
                         organism = synthetic construct
SEQUENCE: 42
ENLYGQGAAS QVQLVESGGG VVQPGRSLRL DCKASGITFS NSGMHWVRQA PGKGLEWVAV           60
IWYDGSKRYY ADSVKGRFTI SRDNSKNTLF LQMNSLRAED TAVYYCATND DYWGQGTGVR          120
VSS                                                                      123

SEQ ID NO: 43            moltype = AA  length = 11
FEATURE                  Location/Qualifiers
source                   1..11
                         mol_type = protein
                         organism = synthetic construct
SEQUENCE: 43
WGQGTGVTVS S                                                              11

SEQ ID NO: 44            moltype = AA  length = 11
FEATURE                  Location/Qualifiers
source                   1..11
                         mol_type = protein
                         organism = synthetic construct
SEQUENCE: 44
WGQGTLVRVS S                                                              11

SEQ ID NO: 45            moltype = DNA  length = 33
FEATURE                  Location/Qualifiers
source                   1..33
                         mol_type = other DNA
                         organism = synthetic construct
SEQUENCE: 45
ggccagggca ccctggtgag ggtgagcagc ggc                                       33

SEQ ID NO: 46            moltype = DNA  length = 33
FEATURE                  Location/Qualifiers
source                   1..33
                         mol_type = other DNA
                         organism = synthetic construct
SEQUENCE: 46
ggccagggca ccggggtgag ggtgagcagc ggc                                       33

SEQ ID NO: 47            moltype = AA  length = 5
FEATURE                  Location/Qualifiers
source                   1..5
                         mol_type = protein
                         organism = synthetic construct
REPEAT                   1..5
                         note = 1,2,3,4,5 repeats
SEQUENCE: 47
GGGGS                                                                      5

SEQ ID NO: 48            moltype = AA  length = 252
FEATURE                  Location/Qualifiers
source                   1..252
                         mol_type = protein
                         organism = synthetic construct
SEQUENCE: 48
HHHHHHENLY FQGAASQVQL KESGGGVVQP GRSLRLDCKA SGITFSNSGM HWVRQAPGKG           60
LEWVAVIWYD GSKRYYADSV KGRFTISRDN SKNTLFLQMN SLRAEDTAVY YCATNDDYWG          120
QGTLVTVSSG GGGSGGGGSG GGGSEIVLTQ SPATLSLSPG ERATLSCRAS QSVSSYLAWY          180
QQKPGQAPRL LIYDASNRAT GIPARFSGSG SGTDFTLTIS SLEPEDFAVY YCQQSSNWPR          240
TFGQGTKVEI KR                                                            252

SEQ ID NO: 49            moltype = AA  length = 144
FEATURE                  Location/Qualifiers
source                   1..144
                         mol_type = protein
                         organism = synthetic construct
SEQUENCE: 49
HHHHHHENLY FQGAASQVQL VESGGGVVQP GRSLRLDCKA SGITFSNSGM HWVRQAPGKG           60
```

LEWVAVIWYD GSKRYYADSV KGRFTISRDN SKNTLFLQMN SLRAEDTAVY YCATNDDYWG   120
QGTLVTVSSG GGGSGGGGSG GGGS                                         144

SEQ ID NO: 50              moltype = DNA   length = 432
FEATURE                    Location/Qualifiers
source                     1..432
                           mol_type = other DNA
                           organism = synthetic construct
SEQUENCE: 50
caccatcacc atcaccatga aaacctgtat ttccagggag cagcctcgca ggtgcagctg    60
gtggaaagcg gcggcggcgt ggtgcagccg ggccgcagcc tgcgcctgga ttgcaaagcg   120
agcggcatta cctttagcaa cagcggcatg cattgggtgc gccaggcgcc gggcaaaggc   180
ctggaatggg tggcggtgat ttggtatgat ggcagcaaac gctattatgc ggatagcgtg   240
aaaggccgct ttaccattag ccgcgataac agcaaaaaca ccctgtttct gcagatgaac   300
agcctgcgcg cggaagatac cgcggtgtat tattgcgcga ccaacgatga ttattggggc   360
cagggcaccc tggtgaccgt gagcagcggc ggcggcggca gcggcggcgg cggcagcggc   420
ggcggcggca gc                                                      432

SEQ ID NO: 51              moltype = DNA   length = 432
FEATURE                    Location/Qualifiers
source                     1..432
                           mol_type = other DNA
                           organism = synthetic construct
SEQUENCE: 51
gtggtagtgg tagtggtact tttgacata aaggtccctc gtcggagcgt ccacgtcgac    60
cacctttcgc cgccgccgca ccacgtcggc cggcgtcgg aacgcggacct aacgtttcgc   120
tcgccgtaat ggaaatcgtt gtcgccgtac gtaacccacg cggtccgcgg cccgtttccg   180
gaccttaccc accgccacta aaccatacta ccgtcgtttg cgataatacg cctatcgcac   240
tttccggcga aatggtaatc ggcgctattg tcgttttttgt gggacaaaga cgtctacttg   300
tcggacgcgc gcctctatg cgccacata ataacgcgct ggttgctact aataaccccg   360
gtcccgtggg accactggca ctcgtcgccg ccgccgccgt cgccgccgcc gccgtcgccg   420
ccgccgccgt cg                                                      432

SEQ ID NO: 52              moltype = AA    length = 144
FEATURE                    Location/Qualifiers
source                     1..144
                           mol_type = protein
                           organism = synthetic construct
SEQUENCE: 52
HHHHHHENLY FQGAASQVQL VESGGGVVQP GRSLRLDCKA SGITFSNSGM HWVRQAPGKG    60
LEWVAVIWYD GSKRYYADSV KGRFTISRDN SKNTLFLQMN SLRAEDTAVY YCATNDDYWG   120
QGTGVRVSSG GGSGGGGSG GGGS                                          144

SEQ ID NO: 53              moltype = DNA   length = 432
FEATURE                    Location/Qualifiers
source                     1..432
                           mol_type = other DNA
                           organism = synthetic construct
SEQUENCE: 53
caccatcacc atcaccatga aaacctgtat ttccagggag cagcctcgca ggtgcagctg    60
gtggaaagcg gcggcggcgt ggtgcagccg ggccgcagcc tgcgcctgga ttgcaaagcg   120
agcggcatta cctttagcaa cagcggcatg cattgggtgc gccaggcgcc gggcaaaggc   180
ctggaatggg tggcggtgat ttggtatgat ggcagcaaac gctattatgc ggatagcgtg   240
aaaggccgct ttaccattag ccgcgataac agcaaaaaca ccctgtttct gcagatgaac   300
agcctgcgcg cggaagatac cgcggtgtat tattgcgcga ccaacgatga ttattggggc   360
cagggcaccg gggtgagggt gagcagcggc ggcggcggca gcggcggcgg cggcagcggc   420
ggcggcggca gc                                                      432

SEQ ID NO: 54              moltype = DNA   length = 432
FEATURE                    Location/Qualifiers
source                     1..432
                           mol_type = other DNA
                           organism = synthetic construct
SEQUENCE: 54
gtggtagtgg tagtggtact tttgacata aaggtccctc gtcggagcgt ccacgtcgac    60
cacctttcgc cgccgccgca ccacgtcggc cggcgtcgg acgcggacct aacgtttcgc   120
tcgccgtaat ggaaatcgtt gtcgccgtac gtaacccacg cggtccgcgg cccgtttccg   180
gaccttaccc accgccacta aaccatacta ccgtcgtttg cgataatacg cctatcgcac   240
tttccggcga aatggtaatc ggcgctattg tcgttttttgt gggacaaaga cgtctacttg   300
tcggacgcgc gcctctatg cgccacata ataacgcgct ggttgctact aataaccccg   360
gtcccgtgga acactccca ctcgtcgccg ccgccgccgt cgccgccgcc gccgtcgccg   420
ccgccgccgt cg                                                      432

SEQ ID NO: 55              moltype = AA    length = 32
FEATURE                    Location/Qualifiers
source                     1..32
                           mol_type = protein
                           organism = synthetic construct
SEQUENCE: 55

```
ATNDDYWGQG TLVTVSSGGG GSGGGGSGGG GS                              32

SEQ ID NO: 56            moltype = AA   length = 36
FEATURE                  Location/Qualifiers
source                   1..36
                         mol_type = protein
                         organism = synthetic construct
SEQUENCE: 56
ARDRSYYLDY WGQGTLVTVS SGGGGSGGGG SGGGGS                          36

SEQ ID NO: 57            moltype = AA   length = 31
FEATURE                  Location/Qualifiers
source                   1..31
                         mol_type = protein
                         organism = synthetic construct
SEQUENCE: 57
ARDFSWRGYY MDVWGKGTLV TVSSGSGGGG S                               31

SEQ ID NO: 58            moltype = AA   length = 28
FEATURE                  Location/Qualifiers
source                   1..28
                         mol_type = protein
                         organism = synthetic construct
SEQUENCE: 58
ARFAGGWGAY DVWGQGTLVT VSSGGGGS                                   28

SEQ ID NO: 59            moltype = AA   length = 32
FEATURE                  Location/Qualifiers
source                   1..32
                         mol_type = protein
                         organism = synthetic construct
SEQUENCE: 59
AKPFPYFDYW GQGTLVTVSS GDGSSGGSGG AS                              32

SEQ ID NO: 60            moltype = AA   length = 26
FEATURE                  Location/Qualifiers
source                   1..26
                         mol_type = protein
                         organism = synthetic construct
SEQUENCE: 60
ARGIAGGWAF WGIDLWGQGT LVTVSS                                     26

SEQ ID NO: 61            moltype = AA   length = 39
FEATURE                  Location/Qualifiers
source                   1..39
                         mol_type = protein
                         organism = synthetic construct
SEQUENCE: 61
ATDPPGLRFR FDYWGQGTLV TVSSGGGGSG GGGSGGGS                        39

SEQ ID NO: 62            moltype = AA   length = 32
FEATURE                  Location/Qualifiers
source                   1..32
                         mol_type = protein
                         organism = synthetic construct
SEQUENCE: 62
ATNDDYWGQG TLVTVSSGGG GSGGGGSGGG GS                              32

SEQ ID NO: 63            moltype = AA   length = 42
FEATURE                  Location/Qualifiers
source                   1..42
                         mol_type = protein
                         organism = synthetic construct
SEQUENCE: 63
ARDGKSINGY SGVLDYWGQG SLVTVSSGGG GSGGGGSGGG GS                   42

SEQ ID NO: 64            moltype = AA   length = 32
FEATURE                  Location/Qualifiers
source                   1..32
                         mol_type = protein
                         organism = synthetic construct
SEQUENCE: 64
ARINAKWGQG TLVTVSSGGG GSGGGGSGGS AL                              32

SEQ ID NO: 65            moltype = AA   length = 36
FEATURE                  Location/Qualifiers
source                   1..36
                         mol_type = protein
                         organism = synthetic construct
```

```
SEQUENCE: 65
AKGNSGFDYW GQGTLVTVSS GGGGSGGGGS GGGGST                                 36

SEQ ID NO: 66          moltype = AA  length = 48
FEATURE                Location/Qualifiers
source                 1..48
                       mol_type = protein
                       organism = synthetic construct
SEQUENCE: 66
ARGAMKDYDF WSGYRHLGAF DIWGQGTLVT VSSGGGGSGG GGSGGGGS                    48

SEQ ID NO: 67          moltype = AA  length = 45
FEATURE                Location/Qualifiers
source                 1..45
                       mol_type = protein
                       organism = synthetic construct
SEQUENCE: 67
ATAFSPPTQT SGWGRSSDSW GQGTLVTVSS GGGGSGGGGS GGGGS                       45

SEQ ID NO: 68          moltype = AA  length = 26
FEATURE                Location/Qualifiers
source                 1..26
                       mol_type = protein
                       organism = synthetic construct
SEQUENCE: 68
AKSTSSFDYW GQGTLVTVSS GGGGST                                            26

SEQ ID NO: 69          moltype = AA  length = 39
FEATURE                Location/Qualifiers
source                 1..39
                       mol_type = protein
                       organism = synthetic construct
SEQUENCE: 69
AKVRDSGYDF APFDIWGQGT MVTVSSGSAS APTLFPLVS                              39

SEQ ID NO: 70          moltype = AA  length = 36
FEATURE                Location/Qualifiers
source                 1..36
                       mol_type = protein
                       organism = synthetic construct
SEQUENCE: 70
AKSDHTFDYW GQGTLVTVSS GGGGSGGGGS GGGGST                                 36

SEQ ID NO: 71          moltype = AA  length = 36
FEATURE                Location/Qualifiers
source                 1..36
                       mol_type = protein
                       organism = synthetic construct
SEQUENCE: 71
AKGGAAFDYW GQGTLVTVSS GGGGSGGGGS GGGGST                                 36

SEQ ID NO: 72          moltype = AA  length = 46
FEATURE                Location/Qualifiers
source                 1..46
                       mol_type = protein
                       organism = synthetic construct
SEQUENCE: 72
AKDGRYNWNY GAFDIWGQGT MVTVSSGGGG SGGGGSGGGG SGGGGS                      46

SEQ ID NO: 73          moltype = AA  length = 37
FEATURE                Location/Qualifiers
source                 1..37
                       mol_type = protein
                       organism = synthetic construct
SEQUENCE: 73
ATNDDYWGQG TLVTVSSGGG GSGGGGSGGG GSGGGGS                                37

SEQ ID NO: 74          moltype = AA  length = 34
FEATURE                Location/Qualifiers
source                 1..34
                       mol_type = protein
                       organism = synthetic construct
SEQUENCE: 74
AKPFPYFDYW GQGTLVTVSS GDGSSGGSGG ASTG                                   34

SEQ ID NO: 75          moltype = AA  length = 36
FEATURE                Location/Qualifiers
source                 1..36
                       mol_type = protein
```

```
                    organism = synthetic construct
SEQUENCE: 75
AKDATTFDYW GQGTLVTVSS GGGGSGGGGS GGGGST                         36

SEQ ID NO: 76         moltype = AA  length = 36
FEATURE               Location/Qualifiers
source                1..36
                      mol_type = protein
                      organism = synthetic construct
SEQUENCE: 76
AKDCATFDYW GQGTLVTVSS GGGGSGGGGS GGGGST                         36
```